US008497101B2

(12) United States Patent
Mechali et al.

(10) Patent No.: US 8,497,101 B2
(45) Date of Patent: Jul. 30, 2013

(54) USE OF A NEW GENE CODING FOR A NEW MEMBER OF THE MCM2-8 FAMILY IN PHARMACEUTICAL COMPOSITIONS

(75) Inventors: Marcel Mechali, Montferrier sur Lez (FR); Domenico Maiorano, Saint-Martin de Londres (FR); Malik Lutzmann, Montpellier (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 990 days.

(21) Appl. No.: 11/914,374

(22) PCT Filed: May 12, 2006

(86) PCT No.: PCT/EP2006/004509
§ 371 (c)(1),
(2), (4) Date: Sep. 17, 2008

(87) PCT Pub. No.: WO2006/120019
PCT Pub. Date: Nov. 16, 2006

(65) Prior Publication Data
US 2011/0023135 A1    Jan. 27, 2011

(51) Int. Cl.
*C12P 7/60*     (2006.01)
*A61K 38/43*    (2006.01)

(52) U.S. Cl.
USPC ......................................... 435/138; 424/94.1

(58) Field of Classification Search
None
See application file for complete search history.

(56) References Cited

FOREIGN PATENT DOCUMENTS
WO      2006/084694 A2    8/2006

OTHER PUBLICATIONS

Klein et al., Genetic and genomic tools for Xenopus research: The NIH Xenopus initiative., Developmental Dynamics., 2002, vol. 225, pp. 384-391.*
The MGC Project Team, The status, quality, and expansion of the NIH full-length cDNA project: the Mammalian Gene Collection (MGC)., Genome Res., Oct. 14, 2004, vol. 10B, pp. 2121-2127.*
Mungall et al., The DNA sequence and analysis of human chromosome 6., Nature, 2003, vol. 425, pp. 805-811.*
Guo et al., Protein tolerance to random amino acid change, 2004, Proc. Natl. Acad. Sci. USA 101: 9205-9210.*
Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from *Escherichia coli*, 1998, Biochem. Biophys. Res. Comm. 244:573-577.*
Wacey et al., Disentangling the perturbational effects of amino acid substitutions in the DNA-binding domain of p53., Hum Genet, 1999, vol. 104, pp. 15-22.*
Yoshida, K., "Identification of a novel cell-cycle-induced MCM family protein MCM9", Biochemical and Biophysical Research Communication, Academic Press Inc. Orlando, FL, US, vol. 331, No. 2, Apr. 9, 2005, pp. 669-674.

(Continued)

*Primary Examiner* — Alexander Kim
(74) *Attorney, Agent, or Firm* — Young & Thompson

(57) ABSTRACT

The use of the human or animal MCM9 gene, or parts of the gene, or transcripts thereof, or antisense nucleic acids able to hybridize with part of the gene or transcripts, or silencing RNA derived from parts of the transcripts and able to repress the MCM9 gene, or proteins or peptidic fragments translated from the transcripts, or antibodies directed against the proteins or peptidic fragments, for the preparation of a pharmaceutical composition for the treatment of a human or animal pathology linked to a dysfunction of the expression of the MCM9 gene, or of human or animal cancers.

3 Claims, 11 Drawing Sheets

OTHER PUBLICATIONS

Database UniProt, "Minichromosome maintenance deficient domain containing 1.", Oct. 1, 2002, XP002399771, Database accession No. Q8N5S5, XP0048676, ISSN: 0006-291X.

Database UniProt, Jul. 5, 2004, "MCM9 protein", XP002399772, Database accession No. Q6nrm6.

Database EMBL May 12, 2006 "*Xenopus laevis* mino-chromosome maintenance deficient 9, mRNA", XP002399773, Database accession No. BC070720.

Database UniProt, Jul. 5, 2004, "Mcmdc1 protein fragment", XP002422682, Database accession No. Q6p6j6.

& Databae EMBL, Nov. 15, 2003, "Mus musculus minichromosome mantenance deficient domain containing 1, particial cds" XP002422683, Database accession No. BC062185.

Lutzmann et al. "Indentification on full genes and proteins of MCM9, a novel vertebrate-specific member of the MCM2-8 protein family" Gene: An International Journal of Genes and Genomes, Elsevier, Amsterdam, NL, vol. 362, Dec. 5, 2005, pp. 51-56, XP005162054 ISSN: 0378-119.

Maiorano D. et al., "MCM8 is an MCM2-7-related protein that functions as a DNA helicase during replication elongation and not initiation" Cell, Cell Press, Cambridge, NA, US, vol. 120, No. 3, Feb. 10, 2005, pp. 315-328, XP002375862, ISSN: 0092-8674.

Freeman, A. et al., "Minichromosome maintenance proteins as biological markers of dysplasia and malignancy", Clinical Cancer Research: An Official Journal of the American Association for the Cancer Research, Aug. 1999, vol. 5, No. 8, pp. 2121-2132, XP002399767, ISSN: 1078-0432.

Forsburg S. L. "Eukaryotic MCM proteins: Beyond replication initiation" Microbiology and Molecular Biology Reviews, American Society for Microbiology, US, vol. 68, No. 1, Mar. 2004, p. 109-131, X002393215, ISSN: 1092-2172.

International Search Report of PCT/EP2006/004509 filed May 12, 2006, date of mailing Mar. 23, 2007.

* cited by examiner

```
Human     ------------------------------------------------------------
Mouse     MDQRTTRNGKYCDVEPVSRSNPAPCLRDP PLPRLVRPKPRLQLPESRLSPCSRLPLADSS  60
Chicken   ------------------------------------------------------------
Xenopus   ------------------------------------------------------------

Human     ------------------------------------------------------------
Mouse     VRPGARPPASAPGRSPSGRKVEAVRGSGS AGSSSPSEAEREQREEACAPPRKAAPSSGRA 120
Chicken   ------------------------------------------------------------
Xenopus   ------------------------------------------------------------

Human     ----------------------------------------MNSDQVTLVGQVFESYVSEYHKND  24
Mouse     HAPPPPTPRGSGWGDHGRSAVPATKTVRV EPYPPFKMNSEQVTLVGQVFESYVSEYHKND 180
Chicken   ---------------------------------------MALRADQVSLIGQVFESYLLQHHRDD  26
Xenopus   ---------------------------------------MYLGFEQVALVGQVFESFVLEHHKNE  26
                                                 :  ;**:*:******:: ::*:::

Human     ILLILKERDEDAHYPVVVNAMTLFETNME IGEYFNMFPSEVLTIFDSALRRSALTILQSL  84
Mouse     ILLILKERDEDAHYPVVVNAMSLFETNME IGDYFTVFPNEVLTVFDSALRRSALAILQSL 240
Chicken   ILGILRQGDDEAHYPVLVDALTLFETNME IGEYFNAFPSQVLPIFDGALRRAAMAVLQAA  86
Xenopus   IAQILTEKEEHAHYSLVVNAMTLFEANME IGEYFNAFPNEVLPVFDNAURCAAMSFLQSC  86
          *  **  :  ::.***.::*:*::***:****.**,,**:,**.***  :*::.**:

Human     SQPEAVSMKQNLHARISGLPVCPELVREH IPKTKDVGHFLSVTGTVIRTSLVKVLEFERD 144
Mouse     PETEGLSMKQNLHARISGLPVCPELVREH IPKTKDVGHFLSVTGTVIRTSLVKVLEFERD 300
Chicken   TPSPELRMKPNLHARISGLPICPELTREH IPKTRDVGHFLSVTGTVIRTSLVKVLEFERS 146
Xenopus   SEKYTFLMKQNLHARITGLPVCPELTREH IPRTRDVGHFLSVTGTVIRTSLVKVLEYEQD 146
            .  **.**.*******:****.**** **:*:******************::.

Human     YMCNKCKHVFVIKADFEQYYTFCRPSSCP SLESCDSSKFTCLSGLSSSPTRCRDYQEIKI 204
Mouse     YMCNKCKHVFVMVEADFEQYYTFSRPSSCP SLASCDSSKFSCLSDLSSSPARCRDYQEIKI 360
Chicken   YICNKCKHVFVAKADFEQYYAFCRPSACL NEEGCNSTKFTCLSGTSSSPSSCRDYQEIKI 206
Xenopus   FMCNKCKHVVTVKADFEQHYTFKPPIACS NEEGCNSTKFTCLSD-SSSPASCRDYQEIKI 205
          ::*******.  :*****:*:*  *  :*    .*:***:**.*,  ****  *********

Human     QEQVQRLSVGSIPRSMKVILEDDLVDSCK SGDDLTIYGIVMQRWKPFQQDVRCEVEIVLK 264
Mouse     QEQVQRLSVGSIPRSMKVILEDDLVDSCK SGDDLTIYGIVMQRWKPFQRDVRCEVEIVLK 420
Chicken   QEQVQRLSVGSIPRCMVVLEDDLVDSCK SGDDITVYGVVMQRWKPFHQDARCDLELVLK 266
Xenopus   QEQVQRLSVGSIPRSMIVLEDDLVDSCK SGDDITVYGVVMQRWKPLYIDMRCDLEIVLK 265
          **************.* *:**********:*** **:***:******   *  **:*:***

Human     ANYIQVNNEQSSGIIMDEEVQKEFEDFWE YYKSDPFAGRNVILASLCPQVFGMYLVKLAV 324
Mouse     ANYVQVNNEQSSGMVMDEDTRKEFEDFWE HYKSDPFAGRNVILASLCPQVFGMYLVKLAV 480
Chicken   ANYVKVNNEQLAGVTIDEEVRKEFEDFWE KHRNNPLAGRNEILASLCPQVFGLYLVKLAV 326
Xenopus   ANYISVNNEQPCGVVINEEVRKEYEDFWV KYRNNPLEGRNEILASLCPQVFGMVVVKLAV 325
          ***:.***** .*: ::*::*:::****  :: *:  *** ***********:  :****

Human     AMVLAGGIQRTDATGTRVRGESHLLLVGDPGTGKSQFLKYAAKITPRSVLTTGIGSTSAG 384
Mouse     AMVLAGGIQRTDAAGTRVRGESHLLLVGDPGTGKSQFLKYAAKITPRSVLTTGIGSTSAG 540
Chicken   AMVLAGGVQRIDATGTRIRGESHLLLVGDPGTGKSQFLKYAVKITPRSVLTAGIGSTSAC 386
Xenopus   AMVLAGGVQRIDSAGTRVRGESHLLLVGDPGTGKSQFLKYAAKITPRSVLTAGIGSTSAG 385
          *******:** *: ***:**********************.*********:******.

Human     LTVTAVKDSGEWNLEAGALVLADAGLCCIDEFNSLKEHDRTSIHEAMEQQTISVAKAGLV 444
Mouse     LTVTAVKDSGEWNLEAGALVLADAGLCCIDEFNSLKEHDRTSIHEAMEQQTISVAKAGLV 600
Chicken   LTVTAVKDFGEWNLEAGALVLADGGLCCIDEFNSIKEHDRTSIHEAMEQQTISVAKAGLV 446
Xenopus   LTVTAVKDSGEWNLEAGALVLADGGLCCIDEFNSIKEHDRTSIHEAMEQQTISVAKAGLV 445
          ********.*************.********** ************************

Human     CKLNTRTTILAATNPKGQYDPQESVSVNIALGSPLLSRFDLILVLLDTKNEDWDRIISSF 504
Mouse     CKLNTRTTILAATNPKGQYDPKESVSVNIALGSPLLSRFDLVLVLLDTRNEDWDRIISSF 660
Chicken   CKLNTRTTILAATNPKGHYDPAESVSVNIALGSPLLSRFDLVLVLLDTKNEEWDRIISSF 506
Xenopus   CKLNTRTTILAATNPKGQYDPDESISVNVALASPLLSRFDLVLVLLDTKNEDWDRIISSF 505
          *****************:*** ***:***:**.********:******:**:********
```

Figure 2A

```
Human      ILENKGYPSKSEKLWSMEKMKTYFCLIRNLQPTLSDVGNQVLLRYYQMRQSDCRNAART  564
Mouse      ILENKGYPSKSENLWSMEKMKTYFCLIRNLHPTLSEVSNQVLLRYYQMRQSDSRNAART  720
Chicken    ILQNKGCPSKSEKLWSMEKMKTYFCLIKRIQPKLSDESNLILVRYYQMRQSDCRNAART  566
Xenopus    ILESKGCPRKSDKLWSMEKMKTYFCLIKNLQPKMSQDANVILVRYYQLQRQSSCRNAART  565
           **:.** * **:;*************:..::*.:*: .* :*:****:****..******

Human      TIRLLESLIRLAEAHARLMFRDTVTLEDAITVVSVMESSMQGGALLGGVNALHTSFPENP  624
Mouse      TIRLLESLIRLAEAHARLMFRSAVTLEDAVTAVSVMESSMQGGALLGGVNALHTSFPENP  780
Chicken    TIRLLESLIRLAEAHARLMFRDTVTLEDAVTVVSVMESSMQGGALLGAINALHTSFPENP  626
Xenopus    TIRLLESLIRLAEAHARIMYRDVVTTEDAITVVSIMESSMQGGALLGGVNALHTSFPENP  625
           *****************:*:*..** ***.*.**:***********.:***********
```

Figure 2A (cont'd)

```
MCM3  K K--FC KAHSK DIFEH LSKSL APSIHG HEYIK KAILC MLLGG NEKVL EN--G TRIRG DIN
MCM7  E E--LR QITEE DFYEK LAASI APEIYG HEDVK KALLL LLVGG VDNSP R---G MKIRG NIN
MCM5  E EEFRR LAAKP DIYET VAKSI APSIYG SSDIK KAIAC LLFGG SRKRL PD--G LTRRG DVN
MCM2  I V----A LSKDE RIGER IFASI APSIYG HEDIK RGLAL ALFGG EAKNP GG--K HKVRG DIN
MCM4  V EKIQQ VSKRD DIYDI LSRSL APSIYE MDDVK KGLLL QLFGG TNKSF HKGAS PRYRC DIN
MCM6  W EKVFE MSQDK NLYHN LCTSL FPTIHG NDEIK RGVLL MLFGG VPKTT MEG-- TSLRG DIN
MCM8  L YAIQE IQSQE NLFQL IVNSL CPTIYG HELVK AGLSL ALFGG CQKYA DDKNR IPIRG DPH
MCM9  D FWVKY RNNPL EGRNE ILASL CPQVFG MFVVK LAVAM VLAGG VQRID SAG-- TRVRG ESH
                .  :   *:  * :.      :*  .:     *  **    .          **: :

MCM3  V LLI GDPSVAK SQLLRYVL HTAPR AIPTT GRGSS GVGLT AAVTTD QETGE RRLEA GAMVL
MCM7  I CLM GDPGVAK SQLLSYID RLAPR SQYTT GRGSS GVGLT AAVMKD PVTGE MTLEG GALVL
MCM5  L LML GDPGTAK SQLLKFVE RCSPI GVYTS GKGSS AAGLT ASVMRD PVSRN FIMEG GAMVL
MCM2  V LLC GDPGTAK SQFLKYVE KVASR AVFTT GQGAS AVGLT AYVQRH PVTKE WTLEA GALVF
MCM4  I LMC GDPSTSK SQILKYVH KIAPR GVYTS GKGSS AVGLT AYITRD QDTKQ LVLES GALVL
MCM6  V CIV GDPSTSK SQFLKHVE EFSPR AVYTS GKASS AAGLT AAVVKD EESHE FVIEA GALML
MCM8  I LVV GDPGLGK SQMLQAVC NVAFR GVYVC GNTTT TSGLT VTLSRD TTTGD FGLEA GALVL
MCM9  L LLV GDPGTGK SQFLKYAA KITPR SVLTA GIGST SAGLT VTAVKD --SGE WNLEA GALVL
          :  ***. .***:*    .  :.    . *   ::  ***.    . :  :  :*.**:::

MCM3  A DRGVV CIDEFDKMSDMDR TAIHE VMEQG RVTIA KAGIQ ARLNAR CSVLA AANPV YGRYD
MCM7  A DQGVC CIDEFDKMMDTDR TAIHE VMEQQ TISIA KAGIM TTLNAR CSILA AANPA YGRYN
MCM5  A DGGVV CIDEFDKMREDDR VAIHE AMEQQ TISIS KAGIV TSLQAR CTVIA AASNPI GGRYD
MCM2  A DRGVC LIDEFDKMNDQDR TSIHE AMEQQ SISIS KAGIV TSLQAR CTVIA ASNPI GGRYD
MCM4  S DGGIC CIDEFDKMSDATR SILHE VMEQQ TVTVA KAGII TTLNAR TSILA SANPI GSKYN
MCM6  A DNGVC CIDEFDKMDLKDQ VAIHE AMEQQ TISIT KAGVK ATLNAR TSILA AANPV GGRYE
MCM8  G DQGIC GIDEFDKMGN-QH QALLE AMEQQ SISLA KAGIV CSLPAR TSIIA AANPV GGHYN
MCM9  A DGGLC CIDEFNSIKEHDR TSIHE AMEQQ TISVA KAGLV CKLNTR TTILA ATNPK -GQYD
       .*  *:  ****:..:    :  : *.***  :::***    :    *  :*  :: :*::*.    .:::

MCM3  Q YRTPM ENIGL QDSLL SRFDL LFIVLD KMDAD NDQEI ADHVL RMHRY RTPGE QDGYA LPL
MCM7  P KKTVE QNIQL PAALL SRFDV LWLIQD KPDRD NDLRL AQHIT YVHQH SK--- ----- ---
MCM5  D TK-GE ENIDF MPTIL SRFDM IFIVKD EHNEQ RDMTL AKHVM NVHLS AR--- ----- ---
MCM2  P SLTFS ENVDL TEPIV SRFDI LCVVRD TVDPV QDEML ARFVV SSHIK HHP-- ----- ---
MCM4  P DLPVT KNIDL PPTLL SRFDL VYLILD RVDET LDRKL ANHIV SMYME DTP-- ----- ---
MCM6  R SKSLK HNVNL SAPIM SRFDL FFILVD ECNEV TDYAI ARRIV DLHAR NEE-- ----- ---
MCM8  K GKTVS ENLKM GSALL SRFDL VFILVD TPNED HDHLL SEHVM AMRSG AKEIQ SVDIT RIN
MCM9  P DESIS VNVAL ASPLL SRFDL VLVLLD TKNED WDRII SSFIL ESKGC PR--- ----- ---
           *:  :  .::****:.  ::  *     *     ::            
```

Figure 2B

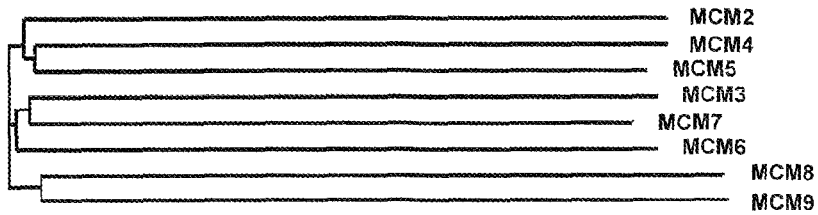

Figure 2C

```
Xenopus     ------LQRLERQQSEDSLESDLGESATNLVGHKVVHS--ECVMEETFSTFEASSLFDETH
Chicken     -----ELQRLDRLQKETYCQLQPEETSFSTITGCLNKNTFESKQKSQSEPSDQQKINSYPQ
Mouse       LLQEELRRLERLQNESVHQCQSHSLEEEVAPGSCRN---DPRDKPRLRTSTQQEQSCS--
Human       ------RRLERLQNQSVHQSQPRVLEVETTPGSLRN---GPGEESNFRTSSQQEINYSTH
                 :**:* *.:       :  :          :              : .  ..

Xenopus     LGVTGSAAFIQTPKKTISDMTKSDDTIRKGTITPAEQNRGISTDAESSLKQGNAQPLAGG
Chicken     PSLPKSNCEGDKHPEALRNPTPGNNISTKRLSRLNKRSDDGSLGWFDRLEDRNTDAEETF
Mouse       --WS---STERS-GADSPPGPGL-NRPTSCNNSAENRDGRGDGLDWLDPTSSPEIAP-EST
Human       IFSPGGSPEGSPVLDPPPHLEP-NRSTSRKHSAQHKNNRDDSLDWFDFMATHQSEPKNTV
               .   ..                 :         . . . .  .           :  .

Xenopus     HLSENNLTKCTDNSLGWFDTLQSIQMSPITKQREGCTAEKLQQEVLPVSTESSCHPADKK
Chicken     WKTSPLPKTSPDN---MALKTMSKSSCSEEGNSSVPRKEDGMRGSLR-TVTLCAPLEQDK
Mouse       IVS-PNVKTTEKN---VNLKISNNKSQGKEKHGPQQRSKLLEAGHLPSSGAMNAPLRSHG
Human       VVS-PHPKTSGEN---MASKISNSTSQGKEKSEPGQRSK-VDIGLLPSPGETGVPWRADN
              :   ..  .*                 :             *  .        . .

Xenopus     VVNLGGRNK------LEVLQASGSSPGGNGRDLSNHTVTCGSSPERNKRDLSNHEIVTEHV
Chicken     VSEISSKRTEERKCFSSEANIQDPTSASASVQESVITQRVSKSLQRLHTEKSHRFFTSTQ
Mouse       VKRTKASQ----------AVVVSEAGR-GDEEDS-----VPRRLPKLLKEGSQNVCRST-
Human       VESNKKKR----------LALDSEAAVSADKPDSVLTHHVPRNLQKLCKERAQKLCRNS-
              *                  .  :  .     *            :  ::.. .

Xenopus     SKKWRRINKDSLCGKNVPSFQPQSENTDSAPVCSSVPLHSTPDVAQRRKRIIAQVEKQSK
Chicken     NSEANALPSVLPVSGLLDLSSDTDSVVGDESNSASAAVKHAVISMRKRSKGQAEKEAKAV
Mouse       -TRVRPLPPTVPLS---------------LSIPSPGSGKRSGTPKRKRRKS-AQVEEPEP
Human       -TRVPAQCTVPSHP---------------QSTPVHSPDRRLDSPKRKRPKSLAQVEEPAI
              ..                          . :        *:   :   *: *

Xenopus     AEVEDPDTKAR---LAQLAKFSFKRHSKLVHS--------PAGDTDTASNAQKHDHPVQK
Chicken     SSHEPEITDGESPPAAKLAKFSFRPRTKLDDSSEKKNAEFPLFPSENTVKPGEQPQGEQL
Mouse       EGMETP--------TVKLAKFTFKQKTKLTHSPEGQ-GPIPPSASEIAVDSSKIPQQRTR
Human       ENVKPPGS------PVAKLAKFTFKQKSKLIHSFEDH-SHVSPGAIKIAVHSPKISQRRTR
                 :    . :****:*: ::**  .*                . .      :.

Xenopus     ITLSEKLNNLGRTVNNVDK--------------SSNSVNGSKQQKHVENTSKQTVITQKSN
Chicken     QKDCCPPEKRKMTLTCLGRKGLEK-----QSIGSKGNEEQLSQALGKEMGGNALIHSDVT
Mouse       REAAVPVVAPGKSTSTSGDRCSDQLHGKTKELSRQPPDSNPPREEREQGPKRRVIQPKPE
Human       RDAALPVKRPGKLTSTPGNQISSQPQGETKEVSQQPPEKHGPREKVMCAPEKRIIQPELE
                         .                    .:   :     ::        .:*  .

Xenopus     FESNTLNAPVHETKLN-----EGCDSRKVSSSTLAKLARFSFSPPPENQAAETSKET---
Chicken     LDVVS---PPPTEKRREGEEKLGGPSTVRVCSSTLENLSKFCFASRPDSKSEAPPTIKTDT
Mouse       LGNQAGHSHLACEKDRKEGVSCGNKSSKVHAGTIARLASFSFTSPSESKSESLPPERKDS
Human       LGNETGCAHLTCEGDKKEEVSGSNKSGKVHACTLARLANFCFTPPSESKSKSPPPERKNR
              :     :    .      ..: :* *: .*: *.*:. .::.

Xenopus     --------------LILPRAVAPGSKRKCFELNPSTDKTTMSSKSLFSTTDLDDEELDV
Chicken     NNKESH--------SPLLKVHVSNPKRKSFALGNASKDSVVTRKSLFSIAELDDATLDF
Mouse       RDSRDSRDSRDRCHSPPATTAPVLGQQRQTFQLQQPTERANLSTLSLFTLSELDDEALDF
Human       GERGPS--------SPPTTTAPMRVSKRKSFQLRGSTEKLIVSKESLFTLPELGDEAFDC
                          .:*: * *  .:.   :: ***: .:*,*  :*

Xenopus     DWEAEIKGNQRIAT
Chicken     DWD-----------
Mouse       DWEEEMRKKP----
Human       DWDEEMRKKS----
            **:
```

Figure 2D

SEQUENCE LISTING

```
<160> NUMBER OF SEQ ID NOS: 76

<210> SEQ ID NO 1
<211> LENGTH: 4798
<212> TYPE: DNA
<213> ORGANISM: Homo sapiens
<220> FEATURE:
<221> NAME/KEY: CDS
<222> LOCATION: (1)..(3429)

<400> SEQUENCE: 1 atg aat agc gat caa gtt aca ctg gtt ggt caa gtg ttt gag tca tat      48
Met Asn Ser Asp Gln Val Thr Leu Val Gly Gln Val Phe Glu Ser Tyr
1               5                   10                  15 gtt tcg gaa tac cat aag aat gat att ctt cta atc ttg aag gaa agg      96
Val Ser Glu Tyr His Lys Asn Asp Ile Leu Leu Ile Leu Lys Glu Arg
            20                  25                  30 gat gaa gat gct cat tac cca gtt gtg gtt aat gcc atg act ctg ttt     144
Asp Glu Asp Ala His Tyr Pro Val Val Val Asn Ala Met Thr Leu Phe
        35                  40                  45 gag acc aac atg gaa atc ggg gaa tat ttc aac atg ttc ccc agt gaa     192
Glu Thr Asn Met Glu Ile Gly Glu Tyr Phe Asn Met Phe Pro Ser Glu
    50                  55                  60 gtg ctt aca att ttt gat agt gca ctg cga agg tca gcc ttg aca att     240
Val Leu Thr Ile Phe Asp Ser Ala Leu Arg Arg Ser Ala Leu Thr Ile
65                  70                  75                  80 ctc cag tcc ctt tct cag cct gag gct gtt tcc atg aaa cag aat ctt     288
Leu Gln Ser Leu Ser Gln Pro Glu Ala Val Ser Met Lys Gln Asn Leu
                85                  90                  95 cat gcc agg ata tca ggt ttg cct gtc tgt cct gag ctg gtg agg gaa     336
His Ala Arg Ile Ser Gly Leu Pro Val Cys Pro Glu Leu Val Arg Glu
            100                 105                 110 cac ata cct aaa acc aag gat gtg gga cac ttt tta tct gtc act ggg     384
His Ile Pro Lys Thr Lys Asp Val Gly His Phe Leu Ser Val Thr Gly
        115                 120                 125 aca gtg att cga aca agt ctg gtg aag gtt ctg gag ttt gag cgg gat     432
Thr Val Ile Arg Thr Ser Leu Val Lys Val Leu Glu Phe Glu Arg Asp
    130                 135                 140 tac atg tgt aac aaa tgc aag cat gtg ttt gtg atc aag gct gac ttt     480
```

```
                Tyr Met Cys Asn Lys Cys Lys His Val Phe Val Ile Lys Ala Asp Phe
                145                 150                 155                 160 gag cag tat tac acc ttt tgc cgg cca tcc tcg tgt ccc agc ttg gag          528
Glu Gln Tyr Tyr Thr Phe Cys Arg Pro Ser Ser Cys Pro Ser Leu Glu
                165                 170                 175 agc tgt gat tcc tct aaa ttc act tgc ctc tca ggc ttg tct tcg tct          576
Ser Cys Asp Ser Ser Lys Phe Thr Cys Leu Ser Gly Leu Ser Ser Ser
                180                 185                 190 cca acc agg tgt aga gat tac cag gaa atc aaa att cag gaa cag gtt          624
Pro Thr Arg Cys Arg Asp Tyr Gln Glu Ile Lys Ile Gln Glu Gln Val
                195                 200                 205 caa agg cta tct gtt gga agt att cca cga tct atg aag gtt att ctg          672
Gln Arg Leu Ser Val Gly Ser Ile Pro Arg Ser Met Lys Val Ile Leu
210                 215                 220 gaa gat gac tta gtg gat agt tgc aaa tct ggt gat gac ctc act att          720
Glu Asp Asp Leu Val Asp Ser Cys Lys Ser Gly Asp Asp Leu Thr Ile
225                 230                 235                 240 tac ggg att gta atg caa cgg tgg aag ccc ttt cag caa gat gtg cgc          768
Tyr Gly Ile Val Met Gln Arg Trp Lys Pro Phe Gln Gln Asp Val Arg
                245                 250                 255 tgt gaa gtg gag ata gtc ctg aaa gca aat tac atc caa gta aat aat          816
Cys Glu Val Glu Ile Val Leu Lys Ala Asn Tyr Ile Gln Val Asn Asn
                260                 265                 270 gag cag tcc tca ggg atc atc atg gat gag gag gtc caa aag gaa ttc          864
Glu Gln Ser Ser Gly Ile Ile Met Asp Glu Glu Val Gln Lys Glu Phe
                275                 280                 285 gaa gat ttt tgg gaa tac tat aag agc gat ccc ttt gca gga agg aat          912
Glu Asp Phe Trp Glu Tyr Tyr Lys Ser Asp Pro Phe Ala Gly Arg Asn
                290                 295                 300 gta ata ttg gct agc ttg tgc cct caa gtg ttt gga atg tat cta gta          960
Val Ile Leu Ala Ser Leu Cys Pro Gln Val Phe Gly Met Tyr Leu Val
305                 310                 315                 320 aag ctt gct gtg gcc atg gtg ctg gct ggt ggg att caa agg act gat         1008
Lys Leu Ala Val Ala Met Val Leu Ala Gly Gly Ile Gln Arg Thr Asp
                325                 330                 335 gct aca gga aca cgg gtc aga gga gaa tct cat ctt tta ttg gtt ggg         1056
Ala Thr Gly Thr Arg Val Arg Gly Glu Ser His Leu Leu Leu Val Gly
                340                 345                 350 gat cct ggc aca ggg aaa tct cag ttc ctc aaa tat gca gca aag att         1104
Asp Pro Gly Thr Gly Lys Ser Gln Phe Leu Lys Tyr Ala Ala Lys Ile
                355                 360                 365 aca cca aga tct gtg ctg acc aca gga att gga tct act agt gca ggt         1152
Thr Pro Arg Ser Val Leu Thr Thr Gly Ile Gly Ser Thr Ser Ala Gly
                370                 375                 380 ctg acg gta act gct gta aaa gac tca gga gaa tgg aat ttg gag gct         1200
Leu Thr Val Thr Ala Val Lys Asp Ser Gly Glu Trp Asn Leu Glu Ala
385                 390                 395                 400 ggg gca tta gtt ctt gca gat gcg ggc ctt tgc tgt att gat gag ttc         1248
Gly Ala Leu Val Leu Ala Asp Ala Gly Leu Cys Cys Ile Asp Glu Phe
                405                 410                 415 aat agc ctc aaa gag cat gat agg acc agt atc cat gaa gca atg gag         1296
Asn Ser Leu Lys Glu His Asp Arg Thr Ser Ile His Glu Ala Met Glu
                420                 425                 430 caa caa acc ata agt gtt gct aag gct ggc ctc gtg tgc aag ctg aac         1344
Gln Gln Thr Ile Ser Val Ala Lys Ala Gly Leu Val Cys Lys Leu Asn
                435                 440                 445 aca agg acc acc atc ctg gca gca acg aac ccc aaa ggc cag tac gac         1392
Thr Arg Thr Thr Ile Leu Ala Ala Thr Asn Pro Lys Gly Gln Tyr Asp
450                 455                 460 ccc cag gag tcc gtg tct gtg aac att gcc ctc ggc agc cca ctc tta         1440
```

```
                Pro Gln Glu Ser Val Ser Val Asn Ile Ala Leu Gly Ser Pro Leu Leu
                465                 470                 475                 480 agt cga ttt gac ctg atc ctg gtt ttg ctt gat acc aag aat gaa gac          1488
Ser Arg Phe Asp Leu Ile Leu Val Leu Leu Asp Thr Lys Asn Glu Asp
                    485                 490                 495 tgg gat cgt atc att tcc tcc ttt atc tta gaa aat aaa ggt tac cca          1536
Trp Asp Arg Ile Ile Ser Ser Phe Ile Leu Glu Asn Lys Gly Tyr Pro
                500                 505                 510 agc aaa tca gag aag ctc tgg agc atg gaa aag atg aaa acc tat ttc          1584
Ser Lys Ser Glu Lys Leu Trp Ser Met Glu Lys Met Lys Thr Tyr Phe
            515                 520                 525 tgc ctc ata agg aat ctg cag ccc aca ctg tct gat gtg ggc aat cag          1632
Cys Leu Ile Arg Asn Leu Gln Pro Thr Leu Ser Asp Val Gly Asn Gln
        530                 535                 540 gtt ctt ctc cgg tac tac cag atg caa agg cag agt gat tgc cgg aac          1680
Val Leu Leu Arg Tyr Tyr Gln Met Gln Arg Gln Ser Asp Cys Arg Asn
545                 550                 555                 560 gct gcc cgg acc acc att cgg ctg ttg gaa agc ttg ata cga tta gca          1728
Ala Ala Arg Thr Thr Ile Arg Leu Leu Glu Ser Leu Ile Arg Leu Ala
                    565                 570                 575 gaa gct cat gct cgc ctg atg ttt cgt gat act gta act ctg gaa gac          1776
Glu Ala His Ala Arg Leu Met Phe Arg Asp Thr Val Thr Leu Glu Asp
                580                 585                 590 gct att acg gtg gtg tca gtc atg gag tcc tca atg cag gga ggt gca          1824
Ala Ile Thr Val Val Ser Val Met Glu Ser Ser Met Gln Gly Gly Ala
            595                 600                 605 ctg cta gga ggt gtg aat gcc ctc cac act tcc ttt cct gaa aac cct          1872
Leu Leu Gly Gly Val Asn Ala Leu His Thr Ser Phe Pro Glu Asn Pro
        610                 615                 620 gga gag cag tac cag aga cag tgt gaa ctt att ctg gaa aag cta gag          1920
Gly Glu Gln Tyr Gln Arg Gln Cys Glu Leu Ile Leu Glu Lys Leu Glu
625                 630                 635                 640 ctg cag agc ctc ttg agt gaa gag ctt aga aga ctt gaa agg tta cag          1968
Leu Gln Ser Leu Leu Ser Glu Glu Leu Arg Arg Leu Glu Arg Leu Gln
                    645                 650                 655 aat cag agt gtg cac caa tcc caa cca cgg gta ttg gag gta gag act          2016
Asn Gln Ser Val His Gln Ser Gln Pro Arg Val Leu Glu Val Glu Thr
                660                 665                 670 act cca gga tcc ttg aga aat ggt cca ggg gaa gaa tca aac ttc aga          2064
Thr Pro Gly Ser Leu Arg Asn Gly Pro Gly Glu Glu Ser Asn Phe Arg
            675                 680                 685 act tca tca cag cag gaa atc aac tat agc aca cat atc ttc tct cct          2112
Thr Ser Ser Gln Gln Glu Ile Asn Tyr Ser Thr His Ile Phe Ser Pro
        690                 695                 700 gga ggc agc ccc gag gga agc cca gtt cta gat ccc cca ccg cat ctg          2160
Gly Gly Ser Pro Glu Gly Ser Pro Val Leu Asp Pro Pro Pro His Leu
705                 710                 715                 720 gag cct aat aga tca aca agt agg aaa cat tca gct cag cac aaa aat          2208
Glu Pro Asn Arg Ser Thr Ser Arg Lys His Ser Ala Gln His Lys Asn
                    725                 730                 735 aac aga gat gac agt tta gat tgg ttt gat ttc atg gca act cat cag          2256
Asn Arg Asp Asp Ser Leu Asp Trp Phe Asp Phe Met Ala Thr His Gln
                740                 745                 750 agt gaa cct aaa aac act gtt gtt gtg tct cct cat ccc aaa aca tct          2304
Ser Glu Pro Lys Asn Thr Val Val Val Ser Pro His Pro Lys Thr Ser
            755                 760                 765 gga gaa aat atg gct tcg aag atc tct aac agc aca tct cag ggt aag          2352
Gly Glu Asn Met Ala Ser Lys Ile Ser Asn Ser Thr Ser Gln Gly Lys
        770                 775                 780 gag aag agt gag cca ggc caa agg agc aaa gtg gac att ggg ttg ctt          2400
```

-continued

```
Glu Lys Ser Glu Pro Gly Gln Arg Ser Lys Val Asp Ile Gly Leu Leu
785             790                 795                 800 cca tca cca gga gag aca ggt gtt cca tgg agg gca gac aat gtg gaa    2448
Pro Ser Pro Gly Glu Thr Gly Val Pro Trp Arg Ala Asp Asn Val Glu
            805                 810                 815 agt aac aag aaa aaa agg cta gca cta gat tct gaa gca gca gtc tct    2496
Ser Asn Lys Lys Lys Arg Leu Ala Leu Asp Ser Glu Ala Ala Val Ser
        820                 825                 830 gct gat aaa cca gac tca gta ctg act cat cat gtc ccc agg aac ctg    2544
Ala Asp Lys Pro Asp Ser Val Leu Thr His His Val Pro Arg Asn Leu
    835                 840                 845 cag aag ctg tgc aaa gag agg gcc cag aag ttg tgc aga aat agc acc    2592
Gln Lys Leu Cys Lys Glu Arg Ala Gln Lys Leu Cys Arg Asn Ser Thr
850                 855                 860 agg gtg cct gca cag tgc aca gtc cct tcc cat cct cag tcc act cct    2640
Arg Val Pro Ala Gln Cys Thr Val Pro Ser His Pro Gln Ser Thr Pro
865                 870                 875                 880 gta cat agc cca gac aga agg ctg gac tca ccc aaa aga aag aga ccg    2688
Val His Ser Pro Asp Arg Arg Leu Asp Ser Pro Lys Arg Lys Arg Pro
            885                 890                 895 aaa tcc ctt gcg caa gtg gaa gag cct gca att gaa aat gtt aag cct    2736
Lys Ser Leu Ala Gln Val Glu Glu Pro Ala Ile Glu Asn Val Lys Pro
        900                 905                 910 cca ggt tcc cct gtg gcc aaa ctg gca aaa ttt act ttc aag cag aag    2784
Pro Gly Ser Pro Val Ala Lys Leu Ala Lys Phe Thr Phe Lys Gln Lys
    915                 920                 925 tca aaa ctg atc cac tcc ttt gaa gat cac agc cat gtg tca cct ggt    2832
Ser Lys Leu Ile His Ser Phe Glu Asp His Ser His Val Ser Pro Gly
930                 935                 940 gca act aaa ata gca gtt cat agt cct aaa att tcc cag cgt aga aca    2880
Ala Thr Lys Ile Ala Val His Ser Pro Lys Ile Ser Gln Arg Arg Thr
945                 950                 955                 960 aga aga gac gca gcc ttg ccg gtg aag cgt cca gga aag tta aca tct    2928
Arg Arg Asp Ala Ala Leu Pro Val Lys Arg Pro Gly Lys Leu Thr Ser
            965                 970                 975 acc cca gga aac cag atc tcc agt cag cca cag ggt gag aca aag gag    2976
Thr Pro Gly Asn Gln Ile Ser Ser Gln Pro Gln Gly Glu Thr Lys Glu
        980                 985                 990 gtg tcg cag cag cca cca gag aaa  cac gga cca aga gag  aag gtg atg   3024
Val Ser Gln Gln Pro Pro Glu Lys  His Gly Pro Arg Glu  Lys Val Met
        995                 1000                1005 tgt gcc cct gag aag agg att  att cag cct gaa tta  gag ctt ggg        3069
Cys Ala Pro Glu Lys Arg Ile  Ile Gln Pro Glu Leu  Glu Leu Gly
    1010                1015                    1020 aac gag act ggg tgt gct cat  ctt act tgt gag gga  gac aaa aag        3114
Asn Glu Thr Gly Cys Ala His  Leu Thr Cys Glu Gly  Asp Lys Lys
    1025                1030                    1035 gaa gag gtt tca ggc agt aat  aaa agc ggc aag gtt  cat gcc tgc        3159
Glu Glu Val Ser Gly Ser Asn  Lys Ser Gly Lys Val  His Ala Cys
    1040                1045                    1050 aca tta gcc aga ttg gca aac  ttc tgc ttt act ccc  cca tcg gaa        3204
Thr Leu Ala Arg Leu Ala Asn  Phe Cys Phe Thr Pro  Pro Ser Glu
    1055                1060                    1065 tcc aaa tca aaa tcc cct cct  cct gaa agg aag aac  cga ggt gag        3249
Ser Lys Ser Lys Ser Pro Pro  Pro Glu Arg Lys Asn  Arg Gly Glu
    1070                1075                    1080 aga ggc cca agc tcc cct cct  aca acc aca gct cca  atg cgt gtc        3294
Arg Gly Pro Ser Ser Pro Pro  Thr Thr Thr Ala Pro  Met Arg Val
    1085                1090                    1095 agt aaa agg aaa tct ttt cag  ctc cgt ggg tcc acc  gag aaa ctg        3339
```

```
Ser Lys Arg Lys Ser Phe Gln Leu Arg Gly Ser Thr Glu Lys Leu
    1100                1105                1110 att gtt tcc aaa gaa tcc ctc ttc act tta cca gaa cta ggt gat      3384
Ile Val Ser Lys Glu Ser Leu Phe Thr Leu Pro Glu Leu Gly Asp
1115                1120                1125 gaa gca ttt gat tgt gac tgg gat gaa gag atg aga aaa aag tca      3429
Glu Ala Phe Asp Cys Asp Trp Asp Glu Glu Met Arg Lys Lys Ser
1130                1135                1140 tagttgggaa aagctttctg gtcaaatctc accttcttca actccacaga ggaccttcag   3489
gatatcaata tggtatttat aaatgtatag aacaattggc catattgagg atcactctga   3549
atactggctc cccttaagg ctttctaatt tcaggttaat cttcatgact taaaaagttg    3609
tataatcagt tgaggtcagt gtgataccag cagctgagct gaattaatta tgttgtgctt   3669
aattttacaa atggagtact tgtattcctg ttcctgaagc tgtttctgtt ttttgttttg   3729
ttttgttttt aagggggaga ggttcttccc tagattaatt tcttctttca ttcactcagg   3789
aacaaatgtc aagaaggtag cactcataaa tctaacaagg cagatgaact cttttctact   3849
tttttttttt ttttttgtat tttcacctgg aatgggctaa gtacagtgaa tataatcact   3909
tggatgattt gccaaaatca gactattttt ctagtattat ttttgtattg atttgtgtgg   3969
atcaggttaa atgtgactaa tgcttttctt tctttgagag gtatccttac aattccatga   4029
tgttcttaga gatctggcca ctggtcaaac agtaccttc tgaagtactg accttctgag    4089
ttgtcctttc tttcttgagc caacattttg tacttcagat tcttttttct cttgggggcc   4149
taccttcaac caagtaaaat actgtgatta agaagagaga gagtatgagc caggcacagt   4209
gactcactcc tgtagtccta gctactcggg gaggctgagg caggatgatt gcttaagccc   4269
aggagttcgg ggtacagtg agctgtggtc acaccactgt attccagcct gggtgacaga    4329
gtgagatcct gtctctaaaa ataaaataaa tgaagaagag agactatgtg gtagtctcaa   4389
tcaaacatca tgtctcatct acccagctgg ttaaatgga aatgtgattc ctactaagtt    4449
gtgattcact tgtctttaaa accaaggaaa ttatgtactg ttttggtca gaatagataa    4509 cctcaagctt tgtctttcta tgtgctttta aaatcactta ttcctttgga ttctaataag   4569
ggttattagg attcagtaat tatggacttt ctcttctgaa gtgtgaattt gtaaactgat   4629
tgtttaattg tcagagggac ttttggacat agaatactca aaactatatg tattttgttt   4689
aattttcact tcattcaatt cacgcattga aaacaaattt agaaaatcca attttttctta  4749 agcatttaaa cgttctaaaa ttcactaata aaattttctg aaaaaattt               4798
```

<210> SEQ ID NO 2
<211> LENGTH: 1143
<212> TYPE: PRT
<213> ORGANISM: Homo sapiens

<400> SEQUENCE: 2

Met Asn Ser Asp Gln Val Thr Leu Val Gly Gln Val Phe Glu Ser Tyr
1               5                   10                  15

Val Ser Glu Tyr His Lys Asn Asp Ile Leu Leu Ile Leu Lys Glu Arg
            20                  25                  30

Asp Glu Asp Ala His Tyr Pro Val Val Asn Ala Met Thr Leu Phe
        35                  40                  45

Glu Thr Asn Met Glu Ile Gly Glu Tyr Phe Asn Met Phe Pro Ser Glu
    50                  55                  60

Val Leu Thr Ile Phe Asp Ser Ala Leu Arg Arg Ser Ala Leu Thr Ile
65                  70                  75                  80

```
Leu Gln Ser Leu Ser Gln Pro Glu Ala Val Ser Met Lys Gln Asn Leu
                85                  90                  95
His Ala Arg Ile Ser Gly Leu Pro Val Cys Pro Glu Leu Val Arg Glu
            100                 105                 110
His Ile Pro Lys Thr Lys Asp Val Gly His Phe Leu Ser Val Thr Gly
        115                 120                 125
Thr Val Ile Arg Thr Ser Leu Val Lys Val Leu Glu Phe Glu Arg Asp
    130                 135                 140
Tyr Met Cys Asn Lys Cys Lys His Val Phe Val Ile Lys Ala Asp Phe
145                 150                 155                 160
Glu Gln Tyr Tyr Thr Phe Cys Arg Pro Ser Ser Cys Pro Ser Leu Glu
                165                 170                 175
Ser Cys Asp Ser Ser Lys Phe Thr Cys Leu Ser Gly Leu Ser Ser Ser
            180                 185                 190
Pro Thr Arg Cys Arg Asp Tyr Gln Glu Ile Lys Ile Gln Glu Gln Val
        195                 200                 205
Gln Arg Leu Ser Val Gly Ser Ile Pro Arg Ser Met Lys Val Ile Leu
    210                 215                 220
Glu Asp Asp Leu Val Asp Ser Cys Lys Ser Gly Asp Asp Leu Thr Ile
225                 230                 235                 240
Tyr Gly Ile Val Met Gln Arg Trp Lys Pro Phe Gln Gln Asp Val Arg
                245                 250                 255
Cys Glu Val Glu Ile Val Leu Lys Ala Asn Tyr Ile Gln Val Asn Asn
            260                 265                 270
Glu Gln Ser Ser Gly Ile Ile Met Asp Glu Val Gln Lys Glu Phe
        275                 280                 285
Glu Asp Phe Trp Glu Tyr Tyr Lys Ser Asp Pro Phe Ala Gly Arg Asn
    290                 295                 300
Val Ile Leu Ala Ser Leu Cys Pro Gln Val Phe Gly Met Tyr Leu Val
305                 310                 315                 320
Lys Leu Ala Val Ala Met Val Leu Ala Gly Ile Gln Arg Thr Asp
                325                 330                 335
Ala Thr Gly Thr Arg Val Arg Gly Glu Ser His Leu Leu Leu Val Gly
            340                 345                 350
Asp Pro Gly Thr Gly Lys Ser Gln Phe Leu Lys Tyr Ala Ala Lys Ile
        355                 360                 365
Thr Pro Arg Ser Val Leu Thr Thr Gly Ile Gly Ser Thr Ser Ala Gly
    370                 375                 380
Leu Thr Val Thr Ala Val Lys Asp Ser Gly Glu Trp Asn Leu Glu Ala
385                 390                 395                 400
Gly Ala Leu Val Leu Ala Asp Ala Gly Leu Cys Cys Ile Asp Glu Phe
                405                 410                 415
Asn Ser Leu Lys Glu His Asp Arg Thr Ser Ile His Glu Ala Met Glu
            420                 425                 430
Gln Gln Thr Ile Ser Val Ala Lys Ala Gly Leu Val Cys Lys Leu Asn
        435                 440                 445
Thr Arg Thr Thr Ile Leu Ala Ala Thr Asn Pro Lys Gly Gln Tyr Asp
    450                 455                 460
Pro Gln Glu Ser Val Ser Val Asn Ile Ala Leu Gly Ser Pro Leu Leu
465                 470                 475                 480
Ser Arg Phe Asp Leu Ile Leu Val Leu Leu Asp Thr Lys Asn Glu Asp
                485                 490                 495
Trp Asp Arg Ile Ile Ser Ser Phe Ile Leu Glu Asn Lys Gly Tyr Pro
            500                 505                 510
```

```
Ser Lys Ser Glu Lys Leu Trp Ser Met Glu Lys Met Lys Thr Tyr Phe
        515                 520                 525
Cys Leu Ile Arg Asn Leu Gln Pro Thr Leu Ser Asp Val Gly Asn Gln
        530                 535                 540
Val Leu Leu Arg Tyr Tyr Gln Met Gln Arg Gln Ser Asp Cys Arg Asn
545                 550                 555                 560
Ala Ala Arg Thr Thr Ile Arg Leu Leu Glu Ser Leu Ile Arg Leu Ala
                565                 570                 575
Glu Ala His Ala Arg Leu Met Phe Arg Asp Thr Val Thr Leu Glu Asp
                580                 585                 590
Ala Ile Thr Val Val Ser Val Met Glu Ser Ser Met Gln Gly Gly Ala
        595                 600                 605
Leu Leu Gly Gly Val Asn Ala Leu His Thr Ser Phe Pro Glu Asn Pro
        610                 615                 620
Gly Glu Gln Tyr Gln Arg Gln Cys Glu Leu Ile Leu Glu Lys Leu Glu
625                 630                 635                 640
Leu Gln Ser Leu Leu Ser Glu Glu Leu Arg Arg Leu Glu Arg Leu Gln
                645                 650                 655
Asn Gln Ser Val His Gln Ser Gln Pro Arg Val Leu Glu Val Glu Thr
                660                 665                 670
Thr Pro Gly Ser Leu Arg Asn Gly Pro Gly Glu Glu Ser Asn Phe Arg
        675                 680                 685
Thr Ser Ser Gln Gln Glu Ile Asn Tyr Ser Thr His Ile Phe Ser Pro
        690                 695                 700
Gly Gly Ser Pro Glu Gly Ser Pro Val Leu Asp Pro Pro His Leu
705                 710                 715                 720
Glu Pro Asn Arg Ser Thr Ser Arg Lys His Ser Ala Gln His Lys Asn
                725                 730                 735
Asn Arg Asp Asp Ser Leu Asp Trp Phe Asp Phe Met Ala Thr His Gln
                740                 745                 750
Ser Glu Pro Lys Asn Thr Val Val Ser Pro His Pro Lys Thr Ser
        755                 760                 765
Gly Glu Asn Met Ala Ser Lys Ile Ser Asn Ser Thr Ser Gln Gly Lys
        770                 775                 780
Glu Lys Ser Glu Pro Gly Gln Arg Ser Lys Val Asp Ile Gly Leu Leu
785                 790                 795                 800
Pro Ser Pro Gly Glu Thr Gly Val Pro Trp Arg Ala Asp Asn Val Glu
                805                 810                 815
Ser Asn Lys Lys Lys Arg Leu Ala Leu Asp Ser Glu Ala Ala Val Ser
                820                 825                 830
Ala Asp Lys Pro Asp Ser Val Leu Thr His His Val Pro Arg Asn Leu
        835                 840                 845
Gln Lys Leu Cys Lys Glu Arg Ala Gln Lys Leu Cys Arg Asn Ser Thr
        850                 855                 860
Arg Val Pro Ala Gln Cys Thr Val Pro Ser His Pro Gln Ser Thr Pro
865                 870                 875                 880
Val His Ser Pro Asp Arg Arg Leu Asp Ser Pro Lys Arg Lys Arg Pro
                885                 890                 895
Lys Ser Leu Ala Gln Val Glu Glu Pro Ala Ile Glu Asn Val Lys Pro
                900                 905                 910
Pro Gly Ser Pro Val Ala Lys Leu Ala Lys Phe Thr Phe Lys Gln Lys
        915                 920                 925
Ser Lys Leu Ile His Ser Phe Glu Asp His Ser His Val Ser Pro Gly
```

```
                    930             935             940
Ala Thr Lys Ile Ala Val His Ser Pro Lys Ile Ser Gln Arg Arg Thr
945             950             955             960

Arg Arg Asp Ala Ala Leu Pro Val Lys Arg Pro Gly Lys Leu Thr Ser
            965             970             975

Thr Pro Gly Asn Gln Ile Ser Ser Gln Pro Gln Gly Glu Thr Lys Glu
                980             985             990

Val Ser Gln Gln Pro Pro Glu Lys His Gly Pro Arg Glu Lys Val Met
            995             1000            1005

Cys Ala Pro Glu Lys Arg Ile Ile Gln Pro Glu Leu Glu Leu Gly
    1010            1015            1020

Asn Glu Thr Gly Cys Ala His Leu Thr Cys Glu Gly Asp Lys Lys
    1025            1030            1035

Glu Glu Val Ser Gly Ser Asn Lys Ser Gly Lys Val His Ala Cys
    1040            1045            1050

Thr Leu Ala Arg Leu Ala Asn Phe Cys Phe Thr Pro Pro Ser Glu
    1055            1060            1065

Ser Lys Ser Lys Ser Pro Pro Glu Arg Lys Asn Arg Gly Glu
    1070            1075            1080

Arg Gly Pro Ser Ser Pro Thr Thr Thr Ala Pro Met Arg Val
    1085            1090            1095

Ser Lys Arg Lys Ser Phe Gln Leu Arg Gly Ser Thr Glu Lys Leu
    1100            1105            1110

Ile Val Ser Lys Glu Ser Leu Phe Thr Leu Pro Glu Leu Gly Asp
    1115            1120            1125

Glu Ala Phe Asp Cys Asp Trp Asp Glu Glu Met Arg Lys Lys Ser
    1130            1135            1140

<210> SEQ ID NO 3
<211> LENGTH: 3646
<212> TYPE: DNA
<213> ORGANISM: Homo sapiens
<220> FEATURE:
<221> NAME/KEY: CDS
<222> LOCATION: (1)..(2277)

<400> SEQUENCE: 3 ctg acg gta act gct gta aaa gac tca gga gaa tgg aat ttg gag gct   48
Leu Thr Val Thr Ala Val Lys Asp Ser Gly Glu Trp Asn Leu Glu Ala
1               5                   10                  15 ggg gca tta gtt ctt gca gat gcg ggc ctt tgc tgt att gat gag ttc   96
Gly Ala Leu Val Leu Ala Asp Ala Gly Leu Cys Cys Ile Asp Glu Phe
            20                  25                  30 aat agc ctc aaa gag cat gat agg acc agt atc cat gaa gca atg gag   144
Asn Ser Leu Lys Glu His Asp Arg Thr Ser Ile His Glu Ala Met Glu
        35                  40                  45 caa caa acc ata agt gtt gct aag gct ggc ctc gtg tgc aag ctg aac   192
Gln Gln Thr Ile Ser Val Ala Lys Ala Gly Leu Val Cys Lys Leu Asn
    50                  55                  60 aca agg acc acc atc ctg gca gca acg aac ccc aaa ggc cag tac gac   240
Thr Arg Thr Thr Ile Leu Ala Ala Thr Asn Pro Lys Gly Gln Tyr Asp
65                  70                  75                  80 ccc cag gag tcc gtg tct gtg aac att gcc ctc ggc agc cca ctc tta   288
Pro Gln Glu Ser Val Ser Val Asn Ile Ala Leu Gly Ser Pro Leu Leu
                85                  90                  95 agt cga ttt gac ctg atc ctg gtt ttg ctt gat acc aag aat gaa gac   336
Ser Arg Phe Asp Leu Ile Leu Val Leu Leu Asp Thr Lys Asn Glu Asp
            100                 105                 110
```

```
tgg gat cgt atc att tcc tcc ttt atc tta gaa aat aaa ggt tac cca      384
Trp Asp Arg Ile Ile Ser Ser Phe Ile Leu Glu Asn Lys Gly Tyr Pro
        115                 120                 125 agc aaa tca gag aag ctc tgg agc atg gaa aag atg aaa acc tat ttc      432
Ser Lys Ser Glu Lys Leu Trp Ser Met Glu Lys Met Lys Thr Tyr Phe
        130                 135                 140 tgc ctc ata agg aat ctg cag ccc aca ctg tct gat gtg ggc aat cag      480
Cys Leu Ile Arg Asn Leu Gln Pro Thr Leu Ser Asp Val Gly Asn Gln
145                 150                 155                 160 gtt ctt ctc cgg tac tac cag atg caa agg cag agt gat tgc cgg aac      528
Val Leu Leu Arg Tyr Tyr Gln Met Gln Arg Gln Ser Asp Cys Arg Asn
                165                 170                 175 gct gcc cgg acc acc att cgg ctg ttg gaa agc ttg ata cga tta gca      576
Ala Ala Arg Thr Thr Ile Arg Leu Leu Glu Ser Leu Ile Arg Leu Ala
            180                 185                 190 gaa gct cat gct cgc ctg atg ttt cgt gat act gta act ctg gaa gac      624
Glu Ala His Ala Arg Leu Met Phe Arg Asp Thr Val Thr Leu Glu Asp
        195                 200                 205 gct att acg gtg gtg tca gtc atg gag tcc tca atg cag gga ggt gca      672
Ala Ile Thr Val Val Ser Val Met Glu Ser Ser Met Gln Gly Gly Ala
    210                 215                 220 ctg cta gga ggt gtg aat gcc ctc cac act tcc ttt cct gaa aac cct      720
Leu Leu Gly Gly Val Asn Ala Leu His Thr Ser Phe Pro Glu Asn Pro
225                 230                 235                 240 gga gag cag tac cag aga cag tgt gaa ctt att ctg gaa aag cta gag      768
Gly Glu Gln Tyr Gln Arg Gln Cys Glu Leu Ile Leu Glu Lys Leu Glu
                245                 250                 255 ctg cag agc ctc ttg agt gaa gag ctt aga aga ctt gaa agg tta cag      816
Leu Gln Ser Leu Leu Ser Glu Glu Leu Arg Arg Leu Glu Arg Leu Gln
            260                 265                 270 aat cag agt gtg cac caa tcc caa cca cgg gta ttg gag gta gag act      864
Asn Gln Ser Val His Gln Ser Gln Pro Arg Val Leu Glu Val Glu Thr
        275                 280                 285 act cca gga tcc ttg aga aat ggt cca ggg gaa gaa tca aac ttc aga      912
Thr Pro Gly Ser Leu Arg Asn Gly Pro Gly Glu Glu Ser Asn Phe Arg
    290                 295                 300 act tca tca cag cag gaa atc aac tat agc aca cat atc ttc tct cct      960
Thr Ser Ser Gln Gln Glu Ile Asn Tyr Ser Thr His Ile Phe Ser Pro
305                 310                 315                 320 gga ggc agc ccc gag gga agc cca gtt cta gat ccc cca ccg cat ctg     1008
Gly Gly Ser Pro Glu Gly Ser Pro Val Leu Asp Pro Pro Pro His Leu
                325                 330                 335 gag cct aat aga tca aca agt agg aaa cat tca gct cag cac aaa aat     1056
Glu Pro Asn Arg Ser Thr Ser Arg Lys His Ser Ala Gln His Lys Asn
            340                 345                 350 aac aga gat gac agt tta gat tgg ttt gat ttc atg gca act cat cag     1104
Asn Arg Asp Asp Ser Leu Asp Trp Phe Asp Phe Met Ala Thr His Gln
        355                 360                 365 agt gaa cct aaa aac act gtt gtt gtg tct cct cat ccc aaa aca tct     1152
Ser Glu Pro Lys Asn Thr Val Val Val Ser Pro His Pro Lys Thr Ser
    370                 375                 380 gga gaa aat atg gct tcg aag atc tct aac agc aca tct cag ggt aag     1200
Gly Glu Asn Met Ala Ser Lys Ile Ser Asn Ser Thr Ser Gln Gly Lys
385                 390                 395                 400 gag aag agt gag cca ggc caa agg agc aaa gtg gac att ggg ttg ctt     1248
Glu Lys Ser Glu Pro Gly Gln Arg Ser Lys Val Asp Ile Gly Leu Leu
                405                 410                 415 cca tca cca gga gag aca ggt gtt cca tgg agg gca gac aat gtg gaa     1296
Pro Ser Pro Gly Glu Thr Gly Val Pro Trp Arg Ala Asp Asn Val Glu
            420                 425                 430
```

```
                                                        -continued agt aac aag aaa aaa agg cta gca cta gat tct gaa gca gca gtc tct    1344
Ser Asn Lys Lys Lys Arg Leu Ala Leu Asp Ser Glu Ala Ala Val Ser
        435                 440                 445 gct gat aaa cca gac tca gta ctg act cat cat gtc ccc agg aac ctg    1392
Ala Asp Lys Pro Asp Ser Val Leu Thr His His Val Pro Arg Asn Leu
    450                 455                 460 cag aag ctg tgc aaa gag agg gcc cag aag ttg tgc aga aat agc acc    1440
Gln Lys Leu Cys Lys Glu Arg Ala Gln Lys Leu Cys Arg Asn Ser Thr
465                 470                 475                 480 agg gtg cct gca cag tgc aca gtc cct tcc cat cct cag tcc act cct    1488
Arg Val Pro Ala Gln Cys Thr Val Pro Ser His Pro Gln Ser Thr Pro
                485                 490                 495 gta cat agc cca gac aga agg ctg gac tca ccc aaa aga aag aga ccg    1536
Val His Ser Pro Asp Arg Arg Leu Asp Ser Pro Lys Arg Lys Arg Pro
            500                 505                 510 aaa tcc ctt gcg caa gtg gaa gag cct gca att gaa aat gtt aag cct    1584
Lys Ser Leu Ala Gln Val Glu Glu Pro Ala Ile Glu Asn Val Lys Pro
        515                 520                 525 cca ggt tcc cct gtg gcc aaa ctg gca aaa ttt act ttc aag cag aag    1632
Pro Gly Ser Pro Val Ala Lys Leu Ala Lys Phe Thr Phe Lys Gln Lys
    530                 535                 540 tca aaa ctg atc cac tcc ttt gaa gat cac agc cat gtg tca cct ggt    1680
Ser Lys Leu Ile His Ser Phe Glu Asp His Ser His Val Ser Pro Gly
545                 550                 555                 560 gca act aaa ata gca gtt cat agt cct aaa att tcc cag cgt aga aca    1728
Ala Thr Lys Ile Ala Val His Ser Pro Lys Ile Ser Gln Arg Arg Thr
                565                 570                 575 aga aga gac gca gcc ttg ccg gtg aag cgt cca gga aag tta aca tct    1776
Arg Arg Asp Ala Ala Leu Pro Val Lys Arg Pro Gly Lys Leu Thr Ser
            580                 585                 590 acc cca gga aac cag atc tcc agt cag cca cag ggt gag aca aag gag    1824
Thr Pro Gly Asn Gln Ile Ser Ser Gln Pro Gln Gly Glu Thr Lys Glu
        595                 600                 605 gtg tcg cag cag cca cca gag aaa cac gga cca aga gag aag gtg atg    1872
Val Ser Gln Gln Pro Pro Glu Lys His Gly Pro Arg Glu Lys Val Met
610                 615                 620 tgt gcc cct gag aag agg att att cag cct gaa tta gag ctt ggg aac    1920
Cys Ala Pro Glu Lys Arg Ile Ile Gln Pro Glu Leu Glu Leu Gly Asn
625                 630                 635                 640 gag act ggg tgt gct cat ctt act tgt gag gga gac aaa aag gaa gag    1968
Glu Thr Gly Cys Ala His Leu Thr Cys Glu Gly Asp Lys Lys Glu Glu
                645                 650                 655 gtt tca ggc agt aat aaa agc ggc aag gtt cat gcc tgc aca tta gcc    2016
Val Ser Gly Ser Asn Lys Ser Gly Lys Val His Ala Cys Thr Leu Ala
            660                 665                 670 aga ttg gca aac ttc tgc ttt act ccc cca tcg gaa tcc aaa tca aaa    2064
Arg Leu Ala Asn Phe Cys Phe Thr Pro Pro Ser Glu Ser Lys Ser Lys
        675                 680                 685 tcc cct cct cct gaa agg aag aac cga ggt gag aga ggc cca agc tcc    2112
Ser Pro Pro Pro Glu Arg Lys Asn Arg Gly Glu Arg Gly Pro Ser Ser
    690                 695                 700 cct cct aca acc aca gct cca atg cgt gtc agt aaa agg aaa tct ttt    2160
Pro Pro Thr Thr Thr Ala Pro Met Arg Val Ser Lys Arg Lys Ser Phe
705                 710                 715                 720 cag ctc cgt ggg tcc acc gag aaa ctg att gtt tcc aaa gaa tcc ctc    2208
Gln Leu Arg Gly Ser Thr Glu Lys Leu Ile Val Ser Lys Glu Ser Leu
                725                 730                 735 ttc act tta cca gaa cta ggt gat gaa gca ttt gat tgt gac tgg gat    2256
Phe Thr Leu Pro Glu Leu Gly Asp Glu Ala Phe Asp Cys Asp Trp Asp
            740                 745                 750
```

```
gaa gag atg aga aaa aag tca tagttgggaa aagctttctg gtcaaatctc        2307
Glu Glu Met Arg Lys Lys Ser
        755 accttcttca actccacaga ggaccttcag gatatcaata tggtatttat aaatgtatag   2367 aacaattggc catattgagg atcactctga atactggctc ccccttaagg ctttctaatt   2427 tcaggttaat cttcatgact taaaaagttg tataatcagt tgaggtcagt gtgataccag   2487 cagctgagct gaattaatta tgttgtgctt aattttacaa atggagtact tgtattcctg   2547 ttcctgaagc tgtttctgtt ttttgttttg ttttgttttt aagggggaga ggttcttccc   2607 tagattaatt tcttctttca ttcactcagg aacaaatgtc aagaaggtag cactcataaa   2667 tctaacaagg cagatgaact cttttctact tttttttttt tttttgtat tttcacctgg    2727 aatgggctaa gtacagtgaa tataatcact tggatgattt gccaaaatca gactattttt   2787 ctagtattat ttttgtattg atttgtgtgg atcaggttaa atgtgactaa tgcttttctt   2847 tctttgagag gtatccttac aattccatga tgttcttaga gatctggcca ctggtcaaac   2907 agtacctttc tgaagtactg accttctgag ttgtcctttc tttcttgagc aacattttg    2967 tacttcagat tctttttttct cttggggcc taccttcaac caagtaaaat actgtgatta   3027 gaagaagaga gagtatgagc caggcacagt gactcactcc tgtagtccta gctactcggg   3087 gaggctgagg caggatgatt gcttaagccc aggagttcgg ggttacagtg agctgtggtc   3147 acaccactgt attccagcct gggtgacaga gtgagatcct gtctctaaaa ataaaataaa   3207 tgaagaagag agactatgtg gtagtctcaa tcaaacatca tgtctcatct acccagctgg   3267 ttaatatgga aatgtgattc ctactaagtt gtgattcact tgtctttaaa accaaggaaa   3327 ttatgtactg ttttttggtca gaatagataa cctcaagctt tgtctttcta tgtgctttta   3387 aaatcactta ttcctttgga ttctaataag ggttattagg attcagtaat tatggacttt   3447 ctcttctgaa gtgtgaattt gtaaactgat tgtttaattg tcagagggac ttttggacat   3507 agaatactca aaactatatg tattttgttt aattttcact tcattcaatt cacgcattga   3567 aaacaaattt agaaaatcca attttttctta agcatttaaa cgttctaaaa ttcactaata   3627 aaattttctg aaaaaattt                                                3646

<210> SEQ ID NO 4
<211> LENGTH: 759
<212> TYPE: PRT
<213> ORGANISM: Homo sapiens

<400> SEQUENCE: 4

Leu Thr Val Thr Ala Val Lys Asp Ser Gly Glu Trp Asn Leu Glu Ala
1               5                   10                  15

Gly Ala Leu Val Leu Ala Asp Ala Gly Leu Cys Cys Ile Asp Glu Phe
            20                  25                  30

Asn Ser Leu Lys Glu His Asp Arg Thr Ser Ile His Glu Ala Met Glu
        35                  40                  45

Gln Gln Thr Ile Ser Val Ala Lys Ala Gly Leu Val Cys Lys Leu Asn
    50                  55                  60

Thr Arg Thr Thr Ile Leu Ala Ala Thr Asn Pro Lys Gly Gln Tyr Asp
65                  70                  75                  80

Pro Gln Glu Ser Val Ser Val Asn Ile Ala Leu Gly Ser Pro Leu Leu
                85                  90                  95

Ser Arg Phe Asp Leu Ile Leu Val Leu Leu Asp Thr Lys Asn Glu Asp
            100                 105                 110

Trp Asp Arg Ile Ile Ser Ser Phe Ile Leu Glu Asn Lys Gly Tyr Pro
```

-continued

```
                115                 120                 125
    Ser Lys Ser Glu Lys Leu Trp Ser Met Glu Lys Met Lys Thr Tyr Phe
    130                 135                 140

Cys Leu Ile Arg Asn Leu Gln Pro Thr Leu Ser Asp Val Gly Asn Gln
    145                 150                 155                 160

Val Leu Leu Arg Tyr Tyr Gln Met Gln Arg Gln Ser Asp Cys Arg Asn
                    165                 170                 175

Ala Ala Arg Thr Thr Ile Arg Leu Leu Glu Ser Leu Ile Arg Leu Ala
                180                 185                 190

Glu Ala His Ala Arg Leu Met Phe Arg Asp Thr Val Thr Leu Glu Asp
                195                 200                 205

Ala Ile Thr Val Val Ser Val Met Glu Ser Ser Met Gln Gly Gly Ala
    210                 215                 220

Leu Leu Gly Gly Val Asn Ala Leu His Thr Ser Phe Pro Glu Asn Pro
    225                 230                 235                 240

Gly Glu Gln Tyr Gln Arg Gln Cys Glu Leu Ile Leu Glu Lys Leu Glu
                    245                 250                 255

Leu Gln Ser Leu Leu Ser Glu Glu Leu Arg Arg Leu Glu Arg Leu Gln
                260                 265                 270

Asn Gln Ser Val His Gln Ser Gln Pro Arg Val Leu Glu Val Glu Thr
                275                 280                 285

Thr Pro Gly Ser Leu Arg Asn Gly Pro Gly Glu Ser Asn Phe Arg
    290                 295                 300

Thr Ser Ser Gln Gln Glu Ile Asn Tyr Ser Thr His Ile Phe Ser Pro
    305                 310                 315                 320

Gly Gly Ser Pro Glu Gly Ser Pro Val Leu Asp Pro Pro His Leu
                    325                 330                 335

Glu Pro Asn Arg Ser Thr Ser Arg Lys His Ser Ala Gln His Lys Asn
                340                 345                 350

Asn Arg Asp Asp Ser Leu Asp Trp Phe Asp Phe Met Ala Thr His Gln
                355                 360                 365

Ser Glu Pro Lys Asn Thr Val Val Ser Pro His Pro Lys Thr Ser
    370                 375                 380

Gly Glu Asn Met Ala Ser Lys Ile Ser Asn Ser Thr Ser Gln Gly Lys
    385                 390                 395                 400

Glu Lys Ser Glu Pro Gly Gln Arg Ser Lys Val Asp Ile Gly Leu Leu
                    405                 410                 415

Pro Ser Pro Gly Glu Thr Gly Val Pro Trp Arg Ala Asp Asn Val Glu
                420                 425                 430

Ser Asn Lys Lys Lys Arg Leu Ala Leu Asp Ser Glu Ala Ala Val Ser
                435                 440                 445

Ala Asp Lys Pro Asp Ser Val Leu Thr His His Val Pro Arg Asn Leu
    450                 455                 460

Gln Lys Leu Cys Lys Glu Arg Ala Gln Lys Leu Cys Arg Asn Ser Thr
    465                 470                 475                 480

Arg Val Pro Ala Gln Cys Thr Val Pro Ser His Pro Gln Ser Thr Pro
                    485                 490                 495

Val His Ser Pro Asp Arg Arg Leu Asp Ser Pro Lys Arg Lys Arg Pro
                500                 505                 510

Lys Ser Leu Ala Gln Val Glu Glu Pro Ala Ile Glu Asn Val Lys Pro
                515                 520                 525

Pro Gly Ser Pro Val Ala Lys Leu Ala Lys Phe Thr Phe Lys Gln Lys
    530                 535                 540
```

-continued

```
Ser Lys Leu Ile His Ser Phe Glu Asp His Ser His Val Ser Pro Gly
545                 550                 555                 560

Ala Thr Lys Ile Ala Val His Ser Pro Lys Ile Ser Gln Arg Arg Thr
                565                 570                 575

Arg Arg Asp Ala Ala Leu Pro Val Lys Arg Pro Gly Lys Leu Thr Ser
            580                 585                 590

Thr Pro Gly Asn Gln Ile Ser Ser Gln Pro Gln Gly Glu Thr Lys Glu
        595                 600                 605

Val Ser Gln Gln Pro Pro Glu Lys His Gly Pro Arg Glu Lys Val Met
    610                 615                 620

Cys Ala Pro Glu Lys Arg Ile Ile Gln Pro Leu Glu Leu Gly Asn
625                 630                 635                 640

Glu Thr Gly Cys Ala His Leu Thr Cys Glu Gly Asp Lys Lys Glu Glu
                645                 650                 655

Val Ser Gly Ser Asn Lys Ser Gly Lys Val His Ala Cys Thr Leu Ala
            660                 665                 670

Arg Leu Ala Asn Phe Cys Phe Thr Pro Pro Ser Glu Ser Lys Ser Lys
        675                 680                 685

Ser Pro Pro Pro Glu Arg Lys Asn Arg Gly Glu Arg Gly Pro Ser Ser
    690                 695                 700

Pro Pro Thr Thr Thr Ala Pro Met Arg Val Ser Lys Arg Lys Ser Phe
705                 710                 715                 720

Gln Leu Arg Gly Ser Thr Glu Lys Leu Ile Val Ser Lys Glu Ser Leu
                725                 730                 735

Phe Thr Leu Pro Glu Leu Gly Asp Glu Ala Phe Asp Cys Asp Trp Asp
            740                 745                 750

Glu Glu Met Arg Lys Lys Ser
        755
```

```
<210> SEQ ID NO 5
<211> LENGTH: 1152
<212> TYPE: DNA
<213> ORGANISM: Homo sapiens
<220> FEATURE:
<221> NAME/KEY: CDS
<222> LOCATION: (1)..(1152)

<400> SEQUENCE: 5
```

```
atg aat agc gat caa gtt aca ctg gtt ggt caa gtg ttt gag tca tat      48
Met Asn Ser Asp Gln Val Thr Leu Val Gly Gln Val Phe Glu Ser Tyr
1               5                   10                  15 gtt tcg gaa tac cat aag aat gat att ctt cta atc ttg aag gaa agg      96
Val Ser Glu Tyr His Lys Asn Asp Ile Leu Leu Ile Leu Lys Glu Arg
                20                  25                  30 gat gaa gat gct cat tac cca gtt gtt gtt aat gcc atg act ctg ttt     144
Asp Glu Asp Ala His Tyr Pro Val Val Val Asn Ala Met Thr Leu Phe
            35                  40                  45 gag acc aac atg gaa atc ggg gaa tat ttc aac atg ttc ccc agt gaa     192
Glu Thr Asn Met Glu Ile Gly Glu Tyr Phe Asn Met Phe Pro Ser Glu
        50                  55                  60 gtg ctt aca att ttt gat agt gca ctg cga agg tca gcc ttg aca att     240
Val Leu Thr Ile Phe Asp Ser Ala Leu Arg Arg Ser Ala Leu Thr Ile
65                  70                  75                  80 ctc cag tcc ctt tct cag cct gag gct gtt tcc atg aaa cag aat ctt     288
Leu Gln Ser Leu Ser Gln Pro Glu Ala Val Ser Met Lys Gln Asn Leu
                85                  90                  95 cat gcc agg ata tca ggt ttg cct gtc tgt cct gag ctg gtg agg gaa     336
His Ala Arg Ile Ser Gly Leu Pro Val Cys Pro Glu Leu Val Arg Glu
            100                 105                 110
```

```
cac ata cct aaa acc aag gat gtg gga cac ttt tta tct gtc act ggg       384
His Ile Pro Lys Thr Lys Asp Val Gly His Phe Leu Ser Val Thr Gly
        115                 120                 125 aca gtg att cga aca agt ctg gtg aag gtt ctg gag ttt gag cgg gat       432
Thr Val Ile Arg Thr Ser Leu Val Lys Val Leu Glu Phe Glu Arg Asp
    130                 135                 140 tac atg tgt aac aaa tgc aag cat gtg ttt gtg atc aag gct gac ttt       480
Tyr Met Cys Asn Lys Cys Lys His Val Phe Val Ile Lys Ala Asp Phe
145                 150                 155                 160 gag cag tat tac acc ttt tgc cgg cca tcc tcg tgt ccc agc ttg gag       528
Glu Gln Tyr Tyr Thr Phe Cys Arg Pro Ser Ser Cys Pro Ser Leu Glu
                165                 170                 175 agc tgt gat tcc tct aaa ttc act tgc ctc tca ggc ttg tct tcg tct       576
Ser Cys Asp Ser Ser Lys Phe Thr Cys Leu Ser Gly Leu Ser Ser Ser
            180                 185                 190 cca acc agg tgt aga gat tac cag gaa atc aaa att cag gaa cag gtt       624
Pro Thr Arg Cys Arg Asp Tyr Gln Glu Ile Lys Ile Gln Glu Gln Val
        195                 200                 205 caa agg cta tct gtt gga agt att cca cga tct atg aag gtt att ctg       672
Gln Arg Leu Ser Val Gly Ser Ile Pro Arg Ser Met Lys Val Ile Leu
    210                 215                 220 gaa gat gac tta gtg gat agt tgc aaa tct ggt gat gac ctc act att       720
Glu Asp Asp Leu Val Asp Ser Cys Lys Ser Gly Asp Asp Leu Thr Ile
225                 230                 235                 240 tac ggg att gta atg caa cgg tgg aag ccc ttt cag caa gat gtg cgc       768
Tyr Gly Ile Val Met Gln Arg Trp Lys Pro Phe Gln Gln Asp Val Arg
                245                 250                 255 tgt gaa gtg gag ata gtc ctg aaa gca aat tac atc caa gta aat aat       816
Cys Glu Val Glu Ile Val Leu Lys Ala Asn Tyr Ile Gln Val Asn Asn
            260                 265                 270 gag cag tcc tca ggg atc atc atg gat gag gag gtc caa aag gaa ttc       864
Glu Gln Ser Ser Gly Ile Ile Met Asp Glu Glu Val Gln Lys Glu Phe
        275                 280                 285 gaa gat ttt tgg gaa tac tat aag agc gat ccc ttt gca gga agg aat       912
Glu Asp Phe Trp Glu Tyr Tyr Lys Ser Asp Pro Phe Ala Gly Arg Asn
    290                 295                 300 gta ata ttg gct agc ttg tgc cct caa gtg ttt gga atg tat cta gta       960
Val Ile Leu Ala Ser Leu Cys Pro Gln Val Phe Gly Met Tyr Leu Val
305                 310                 315                 320 aag ctt gct gtg gcc atg gtg ctg gct ggt ggg att caa agg act gat      1008
Lys Leu Ala Val Ala Met Val Leu Ala Gly Gly Ile Gln Arg Thr Asp
                325                 330                 335 gct aca gga aca cgg gtc aga gga gaa tct cat ctt tta ttg gtt ggg      1056
Ala Thr Gly Thr Arg Val Arg Gly Glu Ser His Leu Leu Leu Val Gly
            340                 345                 350 gat cct ggc aca ggg aaa tct cag ttc ctc aaa tat gca gca aag att      1104
Asp Pro Gly Thr Gly Lys Ser Gln Phe Leu Lys Tyr Ala Ala Lys Ile
        355                 360                 365 aca cca aga tct gtg ctg acc aca gga att gga tct act agt gca ggt      1152
Thr Pro Arg Ser Val Leu Thr Thr Gly Ile Gly Ser Thr Ser Ala Gly
    370                 375                 380

<210> SEQ ID NO 6
<211> LENGTH: 384
<212> TYPE: PRT
<213> ORGANISM: Homo sapiens

<400> SEQUENCE: 6

Met Asn Ser Asp Gln Val Thr Leu Val Gly Gln Val Phe Glu Ser Tyr
1               5                   10                  15
```

```
Val Ser Glu Tyr His Lys Asn Asp Ile Leu Ile Leu Lys Glu Arg
         20                  25                  30

Asp Glu Asp Ala His Tyr Pro Val Val Asn Ala Met Thr Leu Phe
         35                  40                  45

Glu Thr Asn Met Glu Ile Gly Glu Tyr Phe Asn Met Phe Pro Ser Glu
 50                  55                  60

Val Leu Thr Ile Phe Asp Ser Ala Leu Arg Arg Ser Ala Leu Thr Ile
 65                  70                  75                  80

Leu Gln Ser Leu Ser Gln Pro Glu Ala Val Ser Met Lys Gln Asn Leu
                 85                  90                  95

His Ala Arg Ile Ser Gly Leu Pro Val Cys Pro Glu Leu Val Arg Glu
            100                 105                 110

His Ile Pro Lys Thr Lys Asp Val Gly His Phe Leu Ser Val Thr Gly
            115                 120                 125

Thr Val Ile Arg Thr Ser Leu Val Lys Val Leu Glu Phe Glu Arg Asp
    130                 135                 140

Tyr Met Cys Asn Lys Cys Lys His Val Phe Val Ile Lys Ala Asp Phe
145                 150                 155                 160

Glu Gln Tyr Tyr Thr Phe Cys Arg Pro Ser Ser Cys Pro Ser Leu Glu
                165                 170                 175

Ser Cys Asp Ser Ser Lys Phe Thr Cys Leu Ser Gly Leu Ser Ser Ser
            180                 185                 190

Pro Thr Arg Cys Arg Asp Tyr Gln Glu Ile Lys Ile Gln Glu Gln Val
        195                 200                 205

Gln Arg Leu Ser Val Gly Ser Ile Pro Arg Ser Met Lys Val Ile Leu
    210                 215                 220

Glu Asp Asp Leu Val Asp Ser Cys Lys Ser Gly Asp Asp Leu Thr Ile
225                 230                 235                 240

Tyr Gly Ile Val Met Gln Arg Trp Lys Pro Phe Gln Gln Asp Val Arg
                245                 250                 255

Cys Glu Val Glu Ile Val Leu Lys Ala Asn Tyr Ile Gln Val Asn Asn
            260                 265                 270

Glu Gln Ser Ser Gly Ile Ile Met Asp Glu Glu Val Gln Lys Glu Phe
        275                 280                 285

Glu Asp Phe Trp Glu Tyr Tyr Lys Ser Asp Pro Phe Ala Gly Arg Asn
    290                 295                 300

Val Ile Leu Ala Ser Leu Cys Pro Gln Val Phe Gly Met Tyr Leu Val
305                 310                 315                 320

Lys Leu Ala Val Ala Met Val Leu Ala Gly Gly Ile Gln Arg Thr Asp
                325                 330                 335

Ala Thr Gly Thr Arg Val Arg Gly Glu Ser His Leu Leu Leu Val Gly
            340                 345                 350

Asp Pro Gly Thr Gly Lys Ser Gln Phe Leu Lys Tyr Ala Ala Lys Ile
        355                 360                 365

Thr Pro Arg Ser Val Leu Thr Thr Gly Ile Gly Ser Thr Ser Ala Gly
    370                 375                 380

<210> SEQ ID NO 7
<211> LENGTH: 3873
<212> TYPE: DNA
<213> ORGANISM: Mus musculus
<220> FEATURE:
<221> NAME/KEY: CDS
<222> LOCATION: (1)..(3870)

<400> SEQUENCE: 7
```

```
atg gat cag aga act aca cga aat gga aaa tat tgt gac gtg gaa ccg      48
Met Asp Gln Arg Thr Thr Arg Asn Gly Lys Tyr Cys Asp Val Glu Pro
1               5                   10                  15 gtg tcc cgc tca aac ccc gcc cca tgc ctc cga gac ccg ccc ctc aga      96
Val Ser Arg Ser Asn Pro Ala Pro Cys Leu Arg Asp Pro Pro Leu Arg
            20                  25                  30 cgt ctt gtc cgg ccc aaa ccc cgc ctc cag ctc ccc gag tcc cgc ctc     144
Arg Leu Val Arg Pro Lys Pro Arg Leu Gln Leu Pro Glu Ser Arg Leu
        35                  40                  45 tct ccc tgc tcc cgc ctc ccg ctc gca gac tcc agc gtc cgt cct ggc     192
Ser Pro Cys Ser Arg Leu Pro Leu Ala Asp Ser Ser Val Arg Pro Gly
    50                  55                  60 gcg cgc ccg cct gcg tcc gca ccc gga aga agc ccc agc ggc cgg aaa     240
Ala Arg Pro Pro Ala Ser Ala Pro Gly Arg Ser Pro Ser Gly Arg Lys
65                  70                  75                  80 gtt gag gca gtg cgc ggc tcg ggg tcc gcg gga agc tca agt cct tca     288
Val Glu Ala Val Arg Gly Ser Gly Ser Ala Gly Ser Ser Ser Pro Ser
                85                  90                  95 gag gcc gag cga gag cag cgc gaa gaa gcc tgc gcg ccc ccg cgc aag     336
Glu Ala Glu Arg Glu Gln Arg Glu Glu Ala Cys Ala Pro Pro Arg Lys
            100                 105                 110 gcg gcc ccc tcg agc ggc cgc gcg cac gcc ccg ccc cct cca acg ccg     384
Ala Ala Pro Ser Ser Gly Arg Ala His Ala Pro Pro Pro Pro Thr Pro
        115                 120                 125 cgc ggg tcg ggc tgg ggc gac cac ggc cgc agc gcg gtc ccg gcg acc     432
Arg Gly Ser Gly Trp Gly Asp His Gly Arg Ser Ala Val Pro Ala Thr
    130                 135                 140 aag aca gtg cgt gtt gag ccc tac cca ccc ttc aag atg aat agt gag     480
Lys Thr Val Arg Val Glu Pro Tyr Pro Pro Phe Lys Met Asn Ser Glu
145                 150                 155                 160 cag gtc acc ctg gtg ggt cag gtg ttt gag tcc tat gtt tca gag tac     528
Gln Val Thr Leu Val Gly Gln Val Phe Glu Ser Tyr Val Ser Glu Tyr
                165                 170                 175 cat aag aac gat att ctt ctg atc ctg aaa gaa aga gat gaa gat gct     576
His Lys Asn Asp Ile Leu Leu Ile Leu Lys Glu Arg Asp Glu Asp Ala
            180                 185                 190 cac tac ccg gtt gtg gtt aat gct atg agc ctt ttc gag acc aac atg     624
His Tyr Pro Val Val Val Asn Ala Met Ser Leu Phe Glu Thr Asn Met
        195                 200                 205 gaa att ggg gac tat ttc acc gtg ttc ccc aat gaa gta cta aca gtt     672
Glu Ile Gly Asp Tyr Phe Thr Val Phe Pro Asn Glu Val Leu Thr Val
    210                 215                 220 ttt gac agt gca ctt cga agg tca gcc ttg gca att ctg cag tcc ctt     720
Phe Asp Ser Ala Leu Arg Arg Ser Ala Leu Ala Ile Leu Gln Ser Leu
225                 230                 235                 240 cct gag acg gag ggg tta tcc atg aag cag aat ctt cat gcc agg ata     768
Pro Glu Thr Glu Gly Leu Ser Met Lys Gln Asn Leu His Ala Arg Ile
                245                 250                 255 tca ggt ttg cct gtt tgt cca gaa ctg gtc agg gaa cac att ccc aaa     816
Ser Gly Leu Pro Val Cys Pro Glu Leu Val Arg Glu His Ile Pro Lys
            260                 265                 270 acc aag gat gtg gga cac ttc tta tct gtc act ggg aca gtg atc cga     864
Thr Lys Asp Val Gly His Phe Leu Ser Val Thr Gly Thr Val Ile Arg
        275                 280                 285 acg agt ctg gtg aag gtc ttg gag ttc gag cgg gat tac atg tgt aac     912
Thr Ser Leu Val Lys Val Leu Glu Phe Glu Arg Asp Tyr Met Cys Asn
    290                 295                 300 aaa tgc aag cat gtg ttc atg gtg gag gca gac ttc gag cag tat tac     960
Lys Cys Lys His Val Phe Met Val Glu Ala Asp Phe Glu Gln Tyr Tyr
305                 310                 315                 320
```

| | | |
|---|---|---|
| acc ttc agt cgg cca tcg tca tgt cca agt tta gcc agc tgt gac tcc<br>Thr Phe Ser Arg Pro Ser Ser Cys Pro Ser Leu Ala Ser Cys Asp Ser<br>     325       330       335 | | 1008 |
| tca aaa ttc tct tgc ctc tca gac ttg tct tca tct cca gcc aga tgt<br>Ser Lys Phe Ser Cys Leu Ser Asp Leu Ser Ser Ser Pro Ala Arg Cys<br>   340       345       350 | | 1056 |
| cgg gat tac cag gaa atc aaa att cag gag cag gtg caa agg ctg tct<br>Arg Asp Tyr Gln Glu Ile Lys Ile Gln Glu Gln Val Gln Arg Leu Ser<br>     355       360       365 | | 1104 |
| gtt gga agt atc cca cgg tct atg aaa gtt att ctg gaa gat gac cta<br>Val Gly Ser Ile Pro Arg Ser Met Lys Val Ile Leu Glu Asp Asp Leu<br>370       375       380 | | 1152 |
| gtt gac agt tgc aaa tct gga gat gac ctc acc atc tat ggg gtt gta<br>Val Asp Ser Cys Lys Ser Gly Asp Asp Leu Thr Ile Tyr Gly Val Val<br>385       390       395       400 | | 1200 |
| atg caa cgg tgg aaa ccc ttt cag cga gat gta cgc tgt gaa gtt gag<br>Met Gln Arg Trp Lys Pro Phe Gln Arg Asp Val Arg Cys Glu Val Glu<br>       405       410       415 | | 1248 |
| att gtc ttg aaa gcc aac tat gtc caa gtg aat aat gag caa tcc tcg<br>Ile Val Leu Lys Ala Asn Tyr Val Gln Val Asn Asn Glu Gln Ser Ser<br>     420       425       430 | | 1296 |
| ggg atg gtc atg gat gag gac act cga aaa gaa ttt gaa gac ttc tgg<br>Gly Met Val Met Asp Glu Asp Thr Arg Lys Glu Phe Glu Asp Phe Trp<br>       435       440       445 | | 1344 |
| gaa cac tat aag agt gac ccc ttt gca ggg agg aat gaa ata ttg gcc<br>Glu His Tyr Lys Ser Asp Pro Phe Ala Gly Arg Asn Glu Ile Leu Ala<br>   450       455       460 | | 1392 |
| agc ttg tgt cct caa gtt ttt ggg atg tat cta gtg aag ctt gct gtg<br>Ser Leu Cys Pro Gln Val Phe Gly Met Tyr Leu Val Lys Leu Ala Val<br>465       470       475       480 | | 1440 |
| gcc atg gta ctg gct ggt gga att caa aga act gat gct gca gga acc<br>Ala Met Val Leu Ala Gly Gly Ile Gln Arg Thr Asp Ala Ala Gly Thr<br>       485       490       495 | | 1488 |
| agg gtt aga ggg gaa tct cac ctt tta ttg gtt ggg gat cct ggc aca<br>Arg Val Arg Gly Glu Ser His Leu Leu Leu Val Gly Asp Pro Gly Thr<br>     500       505       510 | | 1536 |
| ggg aaa tca caa ttc ctt aaa tat gca gca aag att acc cca agg tcc<br>Gly Lys Ser Gln Phe Leu Lys Tyr Ala Ala Lys Ile Thr Pro Arg Ser<br>     515       520       525 | | 1584 |
| gtt ttg acc aca gga att gga tct act agt gca ggt ctg acc gtg aca<br>Val Leu Thr Thr Gly Ile Gly Ser Thr Ser Ala Gly Leu Thr Val Thr<br>530       535       540 | | 1632 |
| gct gtc aaa gac tca gga gaa tgg aat cta gag gct ggg gct ttg gtg<br>Ala Val Lys Asp Ser Gly Glu Trp Asn Leu Glu Ala Gly Ala Leu Val<br>545       550       555       560 | | 1680 |
| ctt gca gat gct ggt ctc tgc tgt att gac gaa ttt aac agc ctc aaa<br>Leu Ala Asp Ala Gly Leu Cys Cys Ile Asp Glu Phe Asn Ser Leu Lys<br>       565       570       575 | | 1728 |
| gaa cat gac agg aca agc atc cat gaa gca atg gag caa caa acc ata<br>Glu His Asp Arg Thr Ser Ile His Glu Ala Met Glu Gln Gln Thr Ile<br>     580       585       590 | | 1776 |
| agt gtt gct aag gct ggc ctt gtt tgt aag ctg aac aca agg acc acc<br>Ser Val Ala Lys Ala Gly Leu Val Cys Lys Leu Asn Thr Arg Thr Thr<br>   595       600       605 | | 1824 |
| atc ctg gca gca act aac ccc aaa ggc cag tat gac ccc aag gag tct<br>Ile Leu Ala Ala Thr Asn Pro Lys Gly Gln Tyr Asp Pro Lys Glu Ser<br>       610       615       620 | | 1872 |
| gtg tct gtg aac att gcc ctc ggg agc cca ctc tta agt cga ttt gac<br>Val Ser Val Asn Ile Ala Leu Gly Ser Pro Leu Leu Ser Arg Phe Asp<br>625       630       635       640 | | 1920 |

```
ctt gtc ctg gtt ttg ctc gac act agg aat gaa gac tgg gat cgt atc    1968
Leu Val Leu Val Leu Leu Asp Thr Arg Asn Glu Asp Trp Asp Arg Ile
            645                 650                 655 att tct tcc ttt atc tta gaa aat aaa ggt tat cca agc aaa tca gag    2016
Ile Ser Ser Phe Ile Leu Glu Asn Lys Gly Tyr Pro Ser Lys Ser Glu
            660                 665                 670 aat ctg tgg agc atg gag aag atg aaa acc tac ttc tgc ctc att cgg    2064
Asn Leu Trp Ser Met Glu Lys Met Lys Thr Tyr Phe Cys Leu Ile Arg
        675                 680                 685 aat ctc cac ccc aca ctg tct gaa gtg agc aat caa gtc ctc ctt cga    2112
Asn Leu His Pro Thr Leu Ser Glu Val Ser Asn Gln Val Leu Leu Arg
        690                 695                 700 tac tac caa atg caa agg cag agt gat tcc cgg aat gca gcc cgg aca    2160
Tyr Tyr Gln Met Gln Arg Gln Ser Asp Ser Arg Asn Ala Ala Arg Thr
705                 710                 715                 720 acc atc cgc ctg tta gaa agc ttg atc cga tta gca gaa gct cac gct    2208
Thr Ile Arg Leu Leu Glu Ser Leu Ile Arg Leu Ala Glu Ala His Ala
            725                 730                 735 cgc ctg atg ttc cgc agt gcc gtg act ctg gaa gat gcc gtt aca gct    2256
Arg Leu Met Phe Arg Ser Ala Val Thr Leu Glu Asp Ala Val Thr Ala
            740                 745                 750 gta tct gtg atg gag tct tca atg cag gga ggt gct ctg cta gga ggt    2304
Val Ser Val Met Glu Ser Ser Met Gln Gly Gly Ala Leu Leu Gly Gly
            755                 760                 765 gtg aat gct ctc cac act tcc ttc cct gaa aac ccc cgt gca cag tac    2352
Val Asn Ala Leu His Thr Ser Phe Pro Glu Asn Pro Arg Ala Gln Tyr
770                 775                 780 cag agg cag tgt gaa ctc att ctg gaa aag ctg gaa ctc cag ggc ctc    2400
Gln Arg Gln Cys Glu Leu Ile Leu Glu Lys Leu Glu Leu Gln Gly Leu
785                 790                 795                 800 ttg cag gaa gaa ctt cga aga ctg gaa agg tta cag aat gag agt gta    2448
Leu Gln Glu Glu Leu Arg Arg Leu Glu Arg Leu Gln Asn Glu Ser Val
                805                 810                 815 cac caa tgc cag tca cat tca cta gag gag gag gtg gct cca ggt tcc    2496
His Gln Cys Gln Ser His Ser Leu Glu Glu Glu Val Ala Pro Gly Ser
            820                 825                 830 tgc aga aat gat ccc agg gac aag cca agg ctc agg act tca aca cag    2544
Cys Arg Asn Asp Pro Arg Asp Lys Pro Arg Leu Arg Thr Ser Thr Gln
        835                 840                 845 cag gaa cag agc tgt agc tgg agt tcc aca gag aga tct ggt gca gac    2592
Gln Glu Gln Ser Cys Ser Trp Ser Ser Thr Glu Arg Ser Gly Ala Asp
        850                 855                 860 tcc ccg cct ggt cca ggg ctt aat aga cca aca agt tgt aac aac tca    2640
Ser Pro Pro Gly Pro Gly Leu Asn Arg Pro Thr Ser Cys Asn Asn Ser
865                 870                 875                 880 gct gag aac aga gat ggc aga ggt gac ggt tta gac tgg ttg gac ccc    2688
Ala Glu Asn Arg Asp Gly Arg Gly Asp Gly Leu Asp Trp Leu Asp Pro
                885                 890                 895 aca tca agt cct gag att gca cca gaa agc act att gtg tct ccc aat    2736
Thr Ser Ser Pro Glu Ile Ala Pro Glu Ser Thr Ile Val Ser Pro Asn
            900                 905                 910 gtg aaa aca act gag aaa aat gtg aat ttg aaa atc tcc aac aat aaa    2784
Val Lys Thr Thr Glu Lys Asn Val Asn Leu Lys Ile Ser Asn Asn Lys
            915                 920                 925 tct cag ggc aag gag aag cat ggg cca cag caa aga agc aaa tta tta    2832
Ser Gln Gly Lys Glu Lys His Gly Pro Gln Gln Arg Ser Lys Leu Leu
        930                 935                 940 gaa gct gga cat ctt cca tca tca gga gcc atg aat gcc ccc tta cgg    2880
Glu Ala Gly His Leu Pro Ser Ser Gly Ala Met Asn Ala Pro Leu Arg
945                 950                 955                 960
```

```
tct cac ggt gtt aag cgt aca aag gca agt cag gca gtg gtt gta tct    2928
Ser His Gly Val Lys Arg Thr Lys Ala Ser Gln Ala Val Val Val Ser
            965                 970                 975 gaa gca gga cgg ggt gat gaa gaa gac tct gtg ccc cga aga ctc ccc    2976
Glu Ala Gly Arg Gly Asp Glu Glu Asp Ser Val Pro Arg Arg Leu Pro
            980                 985                 990 aag ctg ctg aag gag ggg tca cag aat gtg tgc aga agc aca acc aga   3024
Lys Leu Leu Lys Glu Gly Ser Gln Asn Val Cys Arg Ser Thr Thr Arg
            995                 1000                1005 gtg cga cca ctg cca ccc act gtc cct ctg tcc ctg tct atc cct        3069
Val Arg Pro Leu Pro Pro Thr Val Pro Leu Ser Leu Ser Ile Pro
        1010                1015                1020 tca cct ggg tca gga aaa aga tca gga aca ccc aaa aga aag aga        3114
Ser Pro Gly Ser Gly Lys Arg Ser Gly Thr Pro Lys Arg Lys Arg
        1025                1030                1035 cgg aaa tct gct cag gtg gaa gag cct gaa cct gaa ggt atg gag        3159
Arg Lys Ser Ala Gln Val Glu Glu Pro Glu Pro Glu Gly Met Glu
        1040                1045                1050 act cca aca gta aag ctg gcc aaa ttc aca ttt aaa cag aag aca        3204
Thr Pro Thr Val Lys Leu Ala Lys Phe Thr Phe Lys Gln Lys Thr
        1055                1060                1065 aaa ctg acc cac tcc ccc gaa ggc caa ggc ccc ata cct ccc agt        3249
Lys Leu Thr His Ser Pro Glu Gly Gln Gly Pro Ile Pro Pro Ser
        1070                1075                1080 gct agt gaa ata gca gtt gac agt tct aaa att ccc caa caa aga        3294
Ala Ser Glu Ile Ala Val Asp Ser Ser Lys Ile Pro Gln Gln Arg
        1085                1090                1095 aca aga aga gaa gca gct gtg cct gtg gta gcg cca gga aag tcg        3339
Thr Arg Arg Glu Ala Ala Val Pro Val Val Ala Pro Gly Lys Ser
        1100                1105                1110 aca tcc acc tca gga gac aga tgc tct gac cag ctg cac gga aag        3384
Thr Ser Thr Ser Gly Asp Arg Cys Ser Asp Gln Leu His Gly Lys
        1115                1120                1125 aca aag gag ctc tca agg cag cca cca gac agt aat cca cca aga        3429
Thr Lys Glu Leu Ser Arg Gln Pro Pro Asp Ser Asn Pro Pro Arg
        1130                1135                1140 gag gag agg gaa cag ggc ccc aaa aga agg gtt att cag ccc aaa        3474
Glu Glu Arg Glu Gln Gly Pro Lys Arg Arg Val Ile Gln Pro Lys
        1145                1150                1155 ccg gag ctt ggg aac cag gct ggg cat tcg cat cta gcc tgt gag        3519
Pro Glu Leu Gly Asn Gln Ala Gly His Ser His Leu Ala Cys Glu
        1160                1165                1170 aaa gac aga aag gaa ggg gtt tcc tgc ggt aat aaa agc agc aag        3564
Lys Asp Arg Lys Glu Gly Val Ser Cys Gly Asn Lys Ser Ser Lys
        1175                1180                1185 gtt cat gct ggc acc ata gcc aga ctg gca agc ttc tcc ttc act        3609
Val His Ala Gly Thr Ile Ala Arg Leu Ala Ser Phe Ser Phe Thr
        1190                1195                1200 tcc cca tca gaa tcc aaa tcg gaa tcc ctc cct cct gaa agg aag        3654
Ser Pro Ser Glu Ser Lys Ser Glu Ser Leu Pro Pro Glu Arg Lys
        1205                1210                1215 gac agc agg gac agc agg gac agc agg gac agc agg gac agg tgc        3699
Asp Ser Arg Asp Ser Arg Asp Ser Arg Asp Ser Arg Asp Arg Cys
        1220                1225                1230 cac agc cct cct gcg acc aca gct cca gtg ctc ggc cag caa agg        3744
His Ser Pro Pro Ala Thr Thr Ala Pro Val Leu Gly Gln Gln Arg
        1235                1240                1245 cag act ttc cag ctg cag cag ccc aca gag aga gcg aat ctt tcc        3789
Gln Thr Phe Gln Leu Gln Gln Pro Thr Glu Arg Ala Asn Leu Ser
        1250                1255                1260
```

```
acc  ctc  tcc  ctc  ttc  act  ctg  tcg  gaa  cta  gat  gac  gaa  gca  tta      3834
Thr  Leu  Ser  Leu  Phe  Thr  Leu  Ser  Glu  Leu  Asp  Asp  Glu  Ala  Leu
     1265                     1270                1275 gat  ttt  gac  tgg  gag  gaa  gag  atg  agg  aaa  aag  cca  tga                3873
Asp  Phe  Asp  Trp  Glu  Glu  Glu  Met  Arg  Lys  Lys  Pro
     1280                     1285                1290
```

<210> SEQ ID NO 8
<211> LENGTH: 1290
<212> TYPE: PRT
<213> ORGANISM: Mus musculus

<400> SEQUENCE: 8

```
Met Asp Gln Arg Thr Thr Arg Asn Gly Lys Tyr Cys Asp Val Glu Pro
1               5                   10                  15

Val Ser Arg Ser Asn Pro Ala Pro Cys Leu Arg Asp Pro Pro Leu Arg
            20                  25                  30

Arg Leu Val Arg Pro Lys Pro Arg Leu Gln Leu Pro Glu Ser Arg Leu
        35                  40                  45

Ser Pro Cys Ser Arg Leu Pro Leu Ala Asp Ser Ser Val Arg Pro Gly
    50                  55                  60

Ala Arg Pro Pro Ala Ser Ala Pro Gly Arg Ser Pro Ser Gly Arg Lys
65                  70                  75                  80

Val Glu Ala Val Arg Gly Ser Gly Ser Ala Gly Ser Ser Ser Pro Ser
                85                  90                  95

Glu Ala Glu Arg Glu Gln Arg Glu Glu Ala Cys Ala Pro Pro Arg Lys
            100                 105                 110

Ala Ala Pro Ser Ser Gly Arg Ala His Ala Pro Pro Pro Thr Pro
        115                 120                 125

Arg Gly Ser Gly Trp Gly Asp His Gly Arg Ser Ala Val Pro Ala Thr
    130                 135                 140

Lys Thr Val Arg Val Glu Pro Tyr Pro Pro Phe Lys Met Asn Ser Glu
145                 150                 155                 160

Gln Val Thr Leu Val Gly Gln Val Phe Glu Ser Tyr Val Ser Glu Tyr
                165                 170                 175

His Lys Asn Asp Ile Leu Leu Ile Leu Lys Glu Arg Asp Glu Asp Ala
            180                 185                 190

His Tyr Pro Val Val Val Asn Ala Met Ser Leu Phe Glu Thr Asn Met
        195                 200                 205

Glu Ile Gly Asp Tyr Phe Thr Val Phe Pro Asn Glu Val Leu Thr Val
    210                 215                 220

Phe Asp Ser Ala Leu Arg Arg Ser Ala Leu Ala Ile Leu Gln Ser Leu
225                 230                 235                 240

Pro Glu Thr Glu Gly Leu Ser Met Lys Gln Asn Leu His Ala Arg Ile
                245                 250                 255

Ser Gly Leu Pro Val Cys Pro Glu Leu Val Arg Glu His Ile Pro Lys
            260                 265                 270

Thr Lys Asp Val Gly His Phe Leu Ser Val Thr Gly Thr Val Ile Arg
        275                 280                 285

Thr Ser Leu Val Lys Val Leu Glu Phe Glu Arg Asp Tyr Met Cys Asn
    290                 295                 300

Lys Cys Lys His Val Phe Met Val Glu Ala Asp Phe Glu Gln Tyr Tyr
305                 310                 315                 320

Thr Phe Ser Arg Pro Ser Ser Cys Pro Ser Leu Ala Ser Cys Asp Ser
                325                 330                 335

Ser Lys Phe Ser Cys Leu Ser Asp Leu Ser Ser Ser Pro Ala Arg Cys
```

```
                    340                 345                 350
Arg Asp Tyr Gln Glu Ile Lys Ile Gln Glu Gln Val Gln Arg Leu Ser
            355                 360                 365

Val Gly Ser Ile Pro Arg Ser Met Lys Val Ile Leu Glu Asp Asp Leu
            370                 375                 380

Val Asp Ser Cys Lys Ser Gly Asp Asp Leu Thr Ile Tyr Gly Val Val
385                 390                 395                 400

Met Gln Arg Trp Lys Pro Phe Gln Arg Asp Val Arg Cys Glu Val Glu
                405                 410                 415

Ile Val Leu Lys Ala Asn Tyr Val Gln Val Asn Asn Glu Gln Ser Ser
            420                 425                 430

Gly Met Val Met Asp Glu Asp Thr Arg Lys Glu Phe Glu Asp Phe Trp
            435                 440                 445

Glu His Tyr Lys Ser Asp Pro Phe Ala Gly Arg Asn Glu Ile Leu Ala
450                 455                 460

Ser Leu Cys Pro Gln Val Phe Gly Met Tyr Leu Val Lys Leu Ala Val
465                 470                 475                 480

Ala Met Val Leu Ala Gly Gly Ile Gln Arg Thr Asp Ala Ala Gly Thr
                485                 490                 495

Arg Val Arg Gly Glu Ser His Leu Leu Leu Val Gly Asp Pro Gly Thr
                500                 505                 510

Gly Lys Ser Gln Phe Leu Lys Tyr Ala Ala Lys Ile Thr Pro Arg Ser
            515                 520                 525

Val Leu Thr Thr Gly Ile Gly Ser Thr Ser Ala Gly Leu Thr Val Thr
            530                 535                 540

Ala Val Lys Asp Ser Gly Glu Trp Asn Leu Glu Ala Gly Ala Leu Val
545                 550                 555                 560

Leu Ala Asp Ala Gly Leu Cys Cys Ile Asp Glu Phe Asn Ser Leu Lys
                565                 570                 575

Glu His Asp Arg Thr Ser Ile His Glu Ala Met Glu Gln Gln Thr Ile
                580                 585                 590

Ser Val Ala Lys Ala Gly Leu Val Cys Lys Leu Asn Thr Arg Thr Thr
            595                 600                 605

Ile Leu Ala Ala Thr Asn Pro Lys Gly Gln Tyr Asp Pro Lys Glu Ser
            610                 615                 620

Val Ser Val Asn Ile Ala Leu Gly Ser Pro Leu Leu Ser Arg Phe Asp
625                 630                 635                 640

Leu Val Leu Val Leu Leu Asp Thr Arg Asn Glu Asp Trp Asp Arg Ile
                645                 650                 655

Ile Ser Ser Phe Ile Leu Glu Asn Lys Gly Tyr Pro Ser Lys Ser Glu
                660                 665                 670

Asn Leu Trp Ser Met Glu Lys Met Lys Thr Tyr Phe Cys Leu Ile Arg
            675                 680                 685

Asn Leu His Pro Thr Leu Ser Glu Val Ser Asn Gln Val Leu Leu Arg
            690                 695                 700

Tyr Tyr Gln Met Gln Arg Gln Ser Asp Ser Arg Asn Ala Ala Arg Thr
705                 710                 715                 720

Thr Ile Arg Leu Leu Glu Ser Leu Ile Arg Leu Ala Glu Ala His Ala
                725                 730                 735

Arg Leu Met Phe Arg Ser Ala Val Thr Leu Glu Asp Ala Val Thr Ala
                740                 745                 750

Val Ser Val Met Glu Ser Ser Met Gln Gly Gly Ala Leu Leu Gly Gly
            755                 760                 765
```

-continued

Val Asn Ala Leu His Thr Ser Phe Pro Glu Asn Pro Arg Ala Gln Tyr
            770                 775                 780

Gln Arg Gln Cys Glu Leu Ile Leu Glu Lys Leu Glu Leu Gln Gly Leu
785                 790                 795                 800

Leu Gln Glu Glu Leu Arg Arg Leu Glu Arg Leu Gln Asn Glu Ser Val
                805                 810                 815

His Gln Cys Gln Ser His Ser Leu Glu Glu Val Ala Pro Gly Ser
            820                 825                 830

Cys Arg Asn Asp Pro Arg Asp Lys Pro Arg Leu Arg Thr Ser Thr Gln
                835                 840                 845

Gln Glu Gln Ser Cys Ser Trp Ser Ser Thr Glu Arg Ser Gly Ala Asp
850                 855                 860

Ser Pro Pro Gly Pro Gly Leu Asn Arg Pro Thr Ser Cys Asn Asn Ser
865                 870                 875                 880

Ala Glu Asn Arg Asp Gly Arg Gly Asp Gly Leu Asp Trp Leu Asp Pro
                885                 890                 895

Thr Ser Ser Pro Glu Ile Ala Pro Glu Ser Thr Ile Val Ser Pro Asn
            900                 905                 910

Val Lys Thr Thr Glu Lys Asn Val Asn Leu Lys Ile Ser Asn Asn Lys
            915                 920                 925

Ser Gln Gly Lys Glu Lys His Gly Pro Gln Gln Arg Ser Lys Leu Leu
930                 935                 940

Glu Ala Gly His Leu Pro Ser Ser Gly Ala Met Asn Ala Pro Leu Arg
945                 950                 955                 960

Ser His Gly Val Lys Arg Thr Lys Ala Ser Gln Ala Val Val Val Ser
                965                 970                 975

Glu Ala Gly Arg Gly Asp Glu Glu Asp Ser Val Pro Arg Arg Leu Pro
            980                 985                 990

Lys Leu Leu Lys Glu Gly Ser Gln Asn Val Cys Arg Ser Thr Thr Arg
            995                 1000                1005

Val Arg Pro Leu Pro Pro Thr Val Pro Leu Ser Leu Ser Ile Pro
    1010                1015                1020

Ser Pro Gly Ser Gly Lys Arg Ser Gly Thr Pro Lys Arg Lys Arg
    1025                1030                1035

Arg Lys Ser Ala Gln Val Glu Glu Pro Glu Pro Glu Gly Met Glu
    1040                1045                1050

Thr Pro Thr Val Lys Leu Ala Lys Phe Thr Phe Lys Gln Lys Thr
    1055                1060                1065

Lys Leu Thr His Ser Pro Glu Gly Gln Gly Pro Ile Pro Pro Ser
    1070                1075                1080

Ala Ser Glu Ile Ala Val Asp Ser Ser Lys Ile Pro Gln Gln Arg
    1085                1090                1095

Thr Arg Arg Glu Ala Ala Val Pro Val Val Ala Pro Gly Lys Ser
    1100                1105                1110

Thr Ser Thr Ser Gly Asp Arg Cys Ser Asp Gln Leu His Gly Lys
    1115                1120                1125

Thr Lys Glu Leu Ser Arg Gln Pro Pro Asp Ser Asn Pro Pro Arg
    1130                1135                1140

Glu Glu Arg Glu Gln Gly Pro Lys Arg Arg Val Ile Gln Pro Lys
    1145                1150                1155

Pro Glu Leu Gly Asn Gln Ala Gly His Ser His Leu Ala Cys Glu
    1160                1165                1170

Lys Asp Arg Lys Glu Gly Val Ser Cys Gly Asn Lys Ser Ser Lys
    1175                1180                1185

```
Val His Ala Gly Thr Ile Ala Arg Leu Ala Ser Phe Ser Phe Thr
    1190                1195                1200

Ser Pro Ser Glu Ser Lys Ser Glu Ser Leu Pro Pro Glu Arg Lys
    1205                1210                1215

Asp Ser Arg Asp Ser Arg Asp Ser Arg Asp Ser Arg Asp Arg Cys
    1220                1225                1230

His Ser Pro Pro Ala Thr Thr Ala Pro Val Leu Gly Gln Gln Arg
    1235                1240                1245

Gln Thr Phe Gln Leu Gln Gln Pro Thr Glu Arg Ala Asn Leu Ser
    1250                1255                1260

Thr Leu Ser Leu Phe Thr Leu Ser Glu Leu Asp Asp Glu Ala Leu
    1265                1270                1275

Asp Phe Asp Trp Glu Glu Glu Met Arg Lys Lys Pro
    1280                1285                1290

<210> SEQ ID NO 9
<211> LENGTH: 2256
<212> TYPE: DNA
<213> ORGANISM: Mus musculus
<220> FEATURE:
<221> NAME/KEY: CDS
<222> LOCATION: (1)..(2256)

<400> SEQUENCE: 9 ggt ctg acc gtg aca gct gtc aaa gac tca gga gaa tgg aat cta gag      48
Gly Leu Thr Val Thr Ala Val Lys Asp Ser Gly Glu Trp Asn Leu Glu
1               5                   10                  15 gct ggg gct ttg gtg ctt gca gat gct ggt ctc tgc tgt att gac gaa      96
Ala Gly Ala Leu Val Leu Ala Asp Ala Gly Leu Cys Cys Ile Asp Glu
                20                  25                  30 ttt aac agc ctc aaa gaa cat gac agg aca agc atc cat gaa gca atg     144
Phe Asn Ser Leu Lys Glu His Asp Arg Thr Ser Ile His Glu Ala Met
            35                  40                  45 gag caa caa acc ata agt gtt gct aag gct ggc ctt gtt tgt aag ctg     192
Glu Gln Gln Thr Ile Ser Val Ala Lys Ala Gly Leu Val Cys Lys Leu
        50                  55                  60 aac aca agg acc acc atc ctg gca gca act aac ccc aaa ggc cag tat     240
Asn Thr Arg Thr Thr Ile Leu Ala Ala Thr Asn Pro Lys Gly Gln Tyr
65                  70                  75                  80 gac ccc aag gag tct gtg tct gtg aac att gcc ctc ggg agc cca ctc     288
Asp Pro Lys Glu Ser Val Ser Val Asn Ile Ala Leu Gly Ser Pro Leu
                85                  90                  95 tta agt cga ttt gac ctt gtc ctg gtt ttg ctc gac act agg aat gaa     336
Leu Ser Arg Phe Asp Leu Val Leu Val Leu Leu Asp Thr Arg Asn Glu
                100                 105                 110 gac tgg gat cgt atc att tct tcc ttt atc tta gaa aat aaa ggt tat     384
Asp Trp Asp Arg Ile Ile Ser Ser Phe Ile Leu Glu Asn Lys Gly Tyr
            115                 120                 125 cca agc aaa tca gag aat ctg tgg agc atg gag aag atg aaa acc tac     432
Pro Ser Lys Ser Glu Asn Leu Trp Ser Met Glu Lys Met Lys Thr Tyr
        130                 135                 140 ttc tgc ctc att cgg aat ctc cac ccc aca ctg tct gaa gtg agc aat     480
Phe Cys Leu Ile Arg Asn Leu His Pro Thr Leu Ser Glu Val Ser Asn
145                 150                 155                 160 caa gtc ctc ctt cga tac tac caa atg caa agg cag agt gat tcc cgg     528
Gln Val Leu Leu Arg Tyr Tyr Gln Met Gln Arg Gln Ser Asp Ser Arg
                165                 170                 175 aat gca gcc cgg aca acc atc cgc ctg tta gaa agc ttg atc cga tta     576
Asn Ala Ala Arg Thr Thr Ile Arg Leu Leu Glu Ser Leu Ile Arg Leu
                180                 185                 190
```

```
gca gaa gct cac gct cgc ctg atg ttc cgc agt gcc gtg act ctg gaa         624
Ala Glu Ala His Ala Arg Leu Met Phe Arg Ser Ala Val Thr Leu Glu
        195                 200                 205 gat gcc gtt aca gct gta tct gtg atg gag tct tca atg cag gga ggt         672
Asp Ala Val Thr Ala Val Ser Val Met Glu Ser Ser Met Gln Gly Gly
    210                 215                 220 gct ctg cta gga ggt gtg aat gct ctc cac act tcc ttc cct gaa aac         720
Ala Leu Leu Gly Gly Val Asn Ala Leu His Thr Ser Phe Pro Glu Asn
225                 230                 235                 240 ccc cgt gca cag tac cag agg cag tgt gaa ctc att ctg gaa aag ctg         768
Pro Arg Ala Gln Tyr Gln Arg Gln Cys Glu Leu Ile Leu Glu Lys Leu
            245                 250                 255 gaa ctc cag ggc ctc ttg cag gaa gaa ctt cga aga ctg gaa agg tta         816
Glu Leu Gln Gly Leu Leu Gln Glu Glu Leu Arg Arg Leu Glu Arg Leu
        260                 265                 270 cag aat gag agt gta cac caa tgc cag tca cat tca cta gag gag gag         864
Gln Asn Glu Ser Val His Gln Cys Gln Ser His Ser Leu Glu Glu Glu
    275                 280                 285 gtg gct cca ggt tcc tgc aga aat gat ccc agg gac aag cca agg ctc         912
Val Ala Pro Gly Ser Cys Arg Asn Asp Pro Arg Asp Lys Pro Arg Leu
290                 295                 300 agg act tca aca cag cag gaa cag agc tgt agc tgg agt tcc aca gag         960
Arg Thr Ser Thr Gln Gln Glu Gln Ser Cys Ser Trp Ser Ser Thr Glu
305                 310                 315                 320 aga tct ggt gca gac tcc ccg cct ggt cca ggg ctt aat aga cca aca        1008
Arg Ser Gly Ala Asp Ser Pro Pro Gly Pro Gly Leu Asn Arg Pro Thr
            325                 330                 335 agt tgt aac aac tca gct gag aac aga gat ggc aga ggt gac ggt tta        1056
Ser Cys Asn Asn Ser Ala Glu Asn Arg Asp Gly Arg Gly Asp Gly Leu
        340                 345                 350 gac tgg ttg gac ccc aca tca agt cct gag att gca cca gaa agc act        1104
Asp Trp Leu Asp Pro Thr Ser Ser Pro Glu Ile Ala Pro Glu Ser Thr
    355                 360                 365 att gtg tct ccc aat gtg aaa aca act gag aaa aat gtg aat ttg aaa        1152
Ile Val Ser Pro Asn Val Lys Thr Thr Glu Lys Asn Val Asn Leu Lys
370                 375                 380 atc tcc aac aat aaa tct cag ggc aag gag aag cat ggg cca cag caa        1200
Ile Ser Asn Asn Lys Ser Gln Gly Lys Glu Lys His Gly Pro Gln Gln
385                 390                 395                 400 aga agc aaa tta tta gaa gct gga cat ctt cca tca tca gga gcc atg        1248
Arg Ser Lys Leu Leu Glu Ala Gly His Leu Pro Ser Ser Gly Ala Met
            405                 410                 415 aat gcc ccc tta cgg tct cac ggt gtt aag cgt aca aag gca agt cag        1296
Asn Ala Pro Leu Arg Ser His Gly Val Lys Arg Thr Lys Ala Ser Gln
        420                 425                 430 gca gtg gtt gta tct gaa gca gga cgg ggt gat gaa gaa gac tct gtg        1344
Ala Val Val Val Ser Glu Ala Gly Arg Gly Asp Glu Glu Asp Ser Val
    435                 440                 445 ccc cga aga ctc ccc aag ctg ctg aag gag ggg tca cag aat gtg tgc        1392
Pro Arg Arg Leu Pro Lys Leu Leu Lys Glu Gly Ser Gln Asn Val Cys
450                 455                 460 aga agc aca acc aga gtg cga cca ctg cca ccc act gtc cct ctg tcc        1440
Arg Ser Thr Thr Arg Val Arg Pro Leu Pro Pro Thr Val Pro Leu Ser
465                 470                 475                 480 ctg tct atc cct tca cct ggg tca gga aaa aga tca gga aca ccc aaa        1488
Leu Ser Ile Pro Ser Pro Gly Ser Gly Lys Arg Ser Gly Thr Pro Lys
            485                 490                 495 aga aag aga cgg aaa tct gct cag gtg gaa gag cct gaa cct gaa ggt        1536
Arg Lys Arg Arg Lys Ser Ala Gln Val Glu Glu Pro Glu Pro Glu Gly
        500                 505                 510
```

```
atg gag act cca aca gta aag ctg gcc aaa ttc aca ttt aaa cag aag       1584
Met Glu Thr Pro Thr Val Lys Leu Ala Lys Phe Thr Phe Lys Gln Lys
            515                 520                 525 aca aaa ctg acc cac tcc ccc gaa ggc caa ggc ccc ata cct ccc agt       1632
Thr Lys Leu Thr His Ser Pro Glu Gly Gln Gly Pro Ile Pro Pro Ser
    530                 535                 540 gct agt gaa ata gca gtt gac agt tct aaa att ccc caa caa aga aca       1680
Ala Ser Glu Ile Ala Val Asp Ser Ser Lys Ile Pro Gln Gln Arg Thr
545                 550                 555                 560 aga aga gaa gca gct gtg cct gtg gta gcg cca gga aag tcg aca tcc       1728
Arg Arg Glu Ala Ala Val Pro Val Val Ala Pro Gly Lys Ser Thr Ser
                565                 570                 575 acc tca gga gac aga tgc tct gac cag ctg cac gga aag aca aag gag       1776
Thr Ser Gly Asp Arg Cys Ser Asp Gln Leu His Gly Lys Thr Lys Glu
            580                 585                 590 ctc tca agg cag cca cca gac agt aat cca cca aga gag gag agg gaa       1824
Leu Ser Arg Gln Pro Pro Asp Ser Asn Pro Pro Arg Glu Glu Arg Glu
        595                 600                 605 cag ggc ccc aaa aga agg gtt att cag ccc aaa ccg gag ctt ggg aac       1872
Gln Gly Pro Lys Arg Arg Val Ile Gln Pro Lys Pro Glu Leu Gly Asn
    610                 615                 620 cag gct ggg cat tcg cat cta gcc tgt gag aaa gac aga aag gaa ggg       1920
Gln Ala Gly His Ser His Leu Ala Cys Glu Lys Asp Arg Lys Glu Gly
625                 630                 635                 640 gtt tcc tgc ggt aat aaa agc agc aag gtt cat gct ggc acc ata gcc       1968
Val Ser Cys Gly Asn Lys Ser Ser Lys Val His Ala Gly Thr Ile Ala
                645                 650                 655 aga ctg gca agc ttc tcc ttc act tcc cca tca gaa tcc aaa tcg gaa       2016
Arg Leu Ala Ser Phe Ser Phe Thr Ser Pro Ser Glu Ser Lys Ser Glu
            660                 665                 670 tcc ctc cct cct gaa agg aag gac agc agg gac agc agg gac agc agg       2064
Ser Leu Pro Pro Glu Arg Lys Asp Ser Arg Asp Ser Arg Asp Ser Arg
        675                 680                 685 gac agc agg gac agg tgc cac agc cct cct gcg acc aca gct cca gtg       2112
Asp Ser Arg Asp Arg Cys His Ser Pro Pro Ala Thr Thr Ala Pro Val
    690                 695                 700 ctc ggc cag caa agg cag act ttc cag ctg cag cag ccc aca gag aga       2160
Leu Gly Gln Gln Arg Gln Thr Phe Gln Leu Gln Gln Pro Thr Glu Arg
705                 710                 715                 720 gcg aat ctt tcc acc ctc tcc ctc ttc act ctg tcg gaa cta gat gac       2208
Ala Asn Leu Ser Thr Leu Ser Leu Phe Thr Leu Ser Glu Leu Asp Asp
                725                 730                 735 gaa gca tta gat ttt gac tgg gag gaa gag atg agg aaa aag cca tga       2256
Glu Ala Leu Asp Phe Asp Trp Glu Glu Glu Met Arg Lys Lys Pro
            740                 745                 750

<210> SEQ ID NO 10
<211> LENGTH: 751
<212> TYPE: PRT
<213> ORGANISM: Mus musculus

<400> SEQUENCE: 10

Gly Leu Thr Val Thr Ala Val Lys Asp Ser Gly Glu Trp Asn Leu Glu
1               5                   10                  15

Ala Gly Ala Leu Val Leu Ala Asp Ala Gly Leu Cys Cys Ile Asp Glu
            20                  25                  30

Phe Asn Ser Leu Lys Glu His Asp Arg Thr Ser Ile His Glu Ala Met
        35                  40                  45

Glu Gln Gln Thr Ile Ser Val Ala Lys Ala Gly Leu Val Cys Lys Leu
    50                  55                  60
```

```
Asn Thr Arg Thr Thr Ile Leu Ala Ala Thr Asn Pro Lys Gly Gln Tyr
 65                  70                  75                  80

Asp Pro Lys Glu Ser Val Ser Val Asn Ile Ala Leu Gly Ser Pro Leu
             85                  90                  95

Leu Ser Arg Phe Asp Leu Val Leu Val Leu Leu Asp Thr Arg Asn Glu
            100                 105                 110

Asp Trp Asp Arg Ile Ile Ser Ser Phe Ile Leu Glu Asn Lys Gly Tyr
            115                 120                 125

Pro Ser Lys Ser Glu Asn Leu Trp Ser Met Glu Lys Met Lys Thr Tyr
            130                 135                 140

Phe Cys Leu Ile Arg Asn Leu His Pro Thr Leu Ser Glu Val Ser Asn
145                 150                 155                 160

Gln Val Leu Leu Arg Tyr Tyr Gln Met Gln Arg Gln Ser Asp Ser Arg
                165                 170                 175

Asn Ala Ala Arg Thr Thr Ile Arg Leu Leu Glu Ser Leu Ile Arg Leu
                180                 185                 190

Ala Glu Ala His Ala Arg Leu Met Phe Arg Ser Ala Val Thr Leu Glu
                195                 200                 205

Asp Ala Val Thr Ala Val Ser Val Met Glu Ser Ser Met Gln Gly Gly
            210                 215                 220

Ala Leu Leu Gly Gly Val Asn Ala Leu His Thr Ser Phe Pro Glu Asn
225                 230                 235                 240

Pro Arg Ala Gln Tyr Gln Arg Gln Cys Glu Leu Ile Leu Glu Lys Leu
                245                 250                 255

Glu Leu Gln Gly Leu Leu Gln Glu Glu Leu Arg Arg Leu Glu Arg Leu
            260                 265                 270

Gln Asn Glu Ser Val His Gln Cys Gln Ser His Ser Leu Glu Glu Glu
            275                 280                 285

Val Ala Pro Gly Ser Cys Arg Asn Asp Pro Arg Asp Lys Pro Arg Leu
            290                 295                 300

Arg Thr Ser Thr Gln Gln Glu Gln Ser Cys Ser Trp Ser Ser Thr Glu
305                 310                 315                 320

Arg Ser Gly Ala Asp Ser Pro Pro Gly Pro Gly Leu Asn Arg Pro Thr
                325                 330                 335

Ser Cys Asn Asn Ser Ala Glu Asn Arg Asp Gly Arg Gly Asp Gly Leu
            340                 345                 350

Asp Trp Leu Asp Pro Thr Ser Ser Pro Glu Ile Ala Pro Glu Ser Thr
            355                 360                 365

Ile Val Ser Pro Asn Val Lys Thr Thr Glu Lys Asn Val Asn Leu Lys
            370                 375                 380

Ile Ser Asn Asn Lys Ser Gln Gly Lys Glu Lys His Gly Pro Gln Gln
385                 390                 395                 400

Arg Ser Lys Leu Leu Glu Ala Gly His Leu Pro Ser Ser Gly Ala Met
            405                 410                 415

Asn Ala Pro Leu Arg Ser His Gly Val Lys Arg Thr Lys Ala Ser Gln
            420                 425                 430

Ala Val Val Val Ser Glu Ala Gly Arg Gly Asp Glu Asp Ser Val
            435                 440                 445

Pro Arg Arg Leu Pro Lys Leu Leu Lys Glu Gly Ser Gln Asn Val Cys
            450                 455                 460

Arg Ser Thr Thr Arg Val Arg Pro Leu Pro Pro Thr Val Pro Leu Ser
465                 470                 475                 480

Leu Ser Ile Pro Ser Pro Gly Ser Gly Lys Arg Ser Gly Thr Pro Lys
```

```
                      485                 490                 495
Arg Lys Arg Arg Lys Ser Ala Gln Val Glu Pro Glu Pro Glu Gly
                500                 505                 510

Met Glu Thr Pro Thr Val Lys Leu Ala Lys Phe Thr Phe Lys Gln Lys
            515                 520                 525

Thr Lys Leu Thr His Ser Pro Glu Gly Gln Gly Pro Ile Pro Pro Ser
        530                 535                 540

Ala Ser Glu Ile Ala Val Asp Ser Ser Lys Ile Pro Gln Gln Arg Thr
545                 550                 555                 560

Arg Arg Glu Ala Ala Val Pro Val Val Ala Pro Gly Lys Ser Thr Ser
                565                 570                 575

Thr Ser Gly Asp Arg Cys Ser Asp Gln Leu His Gly Lys Thr Lys Glu
            580                 585                 590

Leu Ser Arg Gln Pro Pro Asp Ser Asn Pro Pro Arg Glu Glu Arg Glu
        595                 600                 605

Gln Gly Pro Lys Arg Arg Val Ile Gln Pro Lys Pro Glu Leu Gly Asn
610                 615                 620

Gln Ala Gly His Ser His Leu Ala Cys Glu Lys Asp Arg Lys Glu Gly
625                 630                 635                 640

Val Ser Cys Gly Asn Lys Ser Ser Lys Val His Ala Gly Thr Ile Ala
                645                 650                 655

Arg Leu Ala Ser Phe Ser Phe Thr Ser Pro Ser Glu Ser Lys Ser Glu
            660                 665                 670

Ser Leu Pro Pro Glu Arg Lys Asp Ser Arg Asp Ser Arg Asp Ser Arg
        675                 680                 685

Asp Ser Arg Asp Arg Cys His Ser Pro Pro Ala Thr Thr Ala Pro Val
690                 695                 700

Leu Gly Gln Gln Arg Gln Thr Phe Gln Leu Gln Gln Pro Thr Glu Arg
705                 710                 715                 720

Ala Asn Leu Ser Thr Leu Ser Leu Phe Thr Leu Ser Glu Leu Asp Asp
                725                 730                 735

Glu Ala Leu Asp Phe Asp Trp Glu Glu Glu Met Arg Lys Lys Pro
            740                 745                 750

<210> SEQ ID NO 11
<211> LENGTH: 1617
<212> TYPE: DNA
<213> ORGANISM: Mus musculus
<220> FEATURE:
<221> NAME/KEY: CDS
<222> LOCATION: (1)..(1617)

<400> SEQUENCE: 11 atg gat cag aga act aca cga aat gga aaa tat tgt gac gtg gaa ccg    48
Met Asp Gln Arg Thr Thr Arg Asn Gly Lys Tyr Cys Asp Val Glu Pro
1               5                   10                  15 gtg tcc cgc tca aac ccc gcc cca tgc ctc cga gac ccg ccc ctc aga    96
Val Ser Arg Ser Asn Pro Ala Pro Cys Leu Arg Asp Pro Pro Leu Arg
                20                  25                  30 cgt ctt gtc cgg ccc aaa ccc cgc ctc cag ctc ccc gag tcc cgc ctc   144
Arg Leu Val Arg Pro Lys Pro Arg Leu Gln Leu Pro Glu Ser Arg Leu
            35                  40                  45 tct ccc tgc tcc cgc ctc ccg ctc gca gac tcc agc gtc cgt cct ggc   192
Ser Pro Cys Ser Arg Leu Pro Leu Ala Asp Ser Ser Val Arg Pro Gly
        50                  55                  60 gcg cgc ccg cct gcg tcc gca ccc gga aga agc ccc agc ggc cgg aaa   240
Ala Arg Pro Pro Ala Ser Ala Pro Gly Arg Ser Pro Ser Gly Arg Lys
65                  70                  75                  80
```

```
gtt gag gca gtg cgc ggc tcg ggg tcc gcg gga agc tca agt cct tca      288
Val Glu Ala Val Arg Gly Ser Gly Ser Ala Gly Ser Ser Ser Pro Ser
                 85                  90                  95 gag gcc gag cga gag cag cgc gaa gaa gcc tgc gcg ccc ccg cgc aag      336
Glu Ala Glu Arg Glu Gln Arg Glu Glu Ala Cys Ala Pro Pro Arg Lys
            100                 105                 110 gcg gcc ccc tcg agc ggc cgc gcg cac gcc ccg ccc cct cca acg ccg      384
Ala Ala Pro Ser Ser Gly Arg Ala His Ala Pro Pro Pro Pro Thr Pro
            115                 120                 125 cgc ggg tcg ggc tgg ggc gac cac ggc cgc agc gcg gtc ccg gcg acc      432
Arg Gly Ser Gly Trp Gly Asp His Gly Arg Ser Ala Val Pro Ala Thr
        130                 135                 140 aag aca gtg cgt gtt gag ccc tac cca ccc ttc aag atg aat agt gag      480
Lys Thr Val Arg Val Glu Pro Tyr Pro Pro Phe Lys Met Asn Ser Glu
145                 150                 155                 160 cag gtc acc ctg gtg ggt cag gtg ttt gag tcc tat gtt tca gag tac      528
Gln Val Thr Leu Val Gly Gln Val Phe Glu Ser Tyr Val Ser Glu Tyr
                165                 170                 175 cat aag aac gat att ctt ctg atc ctg aaa gaa aga gat gaa gat gct      576
His Lys Asn Asp Ile Leu Leu Ile Leu Lys Glu Arg Asp Glu Asp Ala
            180                 185                 190 cac tac ccg gtt gtg gtt aat gct atg agc ctt ttc gag acc aac atg      624
His Tyr Pro Val Val Val Asn Ala Met Ser Leu Phe Glu Thr Asn Met
            195                 200                 205 gaa att ggg gac tat ttc acc gtg ttc ccc aat gaa gta cta aca gtt      672
Glu Ile Gly Asp Tyr Phe Thr Val Phe Pro Asn Glu Val Leu Thr Val
        210                 215                 220 ttt gac agt gca ctt cga agg tca gcc ttg gca att ctg cag tcc ctt      720
Phe Asp Ser Ala Leu Arg Arg Ser Ala Leu Ala Ile Leu Gln Ser Leu
225                 230                 235                 240 cct gag acg gag ggg tta tcc atg aag cag aat ctt cat gcc agg ata      768
Pro Glu Thr Glu Gly Leu Ser Met Lys Gln Asn Leu His Ala Arg Ile
                245                 250                 255 tca ggt ttg cct gtt tgt cca gaa ctg gtc agg gaa cac att ccc aaa      816
Ser Gly Leu Pro Val Cys Pro Glu Leu Val Arg Glu His Ile Pro Lys
            260                 265                 270 acc aag gat gtg gga cac ttc tta tct gtc act ggg aca gtg atc cga      864
Thr Lys Asp Val Gly His Phe Leu Ser Val Thr Gly Thr Val Ile Arg
            275                 280                 285 acg agt ctg gtg aag gtc ttg gag ttc gag cgg gat tac atg tgt aac      912
Thr Ser Leu Val Lys Val Leu Glu Phe Glu Arg Asp Tyr Met Cys Asn
        290                 295                 300 aaa tgc aag cat gtg ttc atg gtg gag gca gac ttc gag cag tat tac      960
Lys Cys Lys His Val Phe Met Val Glu Ala Asp Phe Glu Gln Tyr Tyr
305                 310                 315                 320 acc ttc agt cgg cca tcg tca tgt cca agt tta gcc agc tgt gac tcc     1008
Thr Phe Ser Arg Pro Ser Ser Cys Pro Ser Leu Ala Ser Cys Asp Ser
                325                 330                 335 tca aaa ttc tct tgc ctc tca gac ttg tct tca tct cca gcc aga tgt     1056
Ser Lys Phe Ser Cys Leu Ser Asp Leu Ser Ser Ser Pro Ala Arg Cys
            340                 345                 350 cgg gat tac cag gaa atc aaa att cag gag cag gtg caa agg ctg tct     1104
Arg Asp Tyr Gln Glu Ile Lys Ile Gln Glu Gln Val Gln Arg Leu Ser
            355                 360                 365 gtt gga agt atc cca cgg tct atg aaa gtt att ctg gaa gat gac cta     1152
Val Gly Ser Ile Pro Arg Ser Met Lys Val Ile Leu Glu Asp Asp Leu
        370                 375                 380 gtt gac agt tgc aaa tct gga gat gac ctc acc atc tat ggg gtt gta     1200
Val Asp Ser Cys Lys Ser Gly Asp Asp Leu Thr Ile Tyr Gly Val Val
385                 390                 395                 400
```

```
atg caa cgg tgg aaa ccc ttt cag cga gat gta cgc tgt gaa gtt gag   1248
Met Gln Arg Trp Lys Pro Phe Gln Arg Asp Val Arg Cys Glu Val Glu
            405                 410                 415 att gtc ttg aaa gcc aac tat gtc caa gtg aat aat gag caa tcc tcg   1296
Ile Val Leu Lys Ala Asn Tyr Val Gln Val Asn Asn Glu Gln Ser Ser
        420                 425                 430 ggg atg gtc atg gat gag gac act cga aaa gaa ttt gaa gac ttc tgg   1344
Gly Met Val Met Asp Glu Asp Thr Arg Lys Glu Phe Glu Asp Phe Trp
    435                 440                 445 gaa cac tat aag agt gac ccc ttt gca ggg agg aat gaa ata ttg gcc   1392
Glu His Tyr Lys Ser Asp Pro Phe Ala Gly Arg Asn Glu Ile Leu Ala
450                 455                 460 agc ttg tgt cct caa gtt ttt ggg atg tat cta gtg aag ctt gct gtg   1440
Ser Leu Cys Pro Gln Val Phe Gly Met Tyr Leu Val Lys Leu Ala Val
465                 470                 475                 480 gcc atg gta ctg gct ggt gga att caa aga act gat gct gca gga acc   1488
Ala Met Val Leu Ala Gly Gly Ile Gln Arg Thr Asp Ala Ala Gly Thr
                485                 490                 495 agg gtt aga ggg gaa tct cac ctt tta ttg gtt ggg gat cct ggc aca   1536
Arg Val Arg Gly Glu Ser His Leu Leu Leu Val Gly Asp Pro Gly Thr
            500                 505                 510 ggg aaa tca caa ttc ctt aaa tat gca gca aag att acc cca agg tcc   1584
Gly Lys Ser Gln Phe Leu Lys Tyr Ala Ala Lys Ile Thr Pro Arg Ser
        515                 520                 525 gtt ttg acc aca gga att gga tct act agt gca                       1617
Val Leu Thr Thr Gly Ile Gly Ser Thr Ser Ala
    530                 535

<210> SEQ ID NO 12
<211> LENGTH: 539
<212> TYPE: PRT
<213> ORGANISM: Mus musculus

<400> SEQUENCE: 12

Met Asp Gln Arg Thr Thr Arg Asn Gly Lys Tyr Cys Asp Val Glu Pro
1               5                   10                  15

Val Ser Arg Ser Asn Pro Ala Pro Cys Leu Arg Asp Pro Pro Leu Arg
            20                  25                  30

Arg Leu Val Arg Pro Lys Pro Arg Leu Gln Leu Pro Glu Ser Arg Leu
        35                  40                  45

Ser Pro Cys Ser Arg Leu Pro Leu Ala Asp Ser Ser Val Arg Pro Gly
    50                  55                  60

Ala Arg Pro Pro Ala Ser Ala Pro Gly Arg Ser Pro Gly Arg Lys
65                  70                  75                  80

Val Glu Ala Val Arg Gly Ser Gly Ser Ala Gly Ser Ser Ser Pro Ser
                85                  90                  95

Glu Ala Glu Arg Glu Gln Arg Glu Glu Ala Cys Ala Pro Pro Arg Lys
            100                 105                 110

Ala Ala Pro Ser Ser Gly Arg Ala His Ala Pro Pro Pro Thr Pro
        115                 120                 125

Arg Gly Ser Gly Trp Gly Asp His Gly Arg Ser Ala Val Pro Ala Thr
    130                 135                 140

Lys Thr Val Arg Val Glu Pro Tyr Pro Pro Phe Lys Met Asn Ser Glu
145                 150                 155                 160

Gln Val Thr Leu Val Gly Gln Val Phe Glu Ser Tyr Val Ser Glu Tyr
                165                 170                 175

His Lys Asn Asp Ile Leu Leu Ile Leu Lys Glu Arg Asp Glu Asp Ala
            180                 185                 190
```

His Tyr Pro Val Val Asn Ala Met Ser Leu Phe Glu Thr Asn Met
        195                 200                 205

Glu Ile Gly Asp Tyr Phe Thr Val Phe Pro Asn Glu Val Leu Thr Val
    210                 215                 220

Phe Asp Ser Ala Leu Arg Arg Ser Ala Leu Ile Leu Gln Ser Leu
225                 230                 235                 240

Pro Glu Thr Glu Gly Leu Ser Met Lys Gln Asn Leu His Ala Arg Ile
                245                 250                 255

Ser Gly Leu Pro Val Cys Pro Glu Leu Val Arg Glu His Ile Pro Lys
            260                 265                 270

Thr Lys Asp Val Gly His Phe Leu Ser Val Thr Gly Thr Val Ile Arg
        275                 280                 285

Thr Ser Leu Val Lys Val Leu Glu Phe Glu Arg Asp Tyr Met Cys Asn
    290                 295                 300

Lys Cys Lys His Val Phe Met Val Glu Ala Asp Phe Glu Gln Tyr Tyr
305                 310                 315                 320

Thr Phe Ser Arg Pro Ser Ser Cys Pro Ser Leu Ala Ser Cys Asp Ser
                325                 330                 335

Ser Lys Phe Ser Cys Leu Ser Asp Leu Ser Ser Ser Pro Ala Arg Cys
            340                 345                 350

Arg Asp Tyr Gln Glu Ile Lys Ile Gln Glu Gln Val Gln Arg Leu Ser
        355                 360                 365

Val Gly Ser Ile Pro Arg Ser Met Lys Val Ile Leu Glu Asp Asp Leu
    370                 375                 380

Val Asp Ser Cys Lys Ser Gly Asp Asp Leu Thr Ile Tyr Gly Val Val
385                 390                 395                 400

Met Gln Arg Trp Lys Pro Phe Gln Arg Asp Val Arg Cys Glu Val Glu
                405                 410                 415

Ile Val Leu Lys Ala Asn Tyr Val Gln Val Asn Asn Glu Gln Ser Ser
            420                 425                 430

Gly Met Val Met Asp Glu Asp Thr Arg Lys Glu Phe Glu Asp Phe Trp
        435                 440                 445

Glu His Tyr Lys Ser Asp Pro Phe Ala Gly Arg Asn Glu Ile Leu Ala
    450                 455                 460

Ser Leu Cys Pro Gln Val Phe Gly Met Tyr Leu Val Lys Leu Ala Val
465                 470                 475                 480

Ala Met Val Leu Ala Gly Gly Ile Gln Arg Thr Asp Ala Ala Gly Thr
                485                 490                 495

Arg Val Arg Gly Glu Ser His Leu Leu Leu Val Gly Asp Pro Gly Thr
            500                 505                 510

Gly Lys Ser Gln Phe Leu Lys Tyr Ala Ala Lys Ile Thr Pro Arg Ser
        515                 520                 525

Val Leu Thr Thr Gly Ile Gly Ser Thr Ser Ala
    530                 535

<210> SEQ ID NO 13
<211> LENGTH: 3432
<212> TYPE: DNA
<213> ORGANISM: Xenopus sp.
<220> FEATURE:
<221> NAME/KEY: CDS
<222> LOCATION: (1)..(3429)

<400> SEQUENCE: 13 atg tat ctc ggt ttt gaa caa gta gcg ctg gtg ggc caa gtc ttt gaa      48
Met Tyr Leu Gly Phe Glu Gln Val Ala Leu Val Gly Gln Val Phe Glu

```
                        -continued
1           5              10              15
tcc ttt gtg ctg gag cac cac aaa aat gag att gcc cag ata ctt act    96
Ser Phe Val Leu Glu His His Lys Asn Glu Ile Ala Gln Ile Leu Thr
             20              25              30 gag aaa gaa gag cat gcc cac tac tca ctg gtt gtt aat gcc atg aca   144
Glu Lys Glu Glu His Ala His Tyr Ser Leu Val Val Asn Ala Met Thr
         35              40              45 ctt ttt gaa gca aac atg gag att gga gag tac ttt aat gcc ttt cca   192
Leu Phe Glu Ala Asn Met Glu Ile Gly Glu Tyr Phe Asn Ala Phe Pro
     50              55              60 aat gaa gtt ctg ccc gtc ttt gat aat gct ctg cgc tgt gct gcc atg   240
Asn Glu Val Leu Pro Val Phe Asp Asn Ala Leu Arg Cys Ala Ala Met
65              70              75              80 agc ttt ctt cag tct tgt tca gaa aaa tac aca ttt ctt atg aag cag   288
Ser Phe Leu Gln Ser Cys Ser Glu Lys Tyr Thr Phe Leu Met Lys Gln
             85              90              95 aat ctt cat gca agg ata aca ggt cta cca gtg tgc cca gag tta acc   336
Asn Leu His Ala Arg Ile Thr Gly Leu Pro Val Cys Pro Glu Leu Thr
             100             105             110 aga gag cac ata cca cga acc aga gat gtg ggg cat ttc ctt tct gta   384
Arg Glu His Ile Pro Arg Thr Arg Asp Val Gly His Phe Leu Ser Val
             115             120             125 acc ggt aca gta att cgc acc agc ttg gtt aaa gtg ctc gag tat gag   432
Thr Gly Thr Val Ile Arg Thr Ser Leu Val Lys Val Leu Glu Tyr Glu
         130             135             140 caa gac ttc atg tgc aac aag tgt aag cat gtg gtc act gtg aaa gca   480
Gln Asp Phe Met Cys Asn Lys Cys Lys His Val Val Thr Val Lys Ala
145             150             155             160 gac ttt gag cag cat tac aca ttc aag cca ccc atc gct tgc tca aat   528
Asp Phe Glu Gln His Tyr Thr Phe Lys Pro Pro Ile Ala Cys Ser Asn
             165             170             175 gag gaa ggc tgc aac tcc acc aaa ttc acc tgt ctg tca gat tca tcc   576
Glu Glu Gly Cys Asn Ser Thr Lys Phe Thr Cys Leu Ser Asp Ser Ser
             180             185             190 tct cca gcc agc tgc aga gac tat caa gag atc aag att cag gaa cag   624
Ser Pro Ala Ser Cys Arg Asp Tyr Gln Glu Ile Lys Ile Gln Glu Gln
         195             200             205 gtt caa agg cta tct gtt ggc agt atc cct cga tca atg att gta gtt   672
Val Gln Arg Leu Ser Val Gly Ser Ile Pro Arg Ser Met Ile Val Val
     210             215             220 ttg gaa gat gac ctg gtt gac agc tgc aaa tct gga gat gat ata aca   720
Leu Glu Asp Asp Leu Val Asp Ser Cys Lys Ser Gly Asp Asp Ile Thr
225             230             235             240 gtc tat ggt gtg gtg atg cag cgg tgg aaa ccc ctt tat ata gac atg   768
Val Tyr Gly Val Val Met Gln Arg Trp Lys Pro Leu Tyr Ile Asp Met
             245             250             255 cgc tgt gac ctg gaa att gtt tta aag gcc aat tac att tca gtc aat   816
Arg Cys Asp Leu Glu Ile Val Leu Lys Ala Asn Tyr Ile Ser Val Asn
             260             265             270 aat gag caa cct tgt ggt gtg gtt ata aat gaa gaa gta cgc aaa gag   864
Asn Glu Gln Pro Cys Gly Val Val Ile Asn Glu Glu Val Arg Lys Glu
         275             280             285 tat gaa gat ttc tgg gtg aag tat agg aac aac cct tta gaa ggt agg   912
Tyr Glu Asp Phe Trp Val Lys Tyr Arg Asn Asn Pro Leu Glu Gly Arg
     290             295             300 aat gaa att ctg gcc agc ctg tgt ccg cag gta ttt ggt atg ttt gta   960
Asn Glu Ile Leu Ala Ser Leu Cys Pro Gln Val Phe Gly Met Phe Val
305             310             315             320 gtg aag ctg gca gtg gcc atg gtg ctg gct ggt gga gtt cag aga att  1008
Val Lys Leu Ala Val Ala Met Val Leu Ala Gly Gly Val Gln Arg Ile
```

```
                                        325                         330                         335
gat tct gct gga aca aga gtg aga ggt gag tca cat ctt ctg cta gtt    1056
Asp Ser Ala Gly Thr Arg Val Arg Gly Glu Ser His Leu Leu Leu Val
            340                         345                         350 gga gac cct ggc acg ggg aaa tca cag ttt ctg aag tat gct gca aaa    1104
Gly Asp Pro Gly Thr Gly Lys Ser Gln Phe Leu Lys Tyr Ala Ala Lys
                355                         360                         365 att act ccg agg tct gtc ctt act gca ggc att gga tct act agt gca    1152
Ile Thr Pro Arg Ser Val Leu Thr Ala Gly Ile Gly Ser Thr Ser Ala
370                         375                         380 ggc ttg act gtt act gca gtg aaa gac tct gga gag tgg aat ctg gag    1200
Gly Leu Thr Val Thr Ala Val Lys Asp Ser Gly Glu Trp Asn Leu Glu
385                         390                         395                         400 gct gga gcc ttg gtg tta gct gat gga ggc ctg tgc tgc att gat gaa    1248
Ala Gly Ala Leu Val Leu Ala Asp Gly Gly Leu Cys Cys Ile Asp Glu
                405                         410                         415 ttt aat agc atc aag gag cat gac aga acc agc atc cat gag gca atg    1296
Phe Asn Ser Ile Lys Glu His Asp Arg Thr Ser Ile His Glu Ala Met
                420                         425                         430 gag cag cag acc atc agt gtt gca aag gct ggg tta gtg tgc aag ctg    1344
Glu Gln Gln Thr Ile Ser Val Ala Lys Ala Gly Leu Val Cys Lys Leu
            435                         440                         445 aac act agg aca acc att ttg gca gca aca aat ccc aaa ggc caa tat    1392
Asn Thr Arg Thr Thr Ile Leu Ala Ala Thr Asn Pro Lys Gly Gln Tyr
450                         455                         460 gac cca gac gaa tcc atc tcg gtg aat gta gcc ctt gct agc cct ctg    1440
Asp Pro Asp Glu Ser Ile Ser Val Asn Val Ala Leu Ala Ser Pro Leu
465                         470                         475                         480 ctc agc aga ttt gac ttg gtt cta gtt ttg ctg gat acc aaa aat gaa    1488
Leu Ser Arg Phe Asp Leu Val Leu Val Leu Leu Asp Thr Lys Asn Glu
                485                         490                         495 gac tgg gac cgc att att tct tcg ttt att ttg gag agt aaa ggc tgc    1536
Asp Trp Asp Arg Ile Ile Ser Ser Phe Ile Leu Glu Ser Lys Gly Cys
                500                         505                         510 cct cgt aaa tcc gat aag cta tgg agc atg gag aag atg aaa acc tat    1584
Pro Arg Lys Ser Asp Lys Leu Trp Ser Met Glu Lys Met Lys Thr Tyr
            515                         520                         525 ttc tgt ctt att aag aat ctt caa ccc aaa atg tct caa gat gct aat    1632
Phe Cys Leu Ile Lys Asn Leu Gln Pro Lys Met Ser Gln Asp Ala Asn
530                         535                         540 gtt atc ctg gta cgt tat tac cag cta cag cgg caa agc agt tgc agg    1680
Val Ile Leu Val Arg Tyr Tyr Gln Leu Gln Arg Gln Ser Ser Cys Arg
545                         550                         555                         560 aat gca gca cgt act act att aga ttg cta gaa agt ttg atc cgc cta    1728
Asn Ala Ala Arg Thr Thr Ile Arg Leu Leu Glu Ser Leu Ile Arg Leu
                565                         570                         575 gca gaa gcc cat gct cgg ata atg tat cgg gat gtt gtg acc acc gaa    1776
Ala Glu Ala His Ala Arg Ile Met Tyr Arg Asp Val Val Thr Thr Glu
                580                         585                         590 gat gcc ata acc gtg gtg tcc ata atg gag tcc tcg atg cag gga ggt    1824
Asp Ala Ile Thr Val Val Ser Ile Met Glu Ser Ser Met Gln Gly Gly
            595                         600                         605 gca tta ctt ggc ggt gtc aat gca tta cac aca tcc ttt cca gaa aat    1872
Ala Leu Leu Gly Gly Val Asn Ala Leu His Thr Ser Phe Pro Glu Asn
610                         615                         620 cca agg gaa cag tat cgg ctt cag tgc gag ctc cta ttg gat aaa ctt    1920
Pro Arg Glu Gln Tyr Arg Leu Gln Cys Glu Leu Leu Leu Asp Lys Leu
625                         630                         635                         640 ggg ctt cag aaa ttg cta gag gaa gag ctt caa agg cta gaa agg cag    1968
Gly Leu Gln Lys Leu Leu Glu Glu Glu Leu Gln Arg Leu Glu Arg Gln
```

-continued

```
                645                 650                 655
caa agt gaa gac tcc ctt gag tct gat ctt ggg gaa agt gca aca aac    2016
Gln Ser Glu Asp Ser Leu Glu Ser Asp Leu Gly Glu Ser Ala Thr Asn
            660                 665                 670 ctc gtt gga cat aaa gta gtg cac agt gag tgt gtc atg gaa gaa acc    2064
Leu Val Gly His Lys Val Val His Ser Glu Cys Val Met Glu Glu Thr
        675                 680                 685 ttc agc act ttt gaa gct tct tct ttg cca gat gaa aca cac ctg gga    2112
Phe Ser Thr Phe Glu Ala Ser Ser Leu Pro Asp Glu Thr His Leu Gly
    690                 695                 700 gta act ggc agt gct gca ttc ata cag act cct aag aaa acc atc tcc    2160
Val Thr Gly Ser Ala Ala Phe Ile Gln Thr Pro Lys Lys Thr Ile Ser
705                 710                 715                 720 gat atg acc aaa agt gat gac acc att agg aag ggt acc att aca cct    2208
Asp Met Thr Lys Ser Asp Asp Thr Ile Arg Lys Gly Thr Ile Thr Pro
                725                 730                 735 gct gaa caa aac aga ggt att agc aca gat gcc gag tcc tct tta aaa    2256
Ala Glu Gln Asn Arg Gly Ile Ser Thr Asp Ala Glu Ser Ser Leu Lys
            740                 745                 750 caa ggt aat gca caa cca ctc gct ggt ggg cat ctc tct gaa aat aat    2304
Gln Gly Asn Ala Gln Pro Leu Ala Gly Gly His Leu Ser Glu Asn Asn
        755                 760                 765 ctt aca aaa tgc act gat aac agt ctt ggc tgg ttt gat aca ctt caa    2352
Leu Thr Lys Cys Thr Asp Asn Ser Leu Gly Trp Phe Asp Thr Leu Gln
    770                 775                 780 tcc att cag atg tct ccc atc acc aaa caa aga gaa gga tgc aca gct    2400
Ser Ile Gln Met Ser Pro Ile Thr Lys Gln Arg Glu Gly Cys Thr Ala
785                 790                 795                 800 gaa aag ctt caa caa gaa gtc ctt cct gta tca aca gaa agt agc tgc    2448
Glu Lys Leu Gln Gln Glu Val Leu Pro Val Ser Thr Glu Ser Ser Cys
                805                 810                 815 cat cct gca gac aaa aaa gtt gta aat tta gga ggg agg aac aaa ctt    2496
His Pro Ala Asp Lys Lys Val Val Asn Leu Gly Gly Arg Asn Lys Leu
            820                 825                 830 gaa gtt ttg caa gct agt gga agc agc cct ggg gga aat gga agg gat    2544
Glu Val Leu Gln Ala Ser Gly Ser Ser Pro Gly Gly Asn Gly Arg Asp
        835                 840                 845 ttg tca aat cac aca gtg act tgt gga agc agc cct gag aga aac aaa    2592
Leu Ser Asn His Thr Val Thr Cys Gly Ser Ser Pro Glu Arg Asn Lys
    850                 855                 860 aga gat ttg tca aat cac ata gtg act gag cat gtt tct aaa aag tgg    2640
Arg Asp Leu Ser Asn His Ile Val Thr Glu His Val Ser Lys Lys Trp
865                 870                 875                 880 cgg aga ata aat aaa gat tcc ctt tgt gga aaa aat gtg cca tct ttc    2688
Arg Arg Ile Asn Lys Asp Ser Leu Cys Gly Lys Asn Val Pro Ser Phe
                885                 890                 895 cag cct cag tct gaa aat aca gat tcg gct cca gtc tgc tcc agt gtt    2736
Gln Pro Gln Ser Glu Asn Thr Asp Ser Ala Pro Val Cys Ser Ser Val
            900                 905                 910 cct ctg cat agt acc cct gat gtt gcc cag aga agg aaa aga att att    2784
Pro Leu His Ser Thr Pro Asp Val Ala Gln Arg Arg Lys Arg Ile Ile
        915                 920                 925 gcc cag gtg gaa aag caa tcg aaa gca gaa gtg gag gat cca gac aca    2832
Ala Gln Val Glu Lys Gln Ser Lys Ala Glu Val Glu Asp Pro Asp Thr
    930                 935                 940 aaa gca cga cta gcc cag ttg gcc aag ttt tca ttt aag cga cat tca    2880
Lys Ala Arg Leu Ala Gln Leu Ala Lys Phe Ser Phe Lys Arg His Ser
945                 950                 955                 960 aaa ctg gtg cat tca cct gca ggg gat act gac aca gca tca aat gca    2928
Lys Leu Val His Ser Pro Ala Gly Asp Thr Asp Thr Ala Ser Asn Ala
```

```
                     965                 970                 975
cag aaa cat gat cac cca gtc cag aaa att aca cta tca gag aag ttg      2976
Gln Lys His Asp His Pro Val Gln Lys Ile Thr Leu Ser Glu Lys Leu
                980                 985                 990 aac aat tta ggt agg act gta aat aat gtg gat aaa tca agc aat tct      3024
Asn Asn Leu Gly Arg Thr Val Asn Asn Val Asp Lys Ser Ser Asn Ser
                995                1000                1005 gtt aat ggc tca aag cag caa aag cat gta gag aat aca tcc aaa          3069
Val Asn Gly Ser Lys Gln Gln Lys His Val Glu Asn Thr Ser Lys
       1010                1015                1020 cag act gta ata acg cag aag agt aac ttt gaa tcg aac aca tta          3114
Gln Thr Val Ile Thr Gln Lys Ser Asn Phe Glu Ser Asn Thr Leu
       1025                1030                1035 aac gct cct gtg cat gag aca aag ttg aat gag ggg tgt gac tcc          3159
Asn Ala Pro Val His Glu Thr Lys Leu Asn Glu Gly Cys Asp Ser
       1040                1045                1050 aga aag gtt tct tct agt aca ctt gct aag tta gca cgc ttt tct          3204
Arg Lys Val Ser Ser Ser Thr Leu Ala Lys Leu Ala Arg Phe Ser
       1055                1060                1065 ttc tca cct cct cct gaa aat caa gca gcg gag acc agc aag gaa          3249
Phe Ser Pro Pro Pro Glu Asn Gln Ala Ala Glu Thr Ser Lys Glu
       1070                1075                1080 acc ctg att tta cca aga gct gtt gct cca ggc agc aaa aga aag          3294
Thr Leu Ile Leu Pro Arg Ala Val Ala Pro Gly Ser Lys Arg Lys
       1085                1090                1095 tgt ttt gaa ctg aat cct tcc act gat aaa acc aca atg tca agt          3339
Cys Phe Glu Leu Asn Pro Ser Thr Asp Lys Thr Thr Met Ser Ser
       1100                1105                1110 aaa tct ctt ttc tct aca aca gac tta gat gat gaa gag tta gat          3384
Lys Ser Leu Phe Ser Thr Thr Asp Leu Asp Asp Glu Glu Leu Asp
       1115                1120                1125 gtg gat tgg gag gct gaa ata aaa gga aat cag aga att gcc aca          3429
Val Asp Trp Glu Ala Glu Ile Lys Gly Asn Gln Arg Ile Ala Thr
       1130                1135                1140 tga                                                                   3432

<210> SEQ ID NO 14
<211> LENGTH: 1143
<212> TYPE: PRT
<213> ORGANISM: Xenopus sp.

<400> SEQUENCE: 14

Met Tyr Leu Gly Phe Glu Gln Val Ala Leu Val Gly Gln Val Phe Glu
1               5                   10                  15

Ser Phe Val Leu Glu His His Lys Asn Glu Ile Ala Gln Ile Leu Thr
            20                  25                  30

Glu Lys Glu Glu His Ala His Tyr Ser Leu Val Val Asn Ala Met Thr
        35                  40                  45

Leu Phe Glu Ala Asn Met Glu Ile Gly Glu Tyr Phe Asn Ala Phe Pro
    50                  55                  60

Asn Glu Val Leu Pro Val Phe Asp Asn Ala Leu Arg Cys Ala Ala Met
65                  70                  75                  80

Ser Phe Leu Gln Ser Cys Ser Glu Lys Tyr Thr Phe Leu Met Lys Gln
                85                  90                  95

Asn Leu His Ala Arg Ile Thr Gly Leu Pro Val Cys Pro Glu Leu Thr
            100                 105                 110

Arg Glu His Ile Pro Arg Thr Arg Asp Val Gly His Phe Leu Ser Val
        115                 120                 125
```

```
Thr Gly Thr Val Ile Arg Thr Ser Leu Val Lys Val Leu Glu Tyr Glu
            130                 135                 140

Gln Asp Phe Met Cys Asn Lys Cys Lys His Val Val Thr Val Lys Ala
145                 150                 155                 160

Asp Phe Glu Gln His Tyr Thr Phe Lys Pro Pro Ile Ala Cys Ser Asn
                    165                 170                 175

Glu Glu Gly Cys Asn Ser Thr Lys Phe Thr Cys Leu Ser Asp Ser Ser
                180                 185                 190

Ser Pro Ala Ser Cys Arg Asp Tyr Gln Glu Ile Lys Ile Gln Glu Gln
            195                 200                 205

Val Gln Arg Leu Ser Val Gly Ser Ile Pro Arg Ser Met Ile Val Val
210                 215                 220

Leu Glu Asp Asp Leu Val Asp Ser Cys Lys Ser Gly Asp Asp Ile Thr
225                 230                 235                 240

Val Tyr Gly Val Val Met Gln Arg Trp Lys Pro Leu Tyr Ile Asp Met
                    245                 250                 255

Arg Cys Asp Leu Glu Ile Val Leu Lys Ala Asn Tyr Ile Ser Val Asn
                260                 265                 270

Asn Glu Gln Pro Cys Gly Val Val Ile Asn Glu Glu Val Arg Lys Glu
            275                 280                 285

Tyr Glu Asp Phe Trp Val Lys Tyr Arg Asn Asn Pro Leu Glu Gly Arg
290                 295                 300

Asn Glu Ile Leu Ala Ser Leu Cys Pro Gln Val Phe Gly Met Phe Val
305                 310                 315                 320

Val Lys Leu Ala Val Ala Met Val Leu Ala Gly Gly Val Gln Arg Ile
                    325                 330                 335

Asp Ser Ala Gly Thr Arg Val Arg Gly Glu Ser His Leu Leu Leu Val
                340                 345                 350

Gly Asp Pro Gly Thr Gly Lys Ser Gln Phe Leu Lys Tyr Ala Ala Lys
            355                 360                 365

Ile Thr Pro Arg Ser Val Leu Thr Ala Gly Ile Gly Ser Thr Ser Ala
370                 375                 380

Gly Leu Thr Val Thr Ala Val Lys Asp Ser Gly Glu Trp Asn Leu Glu
385                 390                 395                 400

Ala Gly Ala Leu Val Leu Ala Asp Gly Gly Leu Cys Cys Ile Asp Glu
                    405                 410                 415

Phe Asn Ser Ile Lys Glu His Asp Arg Thr Ser Ile His Glu Ala Met
                420                 425                 430

Glu Gln Gln Thr Ile Ser Val Ala Lys Ala Gly Leu Val Cys Lys Leu
            435                 440                 445

Asn Thr Arg Thr Thr Ile Leu Ala Ala Thr Asn Pro Lys Gly Gln Tyr
450                 455                 460

Asp Pro Asp Glu Ser Ile Ser Val Asn Val Ala Leu Ala Ser Pro Leu
465                 470                 475                 480

Leu Ser Arg Phe Asp Leu Val Leu Val Leu Leu Asp Thr Lys Asn Glu
                    485                 490                 495

Asp Trp Asp Arg Ile Ile Ser Ser Phe Ile Leu Glu Ser Lys Gly Cys
                500                 505                 510

Pro Arg Lys Ser Asp Lys Leu Trp Ser Met Glu Lys Met Lys Thr Tyr
            515                 520                 525

Phe Cys Leu Ile Lys Asn Leu Gln Pro Lys Met Ser Gln Asp Ala Asn
530                 535                 540

Val Ile Leu Val Arg Tyr Tyr Gln Leu Gln Arg Gln Ser Ser Cys Arg
545                 550                 555                 560
```

```
Asn Ala Ala Arg Thr Thr Ile Arg Leu Leu Glu Ser Leu Ile Arg Leu
                565                 570                 575

Ala Glu Ala His Ala Arg Ile Met Tyr Arg Asp Val Val Thr Thr Glu
            580                 585                 590

Asp Ala Ile Thr Val Val Ser Ile Met Glu Ser Ser Met Gln Gly Gly
        595                 600                 605

Ala Leu Leu Gly Gly Val Asn Ala Leu His Thr Ser Phe Pro Glu Asn
    610                 615                 620

Pro Arg Glu Gln Tyr Arg Leu Gln Cys Glu Leu Leu Leu Asp Lys Leu
625                 630                 635                 640

Gly Leu Gln Lys Leu Leu Glu Glu Leu Gln Arg Leu Glu Arg Gln
                645                 650                 655

Gln Ser Glu Asp Ser Leu Glu Ser Asp Leu Gly Glu Ser Ala Thr Asn
            660                 665                 670

Leu Val Gly His Lys Val Val His Ser Glu Cys Val Met Glu Glu Thr
        675                 680                 685

Phe Ser Thr Phe Glu Ala Ser Ser Leu Pro Asp Glu Thr His Leu Gly
    690                 695                 700

Val Thr Gly Ser Ala Ala Phe Ile Gln Thr Pro Lys Lys Thr Ile Ser
705                 710                 715                 720

Asp Met Thr Lys Ser Asp Asp Thr Ile Arg Lys Gly Thr Ile Thr Pro
                725                 730                 735

Ala Glu Gln Asn Arg Gly Ile Ser Thr Asp Ala Glu Ser Ser Leu Lys
            740                 745                 750

Gln Gly Asn Ala Gln Pro Leu Ala Gly Gly His Leu Ser Glu Asn Asn
        755                 760                 765

Leu Thr Lys Cys Thr Asp Asn Ser Leu Gly Trp Phe Asp Thr Leu Gln
    770                 775                 780

Ser Ile Gln Met Ser Pro Ile Thr Lys Gln Arg Glu Gly Cys Thr Ala
785                 790                 795                 800

Glu Lys Leu Gln Gln Glu Val Leu Pro Val Ser Thr Glu Ser Ser Cys
                805                 810                 815

His Pro Ala Asp Lys Lys Val Val Asn Leu Gly Gly Arg Asn Lys Leu
            820                 825                 830

Glu Val Leu Gln Ala Ser Gly Ser Pro Gly Gly Asn Gly Arg Asp
        835                 840                 845

Leu Ser Asn His Thr Val Thr Cys Gly Ser Ser Pro Glu Arg Asn Lys
    850                 855                 860

Arg Asp Leu Ser Asn His Ile Val Thr Glu His Val Ser Lys Lys Trp
865                 870                 875                 880

Arg Arg Ile Asn Lys Asp Ser Leu Cys Gly Lys Asn Val Pro Ser Phe
                885                 890                 895

Gln Pro Gln Ser Glu Asn Thr Asp Ser Ala Pro Val Cys Ser Ser Val
            900                 905                 910

Pro Leu His Ser Thr Pro Asp Val Ala Gln Arg Arg Lys Arg Ile Ile
        915                 920                 925

Ala Gln Val Glu Lys Gln Ser Lys Ala Glu Val Glu Asp Pro Asp Thr
    930                 935                 940

Lys Ala Arg Leu Ala Gln Leu Ala Lys Phe Ser Phe Lys Arg His Ser
945                 950                 955                 960

Lys Leu Val His Ser Pro Ala Gly Asp Thr Asp Thr Ala Ser Asn Ala
                965                 970                 975

Gln Lys His Asp His Pro Val Gln Lys Ile Thr Leu Ser Glu Lys Leu
```

-continued

```
                    980              985                 990
Asn Asn Leu Gly Arg Thr Val Asn  Asn Val Asp Lys Ser  Ser Asn Ser
            995              1000              1005
Val Asn  Gly Ser Lys Gln Gln  Lys His Val Glu Asn  Thr Ser Lys
    1010              1015                  1020
Gln Thr  Val Ile Thr Gln Lys  Ser Asn Phe Glu Ser  Asn Thr Leu
    1025              1030                  1035
Asn Ala  Pro Val His Glu Thr  Lys Leu Asn Glu Gly  Cys Asp Ser
    1040              1045                  1050
Arg Lys  Val Ser Ser Ser Thr  Leu Ala Lys Leu Ala  Arg Phe Ser
    1055              1060                  1065
Phe Ser  Pro Pro Pro Glu Asn  Gln Ala Ala Glu Thr  Ser Lys Glu
    1070              1075                  1080
Thr Leu  Ile Leu Pro Arg Ala  Val Ala Pro Gly Ser  Lys Arg Lys
    1085              1090                  1095
Cys Phe  Glu Leu Asn Pro Ser  Thr Asp Lys Thr Thr  Met Ser Ser
    1100              1105                  1110
Lys Ser  Leu Phe Ser Thr Thr  Asp Leu Asp Asp Glu  Glu Leu Asp
    1115              1120                  1125
Val Asp  Trp Glu Ala Glu Ile  Lys Gly Asn Gln Arg  Ile Ala Thr
    1130              1135                  1140

<210> SEQ ID NO 15
<211> LENGTH: 2280
<212> TYPE: DNA
<213> ORGANISM: Xenopus sp.
<220> FEATURE:
<221> NAME/KEY: CDS
<222> LOCATION: (1)..(2280)

<400> SEQUENCE: 15 ggc ttg act gtt act gca gtg aaa gac tct gga gag tgg aat ctg gag      48
Gly Leu Thr Val Thr Ala Val Lys Asp Ser Gly Glu Trp Asn Leu Glu
1               5                   10                  15 gct gga gcc ttg gtg tta gct gat gga ggc ctg tgc tgc att gat gaa      96
Ala Gly Ala Leu Val Leu Ala Asp Gly Gly Leu Cys Cys Ile Asp Glu
                20                  25                  30 ttt aat agc atc aag gag cat gac aga acc agc atc cat gag gca atg     144
Phe Asn Ser Ile Lys Glu His Asp Arg Thr Ser Ile His Glu Ala Met
            35                  40                  45 gag cag cag acc atc agt gtt gca aag gct ggg tta gtg tgc aag ctg     192
Glu Gln Gln Thr Ile Ser Val Ala Lys Ala Gly Leu Val Cys Lys Leu
        50                  55                  60 aac act agg aca acc att ttg gca gca aca aat ccc aaa ggc caa tat     240
Asn Thr Arg Thr Thr Ile Leu Ala Ala Thr Asn Pro Lys Gly Gln Tyr
65                  70                  75                  80 gac cca gac gaa tcc atc tcg gtg aat gta gcc ctt gct agc cct ctg     288
Asp Pro Asp Glu Ser Ile Ser Val Asn Val Ala Leu Ala Ser Pro Leu
                85                  90                  95 ctc agc aga ttt gac ttg gtt cta gtt ttg ctg gat acc aaa aat gaa     336
Leu Ser Arg Phe Asp Leu Val Leu Val Leu Leu Asp Thr Lys Asn Glu
                100                 105                 110 gac tgg gac cgc att att tct tcg ttt att ttg gag agt aaa ggc tgc     384
Asp Trp Asp Arg Ile Ile Ser Ser Phe Ile Leu Glu Ser Lys Gly Cys
            115                 120                 125 cct cgt aaa tcc gat aag cta tgg agc atg gag aag atg aaa acc tat     432
Pro Arg Lys Ser Asp Lys Leu Trp Ser Met Glu Lys Met Lys Thr Tyr
        130                 135                 140 ttc tgt ctt att aag aat ctt caa ccc aaa atg tct caa gat gct aat     480
```

```
Phe Cys Leu Ile Lys Asn Leu Gln Pro Lys Met Ser Gln Asp Ala Asn
145                 150                 155                 160 gtt atc ctg gta cgt tat tac cag cta cag cgg caa agc agt tgc agg       528
Val Ile Leu Val Arg Tyr Tyr Gln Leu Gln Arg Gln Ser Ser Cys Arg
                165                 170                 175 aat gca gca cgt act act att aga ttg cta gaa agt ttg atc cgc cta       576
Asn Ala Ala Arg Thr Thr Ile Arg Leu Leu Glu Ser Leu Ile Arg Leu
            180                 185                 190 gca gaa gcc cat gct cgg ata atg tat cgg gat gtt gtg acc acc gaa       624
Ala Glu Ala His Ala Arg Ile Met Tyr Arg Asp Val Val Thr Thr Glu
        195                 200                 205 gat gcc ata acc gtg gtg tcc ata atg gag tcc tcg atg cag gga ggt       672
Asp Ala Ile Thr Val Val Ser Ile Met Glu Ser Ser Met Gln Gly Gly
210                 215                 220 gca tta ctt ggc ggt gtc aat gca tta cac aca tcc ttt cca gaa aat       720
Ala Leu Leu Gly Gly Val Asn Ala Leu His Thr Ser Phe Pro Glu Asn
225                 230                 235                 240 cca agg gaa cag tat cgg ctt cag tgc gag ctc cta ttg gat aaa ctt       768
Pro Arg Glu Gln Tyr Arg Leu Gln Cys Glu Leu Leu Leu Asp Lys Leu
                245                 250                 255 ggg ctt cag aaa ttg cta gag gaa gag ctt caa agg cta gaa agg cag       816
Gly Leu Gln Lys Leu Leu Glu Glu Glu Leu Gln Arg Leu Glu Arg Gln
            260                 265                 270 caa agt gaa gac tcc ctt gag tct gat ctt ggg gaa agt gca aca aac       864
Gln Ser Glu Asp Ser Leu Glu Ser Asp Leu Gly Glu Ser Ala Thr Asn
        275                 280                 285 ctc gtt gga cat aaa gta gtg cac agt gag tgt gtc atg gaa gaa acc       912
Leu Val Gly His Lys Val Val His Ser Glu Cys Val Met Glu Glu Thr
    290                 295                 300 ttc agc act ttt gaa gct tct tct ttg cca gat gaa aca cac ctg gga       960
Phe Ser Thr Phe Glu Ala Ser Ser Leu Pro Asp Glu Thr His Leu Gly
305                 310                 315                 320 gta act ggc agt gct gca ttc ata cag act cct aag aaa acc atc tcc      1008
Val Thr Gly Ser Ala Ala Phe Ile Gln Thr Pro Lys Lys Thr Ile Ser
                325                 330                 335 gat atg acc aaa agt gat gac acc att agg aag ggt acc att aca cct      1056
Asp Met Thr Lys Ser Asp Asp Thr Ile Arg Lys Gly Thr Ile Thr Pro
            340                 345                 350 gct gaa caa aac aga ggt att agc aca gat gcc gag tcc tct tta aaa      1104
Ala Glu Gln Asn Arg Gly Ile Ser Thr Asp Ala Glu Ser Ser Leu Lys
        355                 360                 365 caa ggt aat gca caa cca ctc gct ggt ggg cat ctc tct gaa aat aat      1152
Gln Gly Asn Ala Gln Pro Leu Ala Gly Gly His Leu Ser Glu Asn Asn
370                 375                 380 ctt aca aaa tgc act gat aac agt ctt ggc tgg ttt gat aca ctt caa      1200
Leu Thr Lys Cys Thr Asp Asn Ser Leu Gly Trp Phe Asp Thr Leu Gln
385                 390                 395                 400 tcc att cag atg tct ccc atc acc aaa caa aga gaa gga tgc aca gct      1248
Ser Ile Gln Met Ser Pro Ile Thr Lys Gln Arg Glu Gly Cys Thr Ala
                405                 410                 415 gaa aag ctt caa caa gaa gtc ctt cct gta tca aca gaa agt agc tgc      1296
Glu Lys Leu Gln Gln Glu Val Leu Pro Val Ser Thr Glu Ser Ser Cys
            420                 425                 430 cat cct gca gac aaa aaa gtt gta aat tta gga ggg agg aac aaa ctt      1344
His Pro Ala Asp Lys Lys Val Val Asn Leu Gly Gly Arg Asn Lys Leu
        435                 440                 445 gaa gtt ttg caa gct agt gga agc agc cct ggg gga aat gga agg gat      1392
Glu Val Leu Gln Ala Ser Gly Ser Ser Pro Gly Gly Asn Gly Arg Asp
450                 455                 460 ttg tca aat cac aca gtg act tgt gga agc agc cct gag aga aac aaa      1440
Leu Ser Asn His Thr Val Thr Cys Gly Ser Ser Pro Glu Arg Asn Lys
```

```
Leu Ser Asn His Thr Val Thr Cys Gly Ser Ser Pro Glu Arg Asn Lys
465                 470                 475                 480 aga gat ttg tca aat cac ata gtg act gag cat gtt tct aaa aag tgg    1488
Arg Asp Leu Ser Asn His Ile Val Thr Glu His Val Ser Lys Lys Trp
                485                 490                 495 cgg aga ata aat aaa gat tcc ctt tgt gga aaa aat gtg cca tct ttc    1536
Arg Arg Ile Asn Lys Asp Ser Leu Cys Gly Lys Asn Val Pro Ser Phe
            500                 505                 510 cag cct cag tct gaa aat aca gat tcg gct cca gtc tgc tcc agt gtt    1584
Gln Pro Gln Ser Glu Asn Thr Asp Ser Ala Pro Val Cys Ser Ser Val
        515                 520                 525 cct ctg cat agt acc cct gat gtt gcc cag aga agg aaa aga att att    1632
Pro Leu His Ser Thr Pro Asp Val Ala Gln Arg Arg Lys Arg Ile Ile
    530                 535                 540 gcc cag gtg gaa aag caa tcg aaa gca gaa gtg gag gat cca gac aca    1680
Ala Gln Val Glu Lys Gln Ser Lys Ala Glu Val Glu Asp Pro Asp Thr
545                 550                 555                 560 aaa gca cga cta gcc cag ttg gcc aag ttt tca ttt aag cga cat tca    1728
Lys Ala Arg Leu Ala Gln Leu Ala Lys Phe Ser Phe Lys Arg His Ser
                565                 570                 575 aaa ctg gtg cat tca cct gca ggg gat act gac aca gca tca aat gca    1776
Lys Leu Val His Ser Pro Ala Gly Asp Thr Asp Thr Ala Ser Asn Ala
            580                 585                 590 cag aaa cat gat cac cca gtc cag aaa att aca cta tca gag aag ttg    1824
Gln Lys His Asp His Pro Val Gln Lys Ile Thr Leu Ser Glu Lys Leu
        595                 600                 605 aac aat tta ggt agg act gta aat aat gtg gat aaa tca agc aat tct    1872
Asn Asn Leu Gly Arg Thr Val Asn Asn Val Asp Lys Ser Ser Asn Ser
    610                 615                 620 gtt aat ggc tca aag cag caa aag cat gta gag aat aca tcc aaa cag    1920
Val Asn Gly Ser Lys Gln Gln Lys His Val Glu Asn Thr Ser Lys Gln
625                 630                 635                 640 act gta ata acg cag aag agt aac ttt gaa tcg aac aca tta aac gct    1968
Thr Val Ile Thr Gln Lys Ser Asn Phe Glu Ser Asn Thr Leu Asn Ala
                645                 650                 655 cct gtg cat gag aca aag ttg aat gag ggg tgt gac tcc aga aag gtt    2016
Pro Val His Glu Thr Lys Leu Asn Glu Gly Cys Asp Ser Arg Lys Val
            660                 665                 670 tct tct agt aca ctt gct aag tta gca cgc ttt tct ttc tca cct cct    2064
Ser Ser Ser Thr Leu Ala Lys Leu Ala Arg Phe Ser Phe Ser Pro Pro
        675                 680                 685 cct gaa aat caa gca gcg gag acc agc aag gaa acc ctg att tta cca    2112
Pro Glu Asn Gln Ala Ala Glu Thr Ser Lys Glu Thr Leu Ile Leu Pro
    690                 695                 700 aga gct gtt gct cca ggc agc aaa aga aag tgt ttt gaa ctg aat cct    2160
Arg Ala Val Ala Pro Gly Ser Lys Arg Lys Cys Phe Glu Leu Asn Pro
705                 710                 715                 720 tcc act gat aaa acc aca atg tca agt aaa tct ctt ttc tct aca aca    2208
Ser Thr Asp Lys Thr Thr Met Ser Ser Lys Ser Leu Phe Ser Thr Thr
                725                 730                 735 gac tta gat gat gaa gag tta gat gtg gat tgg gag gct gaa ata aaa    2256
Asp Leu Asp Asp Glu Glu Leu Asp Val Asp Trp Glu Ala Glu Ile Lys
            740                 745                 750 gga aat cag aga att gcc aca tga                                    2280
Gly Asn Gln Arg Ile Ala Thr
        755

<210> SEQ ID NO 16
<211> LENGTH: 759
<212> TYPE: PRT
<213> ORGANISM: Xenopus sp.
```

<400> SEQUENCE: 16

```
Gly Leu Thr Val Thr Ala Val Lys Asp Ser Gly Glu Trp Asn Leu Glu
1               5                   10                  15

Ala Gly Ala Leu Val Leu Ala Asp Gly Gly Leu Cys Cys Ile Asp Glu
            20                  25                  30

Phe Asn Ser Ile Lys Glu His Asp Arg Thr Ser Ile His Glu Ala Met
            35                  40                  45

Glu Gln Gln Thr Ile Ser Val Ala Lys Ala Gly Leu Val Cys Lys Leu
        50                  55                  60

Asn Thr Arg Thr Thr Ile Leu Ala Ala Thr Asn Pro Lys Gly Gln Tyr
65                  70                  75                  80

Asp Pro Asp Glu Ser Ile Ser Val Asn Val Ala Leu Ala Ser Pro Leu
                85                  90                  95

Leu Ser Arg Phe Asp Leu Val Leu Val Leu Leu Asp Thr Lys Asn Glu
            100                 105                 110

Asp Trp Asp Arg Ile Ile Ser Ser Phe Ile Leu Glu Ser Lys Gly Cys
        115                 120                 125

Pro Arg Lys Ser Asp Lys Leu Trp Ser Met Glu Lys Met Lys Thr Tyr
130                 135                 140

Phe Cys Leu Ile Lys Asn Leu Gln Pro Lys Met Ser Gln Asp Ala Asn
145                 150                 155                 160

Val Ile Leu Val Arg Tyr Tyr Gln Leu Gln Arg Gln Ser Ser Cys Arg
                165                 170                 175

Asn Ala Ala Arg Thr Thr Ile Arg Leu Leu Glu Ser Leu Ile Arg Leu
            180                 185                 190

Ala Glu Ala His Ala Arg Ile Met Tyr Arg Asp Val Val Thr Thr Glu
        195                 200                 205

Asp Ala Ile Thr Val Val Ser Ile Met Glu Ser Ser Met Gln Gly Gly
    210                 215                 220

Ala Leu Leu Gly Gly Val Asn Ala Leu His Thr Ser Phe Pro Glu Asn
225                 230                 235                 240

Pro Arg Glu Gln Tyr Arg Leu Gln Cys Glu Leu Leu Leu Asp Lys Leu
                245                 250                 255

Gly Leu Gln Lys Leu Leu Glu Glu Leu Gln Arg Leu Glu Arg Gln
            260                 265                 270

Gln Ser Glu Asp Ser Leu Glu Ser Asp Leu Gly Glu Ser Ala Thr Asn
        275                 280                 285

Leu Val Gly His Lys Val Val His Ser Glu Cys Val Met Glu Glu Thr
    290                 295                 300

Phe Ser Thr Phe Glu Ala Ser Ser Leu Pro Asp Glu Thr His Leu Gly
305                 310                 315                 320

Val Thr Gly Ser Ala Ala Phe Ile Gln Thr Pro Lys Lys Thr Ile Ser
                325                 330                 335

Asp Met Thr Lys Ser Asp Asp Thr Ile Arg Lys Gly Thr Ile Thr Pro
            340                 345                 350

Ala Glu Gln Asn Arg Gly Ile Ser Thr Asp Ala Glu Ser Ser Leu Lys
        355                 360                 365

Gln Gly Asn Ala Gln Pro Leu Ala Gly His Leu Ser Glu Asn Asn
    370                 375                 380

Leu Thr Lys Cys Thr Asp Asn Ser Leu Gly Trp Phe Asp Thr Leu Gln
385                 390                 395                 400

Ser Ile Gln Met Ser Pro Ile Thr Lys Gln Arg Glu Gly Cys Thr Ala
                405                 410                 415
```

Glu Lys Leu Gln Gln Glu Val Leu Pro Val Ser Thr Glu Ser Ser Cys
                420                 425                 430

His Pro Ala Asp Lys Lys Val Asn Leu Gly Gly Arg Asn Lys Leu
            435                 440                 445

Glu Val Leu Gln Ala Ser Gly Ser Ser Pro Gly Gly Asn Gly Arg Asp
450                 455                 460

Leu Ser Asn His Thr Val Thr Cys Gly Ser Ser Pro Glu Arg Asn Lys
465                 470                 475                 480

Arg Asp Leu Ser Asn His Ile Val Thr Glu His Val Ser Lys Lys Trp
                485                 490                 495

Arg Arg Ile Asn Lys Asp Ser Leu Cys Gly Lys Asn Val Pro Ser Phe
                500                 505                 510

Gln Pro Gln Ser Glu Asn Thr Asp Ser Ala Pro Val Cys Ser Ser Val
            515                 520                 525

Pro Leu His Ser Thr Pro Asp Val Ala Gln Arg Arg Lys Arg Ile Ile
            530                 535                 540

Ala Gln Val Glu Lys Gln Ser Lys Ala Glu Val Glu Asp Pro Asp Thr
545                 550                 555                 560

Lys Ala Arg Leu Ala Gln Leu Ala Lys Phe Ser Phe Lys Arg His Ser
                565                 570                 575

Lys Leu Val His Ser Pro Ala Gly Asp Thr Asp Thr Ala Ser Asn Ala
            580                 585                 590

Gln Lys His Asp His Pro Val Gln Lys Ile Thr Leu Ser Glu Lys Leu
            595                 600                 605

Asn Asn Leu Gly Arg Thr Val Asn Val Asp Lys Ser Ser Asn Ser
610                 615                 620

Val Asn Gly Ser Lys Gln Lys His Val Glu Asn Thr Ser Lys Gln
625                 630                 635                 640

Thr Val Ile Thr Gln Lys Ser Asn Phe Glu Ser Asn Thr Leu Asn Ala
                645                 650                 655

Pro Val His Glu Thr Lys Leu Asn Glu Gly Cys Asp Ser Arg Lys Val
            660                 665                 670

Ser Ser Ser Thr Leu Ala Lys Leu Ala Arg Phe Ser Phe Ser Pro Pro
            675                 680                 685

Pro Glu Asn Gln Ala Ala Glu Thr Ser Lys Glu Thr Leu Ile Leu Pro
            690                 695                 700

Arg Ala Val Ala Pro Gly Ser Lys Arg Lys Cys Phe Glu Leu Asn Pro
705                 710                 715                 720

Ser Thr Asp Lys Thr Thr Met Ser Ser Lys Ser Leu Phe Ser Thr Thr
                725                 730                 735

Asp Leu Asp Asp Glu Glu Leu Asp Val Asp Trp Glu Ala Glu Ile Lys
            740                 745                 750

Gly Asn Gln Arg Ile Ala Thr
            755

<210> SEQ ID NO 17
<211> LENGTH: 1152
<212> TYPE: DNA
<213> ORGANISM: Xenopus sp.
<220> FEATURE:
<221> NAME/KEY: CDS
<222> LOCATION: (1)..(1152)

<400> SEQUENCE: 17 atg tat ctc ggt ttt gaa caa gta gcg ctg gtg ggc caa gtc ttt gaa     48
Met Tyr Leu Gly Phe Glu Gln Val Ala Leu Val Gly Gln Val Phe Glu -continued

```
 1               5                  10                 15
tcc ttt gtg ctg gag cac cac aaa aat gag att gcc cag ata ctt act    96
Ser Phe Val Leu Glu His His Lys Asn Glu Ile Ala Gln Ile Leu Thr
             20                  25                 30 gag aaa gaa gag cat gcc cac tac tca ctg gtt gtt aat gcc atg aca   144
Glu Lys Glu Glu His Ala His Tyr Ser Leu Val Val Asn Ala Met Thr
             35                  40                 45 ctt ttt gaa gca aac atg gag att gga gag tac ttt aat gcc ttt cca   192
Leu Phe Glu Ala Asn Met Glu Ile Gly Glu Tyr Phe Asn Ala Phe Pro
 50                  55                 60 aat gaa gtt ctg ccc gtc ttt gat aat gct ctg cgc tgt gct gcc atg   240
Asn Glu Val Leu Pro Val Phe Asp Asn Ala Leu Arg Cys Ala Ala Met
 65                  70                 75                 80 agc ttt ctt cag tct tgt tca gaa aaa tac aca ttt ctt atg aag cag   288
Ser Phe Leu Gln Ser Cys Ser Glu Lys Tyr Thr Phe Leu Met Lys Gln
                 85                  90                 95 aat ctt cat gca agg ata aca ggt cta cca gtg tgc cca gag tta acc   336
Asn Leu His Ala Arg Ile Thr Gly Leu Pro Val Cys Pro Glu Leu Thr
            100                 105                110 aga gag cac ata cca cga acc aga gat gtg ggg cat ttc ctt tct gta   384
Arg Glu His Ile Pro Arg Thr Arg Asp Val Gly His Phe Leu Ser Val
            115                 120                125 acc ggt aca gta att cgc acc agc ttg gtt aaa gtg ctc gag tat gag   432
Thr Gly Thr Val Ile Arg Thr Ser Leu Val Lys Val Leu Glu Tyr Glu
            130                 135                140 caa gac ttc atg tgc aac aag tgt aag cat gtg gtc act gtg aaa gca   480
Gln Asp Phe Met Cys Asn Lys Cys Lys His Val Val Thr Val Lys Ala
145                 150                 155                160 gac ttt gag cag cat tac aca ttc aag cca ccc atc gct tgc tca aat   528
Asp Phe Glu Gln His Tyr Thr Phe Lys Pro Pro Ile Ala Cys Ser Asn
                165                 170                175 gag gaa ggc tgc aac tcc acc aaa ttc acc tgt ctg tca gat tca tcc   576
Glu Glu Gly Cys Asn Ser Thr Lys Phe Thr Cys Leu Ser Asp Ser Ser
            180                 185                190 tct cca gcc agc tgc aga gac tat caa gag atc aag att cag gaa cag   624
Ser Pro Ala Ser Cys Arg Asp Tyr Gln Glu Ile Lys Ile Gln Glu Gln
            195                 200                205 gtt caa agg cta tct gtt ggc agt atc cct cga tca atg att gta gtt   672
Val Gln Arg Leu Ser Val Gly Ser Ile Pro Arg Ser Met Ile Val Val
            210                 215                220 ttg gaa gat gac ctg gtt gac agc tgc aaa tct gga gat gat ata aca   720
Leu Glu Asp Asp Leu Val Asp Ser Cys Lys Ser Gly Asp Asp Ile Thr
225                 230                 235                240 gtc tat ggt gtg gtg atg cag cgg tgg aaa ccc ctt tat ata gac atg   768
Val Tyr Gly Val Val Met Gln Arg Trp Lys Pro Leu Tyr Ile Asp Met
                245                 250                255 cgc tgt gac ctg gaa att gtt tta aag gcc aat tac att tca gtc aat   816
Arg Cys Asp Leu Glu Ile Val Leu Lys Ala Asn Tyr Ile Ser Val Asn
            260                 265                270 aat gag caa cct tgt ggt gtg gtt ata aat gaa gaa gta cgc aaa gag   864
Asn Glu Gln Pro Cys Gly Val Val Ile Asn Glu Glu Val Arg Lys Glu
            275                 280                285 tat gaa gat ttc tgg gtg aag tat agg aac aac cct tta gaa ggt agg   912
Tyr Glu Asp Phe Trp Val Lys Tyr Arg Asn Asn Pro Leu Glu Gly Arg
            290                 295                300 aat gaa att ctg gcc agc ctg tgt ccg cag gta ttt ggt atg ttt gta   960
Asn Glu Ile Leu Ala Ser Leu Cys Pro Gln Val Phe Gly Met Phe Val
305                 310                 315                320 gtg aag ctg gca gtg gcc atg gtg ctg gct ggt gga gtt cag aga att  1008
Val Lys Leu Ala Val Ala Met Val Leu Ala Gly Gly Val Gln Arg Ile
```

```
                      325                 330                 335
gat tct gct gga aca aga gtg aga ggt gag tca cat ctt ctg cta gtt     1056
Asp Ser Ala Gly Thr Arg Val Arg Gly Glu Ser His Leu Leu Leu Val
            340                 345                 350 gga gac cct ggc acg ggg aaa tca cag ttt ctg aag tat gct gca aaa     1104
Gly Asp Pro Gly Thr Gly Lys Ser Gln Phe Leu Lys Tyr Ala Ala Lys
                355                 360                 365 att act ccg agg tct gtc ctt act gca ggc att gga tct act agt gca     1152
Ile Thr Pro Arg Ser Val Leu Thr Ala Gly Ile Gly Ser Thr Ser Ala
        370                 375                 380

<210> SEQ ID NO 18
<211> LENGTH: 384
<212> TYPE: PRT
<213> ORGANISM: Xenopus sp.

<400> SEQUENCE: 18

Met Tyr Leu Gly Phe Glu Gln Val Ala Leu Val Gly Gln Val Phe Glu
1               5                   10                  15

Ser Phe Val Leu Glu His His Lys Asn Glu Ile Ala Gln Ile Leu Thr
            20                  25                  30

Glu Lys Glu Glu His Ala His Tyr Ser Leu Val Val Asn Ala Met Thr
        35                  40                  45

Leu Phe Glu Ala Asn Met Glu Ile Gly Glu Tyr Phe Asn Ala Phe Pro
    50                  55                  60

Asn Glu Val Leu Pro Val Phe Asp Asn Ala Leu Arg Cys Ala Ala Met
65                  70                  75                  80

Ser Phe Leu Gln Ser Cys Ser Glu Lys Tyr Thr Phe Leu Met Lys Gln
                85                  90                  95

Asn Leu His Ala Arg Ile Thr Gly Leu Pro Val Cys Pro Glu Leu Thr
            100                 105                 110

Arg Glu His Ile Pro Arg Thr Arg Asp Val Gly His Phe Leu Ser Val
        115                 120                 125

Thr Gly Thr Val Ile Arg Thr Ser Leu Val Lys Val Leu Glu Tyr Glu
    130                 135                 140

Gln Asp Phe Met Cys Asn Lys Cys Lys His Val Val Thr Val Lys Ala
145                 150                 155                 160

Asp Phe Glu Gln His Tyr Thr Phe Lys Pro Pro Ile Ala Cys Ser Asn
                165                 170                 175

Glu Glu Gly Cys Asn Ser Thr Lys Phe Thr Cys Leu Ser Asp Ser Ser
            180                 185                 190

Ser Pro Ala Ser Cys Arg Asp Tyr Gln Glu Ile Lys Ile Gln Glu Gln
        195                 200                 205

Val Gln Arg Leu Ser Val Gly Ser Ile Pro Arg Ser Met Ile Val Val
    210                 215                 220

Leu Glu Asp Asp Leu Val Asp Ser Cys Lys Ser Gly Asp Asp Ile Thr
225                 230                 235                 240

Val Tyr Gly Val Val Met Gln Arg Trp Lys Pro Leu Tyr Ile Asp Met
                245                 250                 255

Arg Cys Asp Leu Glu Ile Val Leu Lys Ala Asn Tyr Ile Ser Val Asn
            260                 265                 270

Asn Glu Gln Pro Cys Gly Val Ile Asn Glu Glu Val Arg Lys Glu
        275                 280                 285

Tyr Glu Asp Phe Trp Val Lys Tyr Arg Asn Asn Pro Leu Glu Gly Arg
    290                 295                 300

Asn Glu Ile Leu Ala Ser Leu Cys Pro Gln Val Phe Gly Met Phe Val
```

```
                 305                 310                 315                 320
Val Lys Leu Ala Val Ala Met Val Leu Ala Gly Gly Val Gln Arg Ile
            325                 330                 335

Asp Ser Ala Gly Thr Arg Val Arg Gly Glu Ser His Leu Leu Leu Val
            340                 345                 350

Gly Asp Pro Gly Thr Gly Lys Ser Gln Phe Leu Lys Tyr Ala Ala Lys
            355                 360                 365

Ile Thr Pro Arg Ser Val Leu Thr Ala Gly Ile Gly Thr Ser Ala
            370                 375                 380

<210> SEQ ID NO 19
<211> LENGTH: 453
<212> TYPE: DNA
<213> ORGANISM: Homo sapiens
<220> FEATURE:
<221> NAME/KEY: CDS
<222> LOCATION: (1)..(453)

<400> SEQUENCE: 19 ttt gca gga agg aat gta ata ttg gct agc ttg tgc cct caa gtg ttt      48
Phe Ala Gly Arg Asn Val Ile Leu Ala Ser Leu Cys Pro Gln Val Phe
1               5                   10                  15 gga atg tat cta gta aag ctt gct gtg gcc atg gtg ctg gct ggt ggg      96
Gly Met Tyr Leu Val Lys Leu Ala Val Ala Met Val Leu Ala Gly Gly
            20                  25                  30 att caa agg act gat gct aca gga aca cgg gtc aga gga gaa tct cat     144
Ile Gln Arg Thr Asp Ala Thr Gly Thr Arg Val Arg Gly Glu Ser His
        35                  40                  45 ctt tta ttg gtt ggg gat cct ggc aca ggg aaa tct cag ttc ctc aaa     192
Leu Leu Leu Val Gly Asp Pro Gly Thr Gly Lys Ser Gln Phe Leu Lys
    50                  55                  60 tat gca gca aag att aca cca aga tct gtg ctg acc aca gga att gga     240
Tyr Ala Ala Lys Ile Thr Pro Arg Ser Val Leu Thr Thr Gly Ile Gly
65                  70                  75                  80 tct act agt gca ggt ctg acg gta act gct gta aaa gac tca gga gaa     288
Ser Thr Ser Ala Gly Leu Thr Val Thr Ala Val Lys Asp Ser Gly Glu
                85                  90                  95 tgg aat ttg gag gct ggg gca tta gtt ctt gca gat gcg ggc ctt tgc     336
Trp Asn Leu Glu Ala Gly Ala Leu Val Leu Ala Asp Ala Gly Leu Cys
            100                 105                 110 tgt att gat gag ttc aat agc ctc aaa gag cat gat agg acc agt atc     384
Cys Ile Asp Glu Phe Asn Ser Leu Lys Glu His Asp Arg Thr Ser Ile
        115                 120                 125 cat gaa gca atg gag caa caa acc ata agt gtt gct aag gct ggc ctc     432
His Glu Ala Met Glu Gln Gln Thr Ile Ser Val Ala Lys Ala Gly Leu
    130                 135                 140 gtg tgc aag ctg aac aca agg                                         453
Val Cys Lys Leu Asn Thr Arg
145                 150

<210> SEQ ID NO 20
<211> LENGTH: 151
<212> TYPE: PRT
<213> ORGANISM: Homo sapiens

<400> SEQUENCE: 20

Phe Ala Gly Arg Asn Val Ile Leu Ala Ser Leu Cys Pro Gln Val Phe
1               5                   10                  15

Gly Met Tyr Leu Val Lys Leu Ala Val Ala Met Val Leu Ala Gly Gly
            20                  25                  30

Ile Gln Arg Thr Asp Ala Thr Gly Thr Arg Val Arg Gly Glu Ser His
```

```
                 35                  40                  45
Leu Leu Leu Val Gly Asp Pro Gly Thr Gly Lys Ser Gln Phe Leu Lys
 50                  55                  60

Tyr Ala Ala Lys Ile Thr Pro Arg Ser Val Leu Thr Thr Gly Ile Gly
 65                  70                  75                  80

Ser Thr Ser Ala Gly Leu Thr Val Thr Ala Val Lys Asp Ser Gly Glu
                 85                  90                  95

Trp Asn Leu Glu Ala Gly Ala Leu Val Leu Ala Asp Ala Gly Leu Cys
                100                 105                 110

Cys Ile Asp Glu Phe Asn Ser Leu Lys Glu His Asp Arg Thr Ser Ile
                115                 120                 125

His Glu Ala Met Glu Gln Gln Thr Ile Ser Val Ala Lys Ala Gly Leu
    130                 135                 140

Val Cys Lys Leu Asn Thr Arg
145                 150

<210> SEQ ID NO 21
<211> LENGTH: 363
<212> TYPE: DNA
<213> ORGANISM: Homo sapiens
<220> FEATURE:
<221> NAME/KEY: CDS
<222> LOCATION: (1)..(363)

<400> SEQUENCE: 21 ttg tgc cct caa gtg ttt gga atg tat cta gta aag ctt gct gtg gcc       48
Leu Cys Pro Gln Val Phe Gly Met Tyr Leu Val Lys Leu Ala Val Ala
 1               5                  10                  15 atg gtg ctg gct ggt ggg att caa agg act gat gct aca gga aca cgg       96
Met Val Leu Ala Gly Gly Ile Gln Arg Thr Asp Ala Thr Gly Thr Arg
             20                  25                  30 gtc aga gga gaa tct cat ctt tta ttg gtt ggg gat cct ggc aca ggg      144
Val Arg Gly Glu Ser His Leu Leu Leu Val Gly Asp Pro Gly Thr Gly
         35                  40                  45 aaa tct cag ttc ctc aaa tat gca gca aag att aca cca aga tct gtg      192
Lys Ser Gln Phe Leu Lys Tyr Ala Ala Lys Ile Thr Pro Arg Ser Val
 50                  55                  60 ctg acc aca gga att gga tct act agt gca ggt ctg acg gta act gct      240
Leu Thr Thr Gly Ile Gly Ser Thr Ser Ala Gly Leu Thr Val Thr Ala
 65                  70                  75                  80 gta aaa gac tca gga gaa tgg aat ttg gag gct ggg gca tta gtt ctt      288
Val Lys Asp Ser Gly Glu Trp Asn Leu Glu Ala Gly Ala Leu Val Leu
                 85                  90                  95 gca gat gcg ggc ctt tgc tgt att gat gag ttc aat agc ctc aaa gag      336
Ala Asp Ala Gly Leu Cys Cys Ile Asp Glu Phe Asn Ser Leu Lys Glu
                100                 105                 110 cat gat agg acc agt atc cat gaa gca                                  363
His Asp Arg Thr Ser Ile His Glu Ala
            115                 120

<210> SEQ ID NO 22
<211> LENGTH: 121
<212> TYPE: PRT
<213> ORGANISM: Homo sapiens

<400> SEQUENCE: 22

Leu Cys Pro Gln Val Phe Gly Met Tyr Leu Val Lys Leu Ala Val Ala
 1               5                  10                  15

Met Val Leu Ala Gly Gly Ile Gln Arg Thr Asp Ala Thr Gly Thr Arg
             20                  25                  30
```

Val Arg Gly Glu Ser His Leu Leu Val Gly Asp Pro Gly Thr Gly
             35                  40                  45

Lys Ser Gln Phe Leu Lys Tyr Ala Ala Lys Ile Thr Pro Arg Ser Val
 50                  55                  60

Leu Thr Thr Gly Ile Gly Ser Thr Ser Ala Gly Leu Thr Val Thr Ala
 65                  70                  75                  80

Val Lys Asp Ser Gly Glu Trp Asn Leu Glu Ala Gly Ala Leu Val Leu
                 85                  90                  95

Ala Asp Ala Gly Leu Cys Cys Ile Asp Glu Phe Asn Ser Leu Lys Glu
                100                 105                 110

His Asp Arg Thr Ser Ile His Glu Ala
            115                 120

<210> SEQ ID NO 23
<211> LENGTH: 198
<212> TYPE: DNA
<213> ORGANISM: Homo sapiens
<220> FEATURE:
<221> NAME/KEY: CDS
<222> LOCATION: (1)..(198)

<400> SEQUENCE: 23 ggg gat cct ggc aca ggg aaa tct cag ttc ctc aaa tat gca gca aag     48
Gly Asp Pro Gly Thr Gly Lys Ser Gln Phe Leu Lys Tyr Ala Ala Lys
 1               5                  10                  15 att aca cca aga tct gtg ctg acc aca gga att gga tct act agt gca     96
Ile Thr Pro Arg Ser Val Leu Thr Thr Gly Ile Gly Ser Thr Ser Ala
             20                  25                  30 ggt ctg acg gta act gct gta aaa gac tca gga gaa tgg aat ttg gag    144
Gly Leu Thr Val Thr Ala Val Lys Asp Ser Gly Glu Trp Asn Leu Glu
         35                  40                  45 gct ggg gca tta gtt ctt gca gat gcg ggc ctt tgc tgt att gat gag    192
Ala Gly Ala Leu Val Leu Ala Asp Ala Gly Leu Cys Cys Ile Asp Glu
     50                  55                  60 ttc aat                                                            198
Phe Asn
 65

<210> SEQ ID NO 24
<211> LENGTH: 66
<212> TYPE: PRT
<213> ORGANISM: Homo sapiens

<400> SEQUENCE: 24

Gly Asp Pro Gly Thr Gly Lys Ser Gln Phe Leu Lys Tyr Ala Ala Lys
 1               5                  10                  15

Ile Thr Pro Arg Ser Val Leu Thr Thr Gly Ile Gly Ser Thr Ser Ala
             20                  25                  30

Gly Leu Thr Val Thr Ala Val Lys Asp Ser Gly Glu Trp Asn Leu Glu
         35                  40                  45

Ala Gly Ala Leu Val Leu Ala Asp Ala Gly Leu Cys Cys Ile Asp Glu
     50                  55                  60

Phe Asn
 65

<210> SEQ ID NO 25
<211> LENGTH: 453
<212> TYPE: DNA
<213> ORGANISM: Mus musculus
<220> FEATURE:
<221> NAME/KEY: CDS
<222> LOCATION: (4)..(453)

-continued

<400> SEQUENCE: 25

```
aat gaa ata ttg gcc agc ttg tgt cct caa gtt ttt ggg atg tat cta    48
    Glu Ile Leu Ala Ser Leu Cys Pro Gln Val Phe Gly Met Tyr Leu
        1               5                  10                  15 gtg aag ctt gct gtg gcc atg gta ctg gct ggt gga att caa aga act    96
Val Lys Leu Ala Val Ala Met Val Leu Ala Gly Gly Ile Gln Arg Thr
                    20                  25                  30 gat gct gca gga acc agg gtt aga ggg gaa tct cac ctt tta ttg gtt   144
Asp Ala Ala Gly Thr Arg Val Arg Gly Glu Ser His Leu Leu Leu Val
                35                  40                  45 ggg gat cct ggc aca ggg aaa tca caa ttc ctt aaa tat gca gca aag   192
Gly Asp Pro Gly Thr Gly Lys Ser Gln Phe Leu Lys Tyr Ala Ala Lys
            50                  55                  60 att acc cca agg tcc gtt ttg acc aca gga att gga tct act agt gca   240
Ile Thr Pro Arg Ser Val Leu Thr Thr Gly Ile Gly Ser Thr Ser Ala
65                  70                  75 ggt ctg acc gtg aca gct gtc aaa gac tca gga gaa tgg aat cta gag   288
Gly Leu Thr Val Thr Ala Val Lys Asp Ser Gly Glu Trp Asn Leu Glu
 80                  85                  90                  95 gct ggg gct ttg gtg ctt gca gat gct ggt ctc tgc tgt att gac gaa   336
Ala Gly Ala Leu Val Leu Ala Asp Ala Gly Leu Cys Cys Ile Asp Glu
                    100                 105                 110 ttt aac agc ctc aaa gaa cat gac agg aca agc atc cat gaa gca atg   384
Phe Asn Ser Leu Lys Glu His Asp Arg Thr Ser Ile His Glu Ala Met
                115                 120                 125 gag caa caa acc ata agt gtt gct aag gct ggc ctt gtt tgt aag ctg   432
Glu Gln Gln Thr Ile Ser Val Ala Lys Ala Gly Leu Val Cys Lys Leu
            130                 135                 140 aac aca agg acc acc atc ctg                                       453
Asn Thr Arg Thr Thr Ile Leu
            145                 150
```

<210> SEQ ID NO 26
<211> LENGTH: 150
<212> TYPE: PRT
<213> ORGANISM: Mus musculus

<400> SEQUENCE: 26

```
Glu Ile Leu Ala Ser Leu Cys Pro Gln Val Phe Gly Met Tyr Leu Val
1               5                  10                  15

Lys Leu Ala Val Ala Met Val Leu Ala Gly Gly Ile Gln Arg Thr Asp
                20                  25                  30

Ala Ala Gly Thr Arg Val Arg Gly Glu Ser His Leu Leu Leu Val Gly
            35                  40                  45

Asp Pro Gly Thr Gly Lys Ser Gln Phe Leu Lys Tyr Ala Ala Lys Ile
        50                  55                  60

Thr Pro Arg Ser Val Leu Thr Thr Gly Ile Gly Ser Thr Ser Ala Gly
65                  70                  75                  80

Leu Thr Val Thr Ala Val Lys Asp Ser Gly Glu Trp Asn Leu Glu Ala
                85                  90                  95

Gly Ala Leu Val Leu Ala Asp Ala Gly Leu Cys Cys Ile Asp Glu Phe
            100                 105                 110

Asn Ser Leu Lys Glu His Asp Arg Thr Ser Ile His Glu Ala Met Glu
        115                 120                 125

Gln Gln Thr Ile Ser Val Ala Lys Ala Gly Leu Val Cys Lys Leu Asn
    130                 135                 140

Thr Arg Thr Thr Ile Leu
145                 150
```

<210> SEQ ID NO 27
<211> LENGTH: 363
<212> TYPE: DNA
<213> ORGANISM: Mus musculus
<220> FEATURE:
<221> NAME/KEY: CDS
<222> LOCATION: (1)..(363)

<400> SEQUENCE: 27

| | | | | | | | | | | | | | | | | |
|---|---|---|---|---|---|---|---|---|---|---|---|---|---|---|---|---|
| gtt | ttt | ggg | atg | tat | cta | gtg | aag | ctt | gct | gtg | gcc | atg | gta | ctg | gct | 48 |
| Val | Phe | Gly | Met | Tyr | Leu | Val | Lys | Leu | Ala | Val | Ala | Met | Val | Leu | Ala | |
| 1 | | | | 5 | | | | | 10 | | | | | 15 | | |
| ggt | gga | att | caa | aga | act | gat | gct | gca | gga | acc | agg | gtt | aga | ggg | gaa | 96 |
| Gly | Gly | Ile | Gln | Arg | Thr | Asp | Ala | Ala | Gly | Thr | Arg | Val | Arg | Gly | Glu | |
| | | | 20 | | | | | 25 | | | | | 30 | | | |
| tct | cac | ctt | tta | ttg | gtt | ggg | gat | cct | ggc | aca | ggg | aaa | tca | caa | ttc | 144 |
| Ser | His | Leu | Leu | Leu | Val | Gly | Asp | Pro | Gly | Thr | Gly | Lys | Ser | Gln | Phe | |
| | | 35 | | | | | 40 | | | | | 45 | | | | |
| ctt | aaa | tat | gca | gca | aag | att | acc | cca | agg | tcc | gtt | ttg | acc | aca | gga | 192 |
| Leu | Lys | Tyr | Ala | Ala | Lys | Ile | Thr | Pro | Arg | Ser | Val | Leu | Thr | Thr | Gly | |
| 50 | | | | | 55 | | | | | 60 | | | | | | |
| att | gga | tct | act | agt | gca | ggt | ctg | acc | gtg | aca | gct | gtc | aaa | gac | tca | 240 |
| Ile | Gly | Ser | Thr | Ser | Ala | Gly | Leu | Thr | Val | Thr | Ala | Val | Lys | Asp | Ser | |
| 65 | | | | 70 | | | | | 75 | | | | | 80 | | |
| gga | gaa | tgg | aat | cta | gag | gct | ggg | gct | ttg | gtg | ctt | gca | gat | gct | ggt | 288 |
| Gly | Glu | Trp | Asn | Leu | Glu | Ala | Gly | Ala | Leu | Val | Leu | Ala | Asp | Ala | Gly | |
| | | | 85 | | | | | 90 | | | | | 95 | | | |
| ctc | tgc | tgt | att | gac | gaa | ttt | aac | agc | ctc | aaa | gaa | cat | gac | agg | aca | 336 |
| Leu | Cys | Cys | Ile | Asp | Glu | Phe | Asn | Ser | Leu | Lys | Glu | His | Asp | Arg | Thr | |
| | | | 100 | | | | | 105 | | | | | 110 | | | |
| agc | atc | cat | gaa | gca | atg | gag | caa | caa | | | | | | | | 363 |
| Ser | Ile | His | Glu | Ala | Met | Glu | Gln | Gln | | | | | | | | |
| | | 115 | | | | | 120 | | | | | | | | | |

<210> SEQ ID NO 28
<211> LENGTH: 121
<212> TYPE: PRT
<213> ORGANISM: Mus musculus

<400> SEQUENCE: 28

Val Phe Gly Met Tyr Leu Val Lys Leu Ala Val Ala Met Val Leu Ala
1               5                   10                  15

Gly Gly Ile Gln Arg Thr Asp Ala Ala Gly Thr Arg Val Arg Gly Glu
            20                  25                  30

Ser His Leu Leu Leu Val Gly Asp Pro Gly Thr Gly Lys Ser Gln Phe
        35                  40                  45

Leu Lys Tyr Ala Ala Lys Ile Thr Pro Arg Ser Val Leu Thr Thr Gly
    50                  55                  60

Ile Gly Ser Thr Ser Ala Gly Leu Thr Val Thr Ala Val Lys Asp Ser
65                  70                  75                  80

Gly Glu Trp Asn Leu Glu Ala Gly Ala Leu Val Leu Ala Asp Ala Gly
                85                  90                  95

Leu Cys Cys Ile Asp Glu Phe Asn Ser Leu Lys Glu His Asp Arg Thr
            100                 105                 110

Ser Ile His Glu Ala Met Glu Gln Gln
        115                 120

<210> SEQ ID NO 29
<211> LENGTH: 198
<212> TYPE: DNA

```
<213> ORGANISM: Mus musculus
<220> FEATURE:
<221> NAME/KEY: CDS
<222> LOCATION: (1)..(198)

<400> SEQUENCE: 29 ggg gat cct ggc aca ggg aaa tca caa ttc ctt aaa tat gca gca aag    48
Gly Asp Pro Gly Thr Gly Lys Ser Gln Phe Leu Lys Tyr Ala Ala Lys
1               5                   10                  15 att acc cca agg tcc gtt ttg acc aca gga att gga tct act agt gca   96
Ile Thr Pro Arg Ser Val Leu Thr Thr Gly Ile Gly Ser Thr Ser Ala
            20                  25                  30 ggt ctg acc gtg aca gct gtc aaa gac tca gga gaa tgg aat cta gag  144
Gly Leu Thr Val Thr Ala Val Lys Asp Ser Gly Glu Trp Asn Leu Glu
        35                  40                  45 gct ggg gct ttg gtg ctt gca gat gct ggt ctc tgc tgt att gac gaa  192
Ala Gly Ala Leu Val Leu Ala Asp Ala Gly Leu Cys Cys Ile Asp Glu
    50                  55                  60 ttt aac                                                          198
Phe Asn
65

<210> SEQ ID NO 30
<211> LENGTH: 66
<212> TYPE: PRT
<213> ORGANISM: Mus musculus

<400> SEQUENCE: 30

Gly Asp Pro Gly Thr Gly Lys Ser Gln Phe Leu Lys Tyr Ala Ala Lys
1               5                   10                  15

Ile Thr Pro Arg Ser Val Leu Thr Thr Gly Ile Gly Ser Thr Ser Ala
            20                  25                  30

Gly Leu Thr Val Thr Ala Val Lys Asp Ser Gly Glu Trp Asn Leu Glu
        35                  40                  45

Ala Gly Ala Leu Val Leu Ala Asp Ala Gly Leu Cys Cys Ile Asp Glu
    50                  55                  60

Phe Asn
65

<210> SEQ ID NO 31
<211> LENGTH: 453
<212> TYPE: DNA
<213> ORGANISM: Xenopus sp.
<220> FEATURE:
<221> NAME/KEY: CDS
<222> LOCATION: (1)..(453)

<400> SEQUENCE: 31 cct tta gaa ggt agg aat gaa att ctg gcc agc ctg tgt ccg cag gta   48
Pro Leu Glu Gly Arg Asn Glu Ile Leu Ala Ser Leu Cys Pro Gln Val
1               5                   10                  15 ttt ggt atg ttt gta gtg aag ctg gca gtg gcc atg gtg ctg gct ggt   96
Phe Gly Met Phe Val Val Lys Leu Ala Val Ala Met Val Leu Ala Gly
            20                  25                  30 gga gtt cag aga att gat tct gct gga aca aga gtg aga ggt gag tca  144
Gly Val Gln Arg Ile Asp Ser Ala Gly Thr Arg Val Arg Gly Glu Ser
        35                  40                  45 cat ctt ctg cta gtt gga gac cct ggc acg ggg aaa tca cag ttt ctg  192
His Leu Leu Leu Val Gly Asp Pro Gly Thr Gly Lys Ser Gln Phe Leu
    50                  55                  60 aag tat gct gca aaa att act ccg agg tct gtc ctt act gca ggc att  240
Lys Tyr Ala Ala Lys Ile Thr Pro Arg Ser Val Leu Thr Ala Gly Ile
65                  70                  75                  80
```

```
gga tct act agt gca ggc ttg act gtt act gca gtg aaa gac tct gga      288
Gly Ser Thr Ser Ala Gly Leu Thr Val Thr Ala Val Lys Asp Ser Gly
            85                  90                  95 gag tgg aat ctg gag gct gga gcc ttg gtg tta gct gat gga ggc ctg      336
Glu Trp Asn Leu Glu Ala Gly Ala Leu Val Leu Ala Asp Gly Gly Leu
        100                 105                 110 tgc tgc att gat gaa ttt aat agc atc aag gag cat gac aga acc agc      384
Cys Cys Ile Asp Glu Phe Asn Ser Ile Lys Glu His Asp Arg Thr Ser
    115                 120                 125 atc cat gag gca atg gag cag cag acc atc agt gtt gca aag gct ggg      432
Ile His Glu Ala Met Glu Gln Gln Thr Ile Ser Val Ala Lys Ala Gly
130                 135                 140 tta gtg tgc aag ctg aac act                                          453
Leu Val Cys Lys Leu Asn Thr
145                 150

<210> SEQ ID NO 32
<211> LENGTH: 151
<212> TYPE: PRT
<213> ORGANISM: Xenopus sp.

<400> SEQUENCE: 32

Pro Leu Glu Gly Arg Asn Glu Ile Leu Ala Ser Leu Cys Pro Gln Val
1               5                   10                  15

Phe Gly Met Phe Val Val Lys Leu Ala Val Ala Met Val Leu Ala Gly
            20                  25                  30

Gly Val Gln Arg Ile Asp Ser Ala Gly Thr Arg Val Arg Gly Glu Ser
        35                  40                  45

His Leu Leu Leu Val Gly Asp Pro Gly Thr Gly Lys Ser Gln Phe Leu
    50                  55                  60

Lys Tyr Ala Ala Lys Ile Thr Pro Arg Ser Val Leu Thr Ala Gly Ile
65                  70                  75                  80

Gly Ser Thr Ser Ala Gly Leu Thr Val Thr Ala Val Lys Asp Ser Gly
            85                  90                  95

Glu Trp Asn Leu Glu Ala Gly Ala Leu Val Leu Ala Asp Gly Gly Leu
        100                 105                 110

Cys Cys Ile Asp Glu Phe Asn Ser Ile Lys Glu His Asp Arg Thr Ser
    115                 120                 125

Ile His Glu Ala Met Glu Gln Gln Thr Ile Ser Val Ala Lys Ala Gly
130                 135                 140

Leu Val Cys Lys Leu Asn Thr
145                 150

<210> SEQ ID NO 33
<211> LENGTH: 363
<212> TYPE: DNA
<213> ORGANISM: Xenopus sp.
<220> FEATURE:
<221> NAME/KEY: CDS
<222> LOCATION: (1)..(363)

<400> SEQUENCE: 33 agc ctg tgt ccg cag gta ttt ggt atg ttt gta gtg aag ctg gca gtg       48
Ser Leu Cys Pro Gln Val Phe Gly Met Phe Val Val Lys Leu Ala Val
1               5                   10                  15 gcc atg gtg ctg gct ggt gga gtt cag aga att gat tct gct gga aca       96
Ala Met Val Leu Ala Gly Gly Val Gln Arg Ile Asp Ser Ala Gly Thr
            20                  25                  30 aga gtg aga ggt gag tca cat ctt ctg cta gtt gga gac cct ggc acg      144
Arg Val Arg Gly Glu Ser His Leu Leu Leu Val Gly Asp Pro Gly Thr
```

```
                35                  40                  45
ggg aaa tca cag ttt ctg aag tat gct gca aaa att act ccg agg tct        192
Gly Lys Ser Gln Phe Leu Lys Tyr Ala Ala Lys Ile Thr Pro Arg Ser
 50                  55                  60 gtc ctt act gca ggc att gga tct act agt gca ggc ttg act gtt act        240
Val Leu Thr Ala Gly Ile Gly Ser Thr Ser Ala Gly Leu Thr Val Thr
 65                  70                  75                  80 gca gtg aaa gac tct gga gag tgg aat ctg gag gct gga gcc ttg gtg        288
Ala Val Lys Asp Ser Gly Glu Trp Asn Leu Glu Ala Gly Ala Leu Val
                 85                  90                  95 tta gct gat gga ggc ctg tgc tgc att gat gaa ttt aat agc atc aag        336
Leu Ala Asp Gly Gly Leu Cys Cys Ile Asp Glu Phe Asn Ser Ile Lys
            100                 105                 110 gag cat gac aga acc agc atc cat gag                                     363
Glu His Asp Arg Thr Ser Ile His Glu
        115                 120
```

<210> SEQ ID NO 34
<211> LENGTH: 121
<212> TYPE: PRT
<213> ORGANISM: Xenopus sp.

<400> SEQUENCE: 34

```
Ser Leu Cys Pro Gln Val Phe Gly Met Phe Val Val Lys Leu Ala Val
 1               5                  10                  15

Ala Met Val Leu Ala Gly Gly Val Gln Arg Ile Asp Ser Ala Gly Thr
                20                  25                  30

Arg Val Arg Gly Glu Ser His Leu Leu Val Gly Asp Pro Gly Thr
            35                  40                  45

Gly Lys Ser Gln Phe Leu Lys Tyr Ala Ala Lys Ile Thr Pro Arg Ser
 50                  55                  60

Val Leu Thr Ala Gly Ile Gly Ser Thr Ser Ala Gly Leu Thr Val Thr
 65                  70                  75                  80

Ala Val Lys Asp Ser Gly Glu Trp Asn Leu Glu Ala Gly Ala Leu Val
                 85                  90                  95

Leu Ala Asp Gly Gly Leu Cys Cys Ile Asp Glu Phe Asn Ser Ile Lys
            100                 105                 110

Glu His Asp Arg Thr Ser Ile His Glu
        115                 120
```

<210> SEQ ID NO 35
<211> LENGTH: 198
<212> TYPE: DNA
<213> ORGANISM: Xenopus sp.
<220> FEATURE:
<221> NAME/KEY: CDS
<222> LOCATION: (1)..(198)

<400> SEQUENCE: 35

```
gga gac cct ggc acg ggg aaa tca cag ttt ctg aag tat gct gca aaa         48
Gly Asp Pro Gly Thr Gly Lys Ser Gln Phe Leu Lys Tyr Ala Ala Lys
 1               5                  10                  15 att act ccg agg tct gtc ctt act gca ggc att gga tct act agt gca         96
Ile Thr Pro Arg Ser Val Leu Thr Ala Gly Ile Gly Ser Thr Ser Ala
                20                  25                  30 ggc ttg act gtt act gca gtg aaa gac tct gga gag tgg aat ctg gag        144
Gly Leu Thr Val Thr Ala Val Lys Asp Ser Gly Glu Trp Asn Leu Glu
            35                  40                  45 gct gga gcc ttg gtg tta gct gat gga ggc ctg tgc tgc att gat gaa        192
Ala Gly Ala Leu Val Leu Ala Asp Gly Gly Leu Cys Cys Ile Asp Glu
 50                  55                  60
```

```
ttt aat                                                                         198
Phe Asn
 65

<210> SEQ ID NO 36
<211> LENGTH: 66
<212> TYPE: PRT
<213> ORGANISM: Xenopus sp.

<400> SEQUENCE: 36

Gly Asp Pro Gly Thr Gly Lys Ser Gln Phe Leu Lys Tyr Ala Ala Lys
 1               5                  10                  15

Ile Thr Pro Arg Ser Val Leu Thr Ala Gly Ile Gly Ser Thr Ser Ala
            20                  25                  30

Gly Leu Thr Val Thr Ala Val Lys Asp Ser Gly Glu Trp Asn Leu Glu
        35                  40                  45

Ala Gly Ala Leu Val Leu Ala Asp Gly Gly Leu Cys Cys Ile Asp Glu
    50                  55                  60

Phe Asn
 65

<210> SEQ ID NO 37
<211> LENGTH: 24
<212> TYPE: DNA
<213> ORGANISM: Homo sapiens
<220> FEATURE:
<221> NAME/KEY: CDS
<222> LOCATION: (1)..(24)

<400> SEQUENCE: 37 ggg gat cct ggc aca ggg aaa tct                                                  24
Gly Asp Pro Gly Thr Gly Lys Ser
 1               5

<210> SEQ ID NO 38
<211> LENGTH: 8
<212> TYPE: PRT
<213> ORGANISM: Homo sapiens

<400> SEQUENCE: 38

Gly Asp Pro Gly Thr Gly Lys Ser
 1               5

<210> SEQ ID NO 39
<211> LENGTH: 12
<212> TYPE: DNA
<213> ORGANISM: Homo sapiens
<220> FEATURE:
<221> NAME/KEY: CDS
<222> LOCATION: (1)..(12)

<400> SEQUENCE: 39 gat gag ttc aat                                                                  12
Asp Glu Phe Asn
 1

<210> SEQ ID NO 40
<211> LENGTH: 4
<212> TYPE: PRT
<213> ORGANISM: Homo sapiens

<400> SEQUENCE: 40

Asp Glu Phe Asn
 1
```

```
<210> SEQ ID NO 41
<211> LENGTH: 24
<212> TYPE: DNA
<213> ORGANISM: Mus musculus
<220> FEATURE:
<221> NAME/KEY: CDS
<222> LOCATION: (1)..(24)

<400> SEQUENCE: 41 ggg gat cct ggc aca ggg aaa tca                             24
Gly Asp Pro Gly Thr Gly Lys Ser
1               5

<210> SEQ ID NO 42
<211> LENGTH: 8
<212> TYPE: PRT
<213> ORGANISM: Mus musculus

<400> SEQUENCE: 42

Gly Asp Pro Gly Thr Gly Lys Ser
1               5

<210> SEQ ID NO 43
<211> LENGTH: 12
<212> TYPE: DNA
<213> ORGANISM: Mus musculus
<220> FEATURE:
<221> NAME/KEY: CDS
<222> LOCATION: (1)..(12)

<400> SEQUENCE: 43 gac gaa ttt aac                                             12
Asp Glu Phe Asn
1

<210> SEQ ID NO 44
<211> LENGTH: 4
<212> TYPE: PRT
<213> ORGANISM: Mus musculus

<400> SEQUENCE: 44

Asp Glu Phe Asn
1

<210> SEQ ID NO 45
<211> LENGTH: 24
<212> TYPE: DNA
<213> ORGANISM: Xenopus sp.
<220> FEATURE:
<221> NAME/KEY: CDS
<222> LOCATION: (1)..(24)

<400> SEQUENCE: 45 gga gac cct ggc acg ggg aaa tca                             24
Gly Asp Pro Gly Thr Gly Lys Ser
1               5

<210> SEQ ID NO 46
<211> LENGTH: 8
<212> TYPE: PRT
<213> ORGANISM: Xenopus sp.

<400> SEQUENCE: 46

Gly Asp Pro Gly Thr Gly Lys Ser
1               5

<210> SEQ ID NO 47
```

```
<211> LENGTH: 12
<212> TYPE: DNA
<213> ORGANISM: Xenopus sp.
<220> FEATURE:
<221> NAME/KEY: CDS
<222> LOCATION: (1)..(12)

<400> SEQUENCE: 47 gat gaa ttt aat                                                     12
Asp Glu Phe Asn
1

<210> SEQ ID NO 48
<211> LENGTH: 4
<212> TYPE: PRT
<213> ORGANISM: Xenopus sp.

<400> SEQUENCE: 48

Asp Glu Phe Asn
1

<210> SEQ ID NO 49
<211> LENGTH: 624
<212> TYPE: PRT
<213> ORGANISM: Homo sapiens

<400> SEQUENCE: 49

Met Asn Ser Asp Gln Val Thr Leu Val Gly Gln Val Phe Glu Ser Tyr
1               5                   10                  15

Val Ser Glu Tyr His Lys Asn Asp Ile Leu Ile Leu Lys Glu Arg
                20                  25                  30

Asp Glu Asp Ala His Tyr Pro Val Val Asn Ala Met Thr Leu Phe
            35                  40                  45

Glu Thr Asn Met Glu Ile Gly Glu Tyr Phe Asn Met Phe Pro Ser Glu
    50                  55                  60

Val Leu Thr Ile Phe Asp Ser Ala Leu Arg Arg Ser Ala Leu Thr Ile
65                  70                  75                  80

Leu Gln Ser Leu Ser Gln Pro Glu Ala Val Ser Met Lys Gln Asn Leu
                85                  90                  95

His Ala Arg Ile Ser Gly Leu Pro Val Cys Pro Glu Leu Val Arg Glu
                100                 105                 110

His Ile Pro Lys Thr Lys Asp Val Gly His Phe Leu Ser Val Thr Gly
            115                 120                 125

Thr Val Ile Arg Thr Ser Leu Val Lys Val Leu Glu Phe Glu Arg Asp
    130                 135                 140

Tyr Met Cys Asn Lys Cys Lys His Val Phe Val Ile Lys Ala Asp Phe
145                 150                 155                 160

Glu Gln Tyr Tyr Thr Phe Cys Arg Pro Ser Ser Cys Pro Ser Leu Glu
                165                 170                 175

Ser Cys Asp Ser Ser Lys Phe Thr Cys Leu Ser Gly Leu Ser Ser Ser
                180                 185                 190

Pro Thr Arg Cys Arg Asp Tyr Gln Glu Ile Lys Ile Gln Glu Gln Val
            195                 200                 205

Gln Arg Leu Ser Val Gly Ser Ile Pro Arg Ser Met Lys Val Ile Leu
    210                 215                 220

Glu Asp Asp Leu Val Asp Ser Cys Lys Ser Gly Asp Asp Leu Thr Ile
225                 230                 235                 240

Tyr Gly Ile Val Met Gln Arg Trp Lys Pro Phe Gln Gln Asp Val Arg
                245                 250                 255
```

Cys Glu Val Glu Ile Val Leu Lys Ala Asn Tyr Ile Gln Val Asn Asn
              260                 265                 270

Glu Gln Ser Ser Gly Ile Ile Met Asp Glu Val Gln Lys Glu Phe
              275                 280                 285

Glu Asp Phe Trp Glu Tyr Tyr Lys Ser Asp Pro Phe Ala Gly Arg Asn
290                 295                 300

Val Ile Leu Ala Ser Leu Cys Pro Gln Val Phe Gly Met Tyr Leu Val
305                 310                 315                 320

Lys Leu Ala Val Ala Met Val Leu Ala Gly Gly Ile Gln Arg Thr Asp
                    325                 330                 335

Ala Thr Gly Thr Arg Val Arg Gly Glu Ser His Leu Leu Leu Val Gly
              340                 345                 350

Asp Pro Gly Thr Gly Lys Ser Gln Phe Leu Lys Tyr Ala Ala Lys Ile
              355                 360                 365

Thr Pro Arg Ser Val Leu Thr Thr Gly Ile Gly Ser Thr Ser Ala Gly
              370                 375                 380

Leu Thr Val Thr Ala Val Lys Asp Ser Gly Glu Trp Asn Leu Glu Ala
385                 390                 395                 400

Gly Ala Leu Val Leu Ala Asp Ala Gly Leu Cys Cys Ile Asp Glu Phe
                    405                 410                 415

Asn Ser Leu Lys Glu His Asp Arg Thr Ser Ile His Glu Ala Met Glu
              420                 425                 430

Gln Gln Thr Ile Ser Val Ala Lys Ala Gly Leu Val Cys Lys Leu Asn
              435                 440                 445

Thr Arg Thr Thr Ile Leu Ala Ala Thr Asn Pro Lys Gly Gln Tyr Asp
              450                 455                 460

Pro Gln Glu Ser Val Ser Val Asn Ile Ala Leu Gly Ser Pro Leu Leu
465                 470                 475                 480

Ser Arg Phe Asp Leu Ile Leu Val Leu Leu Asp Thr Lys Asn Glu Asp
                    485                 490                 495

Trp Asp Arg Ile Ile Ser Ser Phe Ile Leu Glu Asn Lys Gly Tyr Pro
              500                 505                 510

Ser Lys Ser Glu Lys Leu Trp Ser Met Glu Lys Met Lys Thr Tyr Phe
              515                 520                 525

Cys Leu Ile Arg Asn Leu Gln Pro Thr Leu Ser Asp Val Gly Asn Gln
              530                 535                 540

Val Leu Leu Arg Tyr Tyr Gln Met Gln Arg Gln Ser Asp Cys Arg Asn
545                 550                 555                 560

Ala Ala Arg Thr Thr Ile Arg Leu Leu Glu Ser Leu Ile Arg Leu Ala
                    565                 570                 575

Glu Ala His Ala Arg Leu Met Phe Arg Asp Thr Val Thr Leu Glu Asp
              580                 585                 590

Ala Ile Thr Val Val Ser Val Met Glu Ser Ser Met Gln Gly Gly Ala
              595                 600                 605

Leu Leu Gly Gly Val Asn Ala Leu His Thr Ser Phe Pro Glu Asn Pro
              610                 615                 620

<210> SEQ ID NO 50
<211> LENGTH: 780
<212> TYPE: PRT
<213> ORGANISM: Mus musculus

<400> SEQUENCE: 50

Met Asp Gln Arg Thr Thr Arg Asn Gly Lys Tyr Cys Asp Val Glu Pro
1               5                   10                  15

-continued

```
Val Ser Arg Ser Asn Pro Ala Pro Cys Leu Arg Asp Pro Leu Arg
         20                  25                  30

Arg Leu Val Arg Pro Lys Pro Arg Leu Gln Leu Pro Glu Ser Arg Leu
             35                  40                  45

Ser Pro Cys Ser Arg Leu Pro Leu Ala Asp Ser Ser Val Arg Pro Gly
 50                  55                  60

Ala Arg Pro Pro Ala Ser Ala Pro Gly Arg Ser Pro Ser Gly Arg Lys
 65                  70                  75                  80

Val Glu Ala Val Arg Gly Ser Gly Ser Ala Gly Ser Ser Ser Pro Ser
                 85                  90                  95

Glu Ala Glu Arg Glu Gln Arg Gly Glu Ala Cys Ala Pro Pro Arg Lys
             100                 105                 110

Ala Ala Pro Ser Ser Gly Arg Ala His Ala Pro Pro Pro Thr Pro
             115                 120                 125

Arg Gly Ser Gly Trp Gly Asp His Gly Arg Ser Ala Val Pro Ala Thr
 130                 135                 140

Lys Thr Val Arg Val Glu Pro Tyr Pro Pro Phe Lys Met Asn Ser Glu
145                 150                 155                 160

Gln Val Thr Leu Val Gly Gln Val Phe Glu Ser Tyr Val Ser Glu Tyr
             165                 170                 175

His Lys Asn Asp Ile Leu Leu Ile Leu Lys Glu Arg Asp Glu Asp Ala
             180                 185                 190

His Tyr Pro Val Val Asn Ala Met Ser Leu Phe Glu Thr Asn Met
             195                 200                 205

Glu Ile Gly Asp Tyr Phe Thr Val Phe Pro Asn Glu Val Leu Thr Val
 210                 215                 220

Phe Asp Ser Ala Leu Arg Arg Ser Ala Leu Ala Ile Leu Gln Ser Leu
225                 230                 235                 240

Pro Glu Thr Glu Gly Leu Ser Met Lys Gln Asn Leu His Ala Arg Ile
             245                 250                 255

Ser Gly Leu Pro Val Cys Pro Glu Leu Val Arg Glu His Ile Pro Lys
             260                 265                 270

Thr Lys Asp Val Gly His Phe Leu Ser Val Thr Gly Thr Val Ile Arg
             275                 280                 285

Thr Ser Leu Val Lys Val Leu Glu Phe Glu Arg Asp Tyr Met Cys Asn
 290                 295                 300

Lys Cys Lys His Val Phe Met Val Glu Ala Asp Phe Glu Gln Tyr Tyr
305                 310                 315                 320

Thr Phe Ser Arg Pro Ser Ser Cys Pro Ser Leu Ala Ser Cys Asp Ser
             325                 330                 335

Ser Lys Phe Ser Cys Leu Ser Asp Leu Ser Ser Pro Ala Arg Cys
             340                 345                 350

Arg Asp Tyr Gln Glu Ile Lys Ile Gln Glu Gln Val Gln Arg Leu Ser
             355                 360                 365

Val Gly Ser Ile Pro Arg Ser Met Lys Val Ile Leu Glu Asp Asp Leu
 370                 375                 380

Val Asp Ser Cys Lys Ser Gly Asp Asp Leu Thr Ile Tyr Gly Val Val
385                 390                 395                 400

Met Gln Arg Trp Lys Pro Phe Gln Arg Asp Val Arg Cys Glu Val Glu
             405                 410                 415

Ile Val Leu Lys Ala Asn Tyr Val Gln Val Asn Asn Glu Gln Ser Ser
             420                 425                 430

Gly Met Val Met Asp Glu Asp Thr Arg Lys Glu Phe Glu Asp Phe Trp
 435                 440                 445
```

Glu His Tyr Lys Ser Asp Pro Phe Ala Gly Arg Asn Glu Ile Leu Ala
    450                 455                 460

Ser Leu Cys Pro Gln Val Phe Gly Met Tyr Leu Val Lys Leu Ala Val
465                 470                 475                 480

Ala Met Val Leu Ala Gly Gly Ile Gln Arg Thr Asp Ala Ala Gly Thr
                485                 490                 495

Arg Val Arg Gly Glu Ser His Leu Leu Leu Val Gly Asp Pro Gly Thr
            500                 505                 510

Gly Lys Ser Gln Phe Leu Lys Tyr Ala Ala Lys Ile Thr Pro Arg Ser
        515                 520                 525

Val Leu Thr Thr Gly Ile Gly Ser Thr Ser Ala Gly Leu Thr Val Thr
    530                 535                 540

Ala Val Lys Asp Ser Gly Glu Trp Asn Leu Glu Ala Gly Ala Leu Val
545                 550                 555                 560

Leu Ala Asp Ala Gly Leu Cys Cys Ile Asp Glu Phe Asn Ser Leu Lys
                565                 570                 575

Glu His Asp Arg Thr Ser Ile His Glu Ala Met Glu Gln Gln Thr Ile
            580                 585                 590

Ser Val Ala Lys Ala Gly Leu Val Cys Lys Leu Asn Thr Arg Thr Thr
        595                 600                 605

Ile Leu Ala Ala Thr Asn Pro Lys Gly Gln Tyr Asp Pro Lys Glu Ser
    610                 615                 620

Val Ser Val Asn Ile Ala Leu Gly Ser Pro Leu Leu Ser Arg Phe Asp
625                 630                 635                 640

Leu Val Leu Val Leu Leu Asp Thr Arg Asn Glu Asp Trp Asp Arg Ile
                645                 650                 655

Ile Ser Ser Phe Ile Leu Glu Asn Lys Gly Tyr Pro Ser Lys Ser Glu
            660                 665                 670

Asn Leu Trp Ser Met Glu Lys Met Lys Thr Tyr Phe Cys Leu Ile Arg
        675                 680                 685

Asn Leu His Pro Thr Leu Ser Glu Val Ser Asn Gln Val Leu Leu Arg
    690                 695                 700

Tyr Tyr Gln Met Gln Arg Gln Ser Asp Ser Arg Asn Ala Ala Arg Thr
705                 710                 715                 720

Thr Ile Arg Leu Leu Glu Ser Leu Ile Arg Leu Ala Glu Ala His Ala
                725                 730                 735

Arg Leu Met Phe Arg Ser Ala Val Thr Leu Glu Asp Ala Val Thr Ala
            740                 745                 750

Val Ser Val Met Glu Ser Ser Met Gln Gly Gly Ala Leu Leu Gly Gly
        755                 760                 765

Val Asn Ala Leu His Thr Ser Phe Pro Glu Asn Pro
    770                 775                 780

<210> SEQ ID NO 51
<211> LENGTH: 626
<212> TYPE: PRT
<213> ORGANISM: Gallus gallus

<400> SEQUENCE: 51

Met Ala Leu Arg Ala Asp Gln Val Ser Leu Ile Gly Gln Val Phe Glu
1               5                   10                  15

Ser Tyr Leu Leu Gln His His Arg Asp Asp Ile Leu Gly Ile Leu Arg
            20                  25                  30

Gln Gly Asp Asp Glu Ala His Tyr Pro Val Leu Val Asp Ala Leu Thr
        35                  40                  45

-continued

```
Leu Phe Glu Thr Asn Met Glu Ile Gly Glu Tyr Phe Asn Ala Phe Pro
     50                  55                  60

Ser Gln Val Leu Pro Ile Phe Asp Gly Ala Leu Arg Arg Ala Ala Met
 65                  70                  75                  80

Ala Val Leu Gln Ala Ala Thr Pro Ser Pro Glu Leu Arg Met Lys Pro
                 85                  90                  95

Asn Leu His Ala Arg Ile Ser Gly Leu Pro Ile Cys Pro Glu Leu Thr
                100                 105                 110

Arg Glu His Ile Pro Lys Thr Arg Asp Val Gly His Phe Leu Ser Val
            115                 120                 125

Thr Gly Thr Val Ile Arg Thr Ser Leu Val Lys Val Leu Glu Phe Glu
        130                 135                 140

Arg Ser Tyr Ile Cys Asn Lys Cys Lys His Val Phe Val Ala Lys Ala
145                 150                 155                 160

Asp Phe Glu Gln Tyr Tyr Ala Phe Cys Arg Pro Ser Ala Cys Leu Asn
                165                 170                 175

Glu Glu Gly Cys Asn Ser Thr Lys Phe Thr Cys Leu Ser Gly Thr Ser
            180                 185                 190

Ser Ser Pro Ser Ser Cys Arg Asp Tyr Gln Glu Ile Lys Ile Gln Glu
        195                 200                 205

Gln Val Gln Arg Leu Ser Val Gly Ser Ile Pro Arg Cys Met Val Val
210                 215                 220

Val Leu Glu Asp Asp Leu Val Asp Ser Cys Lys Ser Gly Asp Asp Ile
225                 230                 235                 240

Thr Val Tyr Gly Val Val Met Gln Arg Trp Lys Pro Phe His Gln Asp
                245                 250                 255

Ala Arg Cys Asp Leu Glu Leu Val Leu Lys Ala Asn Tyr Val Lys Val
            260                 265                 270

Asn Asn Glu Gln Leu Ala Gly Val Thr Ile Asp Glu Glu Val Arg Lys
        275                 280                 285

Glu Phe Glu Asp Phe Trp Glu Lys His Arg Asn Asn Pro Leu Ala Gly
290                 295                 300

Arg Asn Glu Ile Leu Ala Ser Leu Cys Pro Gln Val Phe Gly Leu Tyr
305                 310                 315                 320

Leu Val Lys Leu Ala Val Ala Met Val Leu Ala Gly Gly Val Gln Arg
                325                 330                 335

Ile Asp Ala Thr Gly Thr Arg Ile Arg Gly Glu Ser His Leu Leu Leu
            340                 345                 350

Val Gly Asp Pro Gly Thr Gly Lys Ser Gln Phe Leu Lys Tyr Ala Val
        355                 360                 365

Lys Ile Thr Pro Arg Ser Val Leu Thr Ala Gly Ile Gly Ser Thr Ser
370                 375                 380

Ala Gly Leu Thr Val Thr Ala Val Lys Asp Phe Gly Glu Trp Asn Leu
385                 390                 395                 400

Glu Ala Gly Ala Leu Val Leu Ala Asp Gly Gly Leu Cys Cys Ile Asp
                405                 410                 415

Glu Phe Asn Ser Ile Lys Glu His Asp Arg Thr Ser Ile His Glu Ala
            420                 425                 430

Met Glu Gln Gln Thr Ile Ser Val Ala Lys Ala Gly Leu Val Cys Lys
        435                 440                 445

Leu Asn Thr Arg Thr Thr Ile Leu Ala Ala Thr Asn Pro Lys Gly His
450                 455                 460

Tyr Asp Pro Ala Glu Ser Val Ser Val Asn Ile Ala Leu Gly Ser Pro
```

```
                   465                 470                 475                 480
Leu Leu Ser Arg Phe Asp Leu Val Leu Leu Asp Thr Lys Asn
                485                 490                 495

Glu Glu Trp Asp Arg Ile Ile Ser Ser Phe Ile Leu Gln Asn Lys Gly
            500                 505                 510

Cys Pro Ser Lys Ser Glu Lys Leu Trp Ser Met Glu Lys Met Lys Thr
            515                 520                 525

Tyr Phe Cys Leu Ile Lys Arg Ile Gln Pro Lys Leu Ser Asp Glu Ser
            530                 535                 540

Asn Leu Ile Leu Val Arg Tyr Tyr Gln Met Gln Arg Gln Ser Asp Cys
545                 550                 555                 560

Arg Asn Ala Ala Arg Thr Thr Ile Arg Leu Leu Glu Ser Leu Ile Arg
                565                 570                 575

Leu Ala Glu Ala His Ala Arg Leu Met Phe Arg Asp Thr Val Thr Leu
                580                 585                 590

Glu Asp Ala Val Thr Val Val Ser Val Met Glu Ser Ser Met Gln Gly
            595                 600                 605

Gly Ala Leu Leu Gly Ala Ile Asn Ala Leu His Thr Ser Phe Pro Glu
    610                 615                 620

Asn Pro
625

<210> SEQ ID NO 52
<211> LENGTH: 625
<212> TYPE: PRT
<213> ORGANISM: Xenopus sp.

<400> SEQUENCE: 52

Met Tyr Leu Gly Phe Glu Gln Val Ala Leu Val Gly Gln Val Phe Glu
1               5                   10                  15

Ser Phe Val Leu Glu His His Lys Asn Glu Ile Ala Gln Ile Leu Thr
                20                  25                  30

Glu Lys Glu Glu His Ala His Tyr Ser Leu Val Val Asn Ala Met Thr
            35                  40                  45

Leu Phe Glu Ala Asn Met Glu Ile Gly Glu Tyr Phe Asn Ala Phe Pro
50                  55                  60

Asn Glu Val Leu Pro Val Phe Asp Asn Ala Leu Arg Cys Ala Ala Met
65                  70                  75                  80

Ser Phe Leu Gln Ser Cys Ser Glu Lys Tyr Thr Phe Leu Met Lys Gln
                85                  90                  95

Asn Leu His Ala Arg Ile Thr Gly Leu Pro Val Cys Pro Glu Leu Thr
            100                 105                 110

Arg Glu His Ile Pro Arg Thr Arg Asp Val Gly His Phe Leu Ser Val
        115                 120                 125

Thr Gly Thr Val Ile Arg Thr Ser Leu Val Lys Val Leu Glu Tyr Glu
    130                 135                 140

Gln Asp Phe Met Cys Asn Lys Cys Lys His Val Val Thr Val Lys Ala
145                 150                 155                 160

Asp Phe Glu Gln His Tyr Thr Phe Lys Pro Pro Ile Ala Cys Ser Asn
                165                 170                 175

Glu Glu Gly Cys Asn Ser Thr Lys Phe Thr Cys Leu Ser Asp Ser Ser
            180                 185                 190

Ser Pro Ala Ser Cys Arg Asp Tyr Gln Glu Ile Lys Ile Gln Glu Gln
        195                 200                 205

Val Gln Arg Leu Ser Val Gly Ser Ile Pro Arg Ser Met Ile Val Val
```

-continued

```
            210                 215                 220
Leu Glu Asp Asp Leu Val Asp Ser Cys Lys Ser Gly Asp Asp Ile Thr
225                 230                 235                 240

Val Tyr Gly Val Val Met Gln Arg Trp Lys Pro Leu Tyr Ile Asp Met
                245                 250                 255

Arg Cys Asp Leu Glu Ile Val Leu Lys Ala Asn Tyr Ile Ser Val Asn
                260                 265                 270

Asn Glu Gln Pro Cys Gly Val Val Ile Asn Glu Val Arg Lys Glu
                275                 280                 285

Tyr Glu Asp Phe Trp Val Lys Tyr Arg Asn Asn Pro Leu Glu Gly Arg
                290                 295                 300

Asn Glu Ile Leu Ala Ser Leu Cys Pro Gln Val Phe Gly Met Phe Val
305                 310                 315                 320

Val Lys Leu Ala Val Ala Met Val Leu Ala Gly Gly Val Gln Arg Ile
                325                 330                 335

Asp Ser Ala Gly Thr Arg Val Arg Gly Glu Ser His Leu Leu Leu Val
                340                 345                 350

Gly Asp Pro Gly Thr Gly Lys Ser Gln Phe Leu Lys Tyr Ala Ala Lys
                355                 360                 365

Ile Thr Pro Arg Ser Val Leu Thr Ala Gly Ile Gly Ser Thr Ser Ala
                370                 375                 380

Gly Leu Thr Val Thr Ala Val Lys Asp Ser Gly Glu Trp Asn Leu Glu
385                 390                 395                 400

Ala Gly Ala Leu Val Leu Ala Asp Gly Gly Leu Cys Cys Ile Asp Glu
                405                 410                 415

Phe Asn Ser Ile Lys Glu His Asp Arg Thr Ser Ile His Glu Ala Met
                420                 425                 430

Glu Gln Gln Thr Ile Ser Val Ala Lys Ala Gly Leu Val Cys Lys Leu
                435                 440                 445

Asn Thr Arg Thr Thr Ile Leu Ala Ala Thr Asn Pro Lys Gly Gln Tyr
                450                 455                 460

Asp Pro Asp Glu Ser Ile Ser Val Asn Val Ala Leu Ala Ser Pro Leu
465                 470                 475                 480

Leu Ser Arg Phe Asp Leu Val Leu Val Leu Leu Asp Thr Lys Asn Glu
                485                 490                 495

Asp Trp Asp Arg Ile Ile Ser Ser Phe Ile Leu Glu Ser Lys Gly Cys
                500                 505                 510

Pro Arg Lys Ser Asp Lys Leu Trp Ser Met Glu Lys Met Lys Thr Tyr
                515                 520                 525

Phe Cys Leu Ile Lys Asn Leu Gln Pro Lys Met Ser Gln Asp Ala Asn
                530                 535                 540

Val Ile Leu Val Arg Tyr Tyr Gln Leu Gln Arg Gln Ser Ser Cys Arg
545                 550                 555                 560

Asn Ala Ala Arg Thr Thr Ile Arg Leu Leu Glu Ser Leu Ile Arg Leu
                565                 570                 575

Ala Glu Ala His Ala Arg Ile Met Tyr Arg Asp Val Val Thr Thr Glu
                580                 585                 590

Asp Ala Ile Thr Val Val Ser Ile Met Glu Ser Ser Met Gln Gly Gly
                595                 600                 605

Ala Leu Leu Gly Gly Val Asn Ala Leu His Thr Ser Phe Pro Glu Asn
                610                 615                 620

Pro
625
```

<210> SEQ ID NO 53
<211> LENGTH: 236
<212> TYPE: PRT
<213> ORGANISM: Xenopus sp.

<400> SEQUENCE: 53

Lys Lys Phe Cys Lys Ala His Ser Lys Asp Ile Phe Glu His Leu Ser
1               5                   10                  15

Lys Ser Leu Ala Pro Ser Ile His Gly His Glu Tyr Ile Lys Lys Ala
                20                  25                  30

Ile Leu Cys Met Leu Leu Gly Gly Asn Glu Lys Val Leu Glu Asn Gly
            35                  40                  45

Thr Arg Ile Arg Gly Asp Ile Asn Val Leu Leu Ile Gly Asp Pro Ser
    50                  55                  60

Val Ala Lys Ser Gln Leu Leu Arg Tyr Val Leu His Thr Ala Pro Arg
65                  70                  75                  80

Ala Ile Pro Thr Thr Gly Arg Gly Ser Ser Gly Val Gly Leu Thr Ala
                85                  90                  95

Ala Val Thr Thr Asp Gln Glu Thr Gly Glu Arg Arg Leu Glu Ala Gly
            100                 105                 110

Ala Met Val Leu Ala Asp Arg Gly Val Val Cys Ile Asp Glu Phe Asp
        115                 120                 125

Lys Met Ser Asp Met Asp Arg Thr Ala Ile His Glu Val Met Glu Gln
130                 135                 140

Gly Arg Val Thr Ile Ala Lys Ala Gly Ile Gln Ala Arg Leu Asn Ala
145                 150                 155                 160

Arg Cys Ser Val Leu Ala Ala Ala Asn Pro Val Tyr Gly Arg Tyr Asp
                165                 170                 175

Gln Tyr Arg Thr Pro Met Glu Asn Ile Gly Leu Gln Asp Ser Leu Leu
            180                 185                 190

Ser Arg Phe Asp Leu Leu Phe Ile Val Leu Asp Lys Met Asp Ala Asp
        195                 200                 205

Asn Asp Gln Glu Ile Ala Asp His Val Leu Arg Met His Arg Tyr Arg
    210                 215                 220

Thr Pro Gly Glu Gln Asp Gly Tyr Ala Leu Pro Leu
225                 230                 235

<210> SEQ ID NO 54
<211> LENGTH: 224
<212> TYPE: PRT
<213> ORGANISM: Xenopus sp.

<400> SEQUENCE: 54

Glu Glu Leu Arg Gln Ile Thr Glu Asp Phe Tyr Glu Lys Leu Ala
1               5                   10                  15

Ala Ser Ile Ala Pro Glu Ile Tyr Gly His Glu Asp Val Lys Lys Ala
                20                  25                  30

Leu Leu Leu Leu Leu Val Gly Gly Val Asp Asn Ser Pro Arg Gly Met
            35                  40                  45

Lys Ile Arg Gly Asn Ile Asn Ile Cys Leu Met Gly Asp Pro Gly Val
    50                  55                  60

Ala Lys Ser Gln Leu Leu Ser Tyr Ile Asp Arg Leu Ala Pro Arg Ser
65                  70                  75                  80

Gln Tyr Thr Thr Gly Arg Gly Ser Ser Gly Val Gly Leu Thr Ala Ala
                85                  90                  95

Val Met Lys Asp Pro Val Thr Gly Glu Met Thr Leu Glu Gly Gly Ala

```
                      100                 105                 110
Leu Val Leu Ala Asp Gln Gly Val Cys Cys Ile Asp Glu Phe Asp Lys
            115                 120                 125

Met Met Asp Thr Asp Arg Thr Ala Ile His Glu Val Met Glu Gln Gln
        130                 135                 140

Thr Ile Ser Ile Ala Lys Ala Gly Ile Met Thr Thr Leu Asn Ala Arg
145                 150                 155                 160

Cys Ser Ile Leu Ala Ala Ala Asn Pro Ala Tyr Gly Arg Tyr Asn Pro
                165                 170                 175

Lys Lys Thr Val Glu Gln Asn Ile Gln Leu Pro Ala Ala Leu Leu Ser
            180                 185                 190

Arg Phe Asp Val Leu Trp Leu Ile Gln Asp Lys Pro Asp Arg Asp Asn
            195                 200                 205

Asp Leu Arg Leu Ala Gln His Ile Thr Tyr Val His Gln His Ser Lys
        210                 215                 220
```

<210> SEQ ID NO 55
<211> LENGTH: 226
<212> TYPE: PRT
<213> ORGANISM: Xenopus sp.

<400> SEQUENCE: 55

```
Glu Glu Glu Phe Arg Arg Leu Ala Ala Lys Pro Asp Ile Tyr Glu Thr
1               5                   10                  15

Val Ala Lys Ser Ile Ala Pro Ser Ile Tyr Gly Ser Ser Asp Ile Lys
            20                  25                  30

Lys Ala Ile Ala Cys Leu Leu Phe Gly Gly Ser Arg Lys Arg Leu Pro
        35                  40                  45

Asp Gly Leu Thr Arg Arg Gly Asp Val Asn Leu Leu Met Leu Gly Asp
    50                  55                  60

Pro Gly Thr Ala Lys Ser Gln Leu Leu Lys Phe Val Glu Arg Cys Ser
65                  70                  75                  80

Pro Ile Gly Val Tyr Thr Ser Gly Lys Gly Ser Ser Ala Ala Gly Leu
                85                  90                  95

Thr Ala Ser Val Met Arg Asp Pro Val Ser Arg Asn Phe Ile Met Glu
            100                 105                 110

Gly Gly Ala Met Val Leu Ala Asp Gly Gly Val Val Cys Ile Asp Glu
        115                 120                 125

Phe Asp Lys Met Arg Glu Asp Arg Val Ala Ile His Glu Ala Met Glu
    130                 135                 140

Gln Gln Thr Ile Ser Ile Ala Lys Ala Gly Ile Thr Thr Thr Leu
145                 150                 155                 160

Asn Ser Arg Cys Ser Val Leu Ala Ala Ala Asn Ser Val Tyr Gly Arg
                165                 170                 175

Trp Asp Asp Thr Lys Gly Glu Glu Asn Ile Asp Phe Met Pro Thr Ile
            180                 185                 190

Leu Ser Arg Phe Asp Met Ile Phe Ile Val Lys Asp Glu His Asn Glu
        195                 200                 205

Gln Arg Asp Met Thr Leu Ala Lys His Val Met Asn Val His Leu Ser
    210                 215                 220

Ala Arg
225
```

<210> SEQ ID NO 56
<211> LENGTH: 225
<212> TYPE: PRT

<213> ORGANISM: Xenopus sp.

<400> SEQUENCE: 56

```
Ile Val Ala Leu Ser Lys Asp Glu Arg Ile Gly Glu Arg Ile Phe Ala
1               5                   10                  15

Ser Ile Ala Pro Ser Ile Tyr Gly His Glu Asp Ile Lys Arg Gly Leu
            20                  25                  30

Ala Leu Ala Leu Phe Gly Gly Glu Ala Lys Asn Pro Gly Gly Lys His
        35                  40                  45

Lys Val Arg Gly Asp Ile Asn Val Leu Leu Cys Gly Asp Pro Gly Thr
    50                  55                  60

Ala Lys Ser Gln Phe Leu Lys Tyr Val Glu Lys Val Ala Ser Arg Ala
65                  70                  75                  80

Val Phe Thr Thr Gly Gln Gly Ala Ser Ala Val Gly Leu Thr Ala Tyr
                85                  90                  95

Val Gln Arg His Pro Val Thr Lys Glu Trp Thr Leu Glu Ala Gly Ala
            100                 105                 110

Leu Val Phe Ala Asp Arg Gly Val Cys Leu Ile Asp Glu Phe Asp Lys
        115                 120                 125

Met Asn Asp Gln Asp Arg Thr Ser Ile His Glu Ala Met Glu Gln Gln
    130                 135                 140

Ser Ile Ser Ile Ser Lys Ala Gly Ile Val Thr Ser Leu Gln Ala Arg
145                 150                 155                 160

Cys Thr Val Ile Ala Ala Ser Asn Pro Ile Gly Gly Arg Tyr Asp Pro
                165                 170                 175

Ser Leu Thr Phe Ser Glu Asn Val Asp Leu Thr Glu Pro Ile Val Ser
            180                 185                 190

Arg Phe Asp Ile Leu Cys Val Val Arg Asp Thr Val Asp Pro Val Gln
        195                 200                 205

Asp Glu Met Leu Ala Arg Phe Val Val Ser Ser His Ile Lys His His
    210                 215                 220

Pro
225
```

<210> SEQ ID NO 57
<211> LENGTH: 230
<212> TYPE: PRT
<213> ORGANISM: Xenopus sp.

<400> SEQUENCE: 57

```
Val Glu Lys Ile Gln Gln Val Ser Lys Arg Asp Asp Ile Tyr Asp Ile
1               5                   10                  15

Leu Ser Arg Ser Leu Ala Pro Ser Ile Tyr Glu Met Asp Asp Val Lys
            20                  25                  30

Lys Gly Leu Leu Leu Gln Leu Phe Gly Gly Thr Asn Lys Ser Phe His
        35                  40                  45

Lys Gly Ala Ser Pro Arg Tyr Arg Gly Asp Ile Asn Ile Leu Met Cys
    50                  55                  60

Gly Asp Pro Ser Thr Ser Lys Ser Gln Ile Leu Lys Tyr Val His Lys
65                  70                  75                  80

Ile Ala Pro Arg Gly Val Tyr Thr Ser Gly Lys Gly Ser Ser Ala Val
                85                  90                  95

Gly Leu Thr Ala Tyr Ile Thr Arg Asp Gln Asp Thr Lys Gln Leu Val
            100                 105                 110

Leu Glu Ser Gly Ala Leu Val Leu Ser Asp Gly Gly Ile Cys Cys Ile
        115                 120                 125
```

```
Asp Glu Phe Asp Lys Met Ser Asp Ala Thr Arg Ser Ile Leu His Glu
    130                 135                 140

Val Met Glu Gln Gln Thr Val Thr Val Ala Lys Ala Gly Ile Ile Thr
145                 150                 155                 160

Thr Leu Asn Ala Arg Thr Ser Ile Leu Ala Ser Ala Asn Pro Ile Gly
                165                 170                 175

Ser Lys Tyr Asn Pro Asp Leu Pro Val Thr Lys Asn Ile Asp Leu Pro
            180                 185                 190

Pro Thr Leu Leu Ser Arg Phe Asp Leu Val Tyr Leu Ile Leu Asp Arg
        195                 200                 205

Val Asp Glu Thr Leu Asp Arg Lys Leu Ala Asn His Ile Val Ser Met
    210                 215                 220

Tyr Met Glu Asp Thr Pro
225                 230

<210> SEQ ID NO 58
<211> LENGTH: 228
<212> TYPE: PRT
<213> ORGANISM: Xenopus sp.

<400> SEQUENCE: 58

Trp Glu Lys Val Phe Glu Met Ser Gln Asp Lys Asn Leu Tyr His Asn
1               5                   10                  15

Leu Cys Thr Ser Leu Phe Pro Thr Ile His Gly Asn Asp Glu Ile Lys
            20                  25                  30

Arg Gly Val Leu Leu Met Leu Phe Gly Gly Val Pro Lys Thr Thr Met
        35                  40                  45

Glu Gly Thr Ser Leu Arg Gly Asp Ile Asn Val Cys Ile Val Gly Asp
    50                  55                  60

Pro Ser Thr Ser Lys Ser Gln Phe Leu Lys His Val Glu Glu Phe Ser
65                  70                  75                  80

Pro Arg Ala Val Tyr Thr Ser Gly Lys Ala Ser Ser Ala Ala Gly Leu
                85                  90                  95

Thr Ala Ala Val Val Lys Asp Glu Glu Ser His Glu Phe Val Ile Glu
            100                 105                 110

Ala Gly Ala Leu Met Leu Ala Asp Asn Gly Val Cys Cys Ile Asp Glu
        115                 120                 125

Phe Asp Lys Met Asp Leu Lys Asp Gln Val Ala Ile His Glu Ala Met
130                 135                 140

Glu Gln Gln Thr Ile Ser Ile Thr Lys Ala Gly Val Lys Ala Thr Leu
145                 150                 155                 160

Asn Ala Arg Thr Ser Ile Leu Ala Ala Ala Asn Pro Val Gly Gly Arg
                165                 170                 175

Tyr Glu Arg Ser Lys Ser Leu Lys His Asn Val Asn Leu Ser Ala Pro
            180                 185                 190

Ile Met Ser Arg Phe Asp Leu Phe Phe Ile Leu Val Asp Glu Cys Asn
        195                 200                 205

Glu Val Thr Asp Tyr Ala Ile Ala Arg Arg Ile Val Asp Leu His Ala
    210                 215                 220

Arg Asn Glu Glu
225

<210> SEQ ID NO 59
<211> LENGTH: 239
<212> TYPE: PRT
<213> ORGANISM: Xenopus sp.
```

```
<400> SEQUENCE: 59

Leu Tyr Ala Ile Gln Glu Ile Gln Ser Gln Glu Asn Leu Phe Gln Leu
1               5                   10                  15

Ile Val Asn Ser Leu Cys Pro Thr Ile Tyr Gly His Glu Leu Val Lys
            20                  25                  30

Ala Gly Leu Ser Leu Ala Leu Phe Gly Gly Cys Gln Lys Tyr Ala Asp
        35                  40                  45

Asp Lys Asn Arg Ile Pro Ile Arg Gly Asp Pro His Ile Leu Val Val
    50                  55                  60

Gly Asp Pro Gly Leu Gly Lys Ser Gln Met Leu Gln Ala Val Cys Asn
65                  70                  75                  80

Val Ala Pro Arg Gly Val Tyr Val Cys Gly Asn Thr Thr Thr Thr Ser
                85                  90                  95

Gly Leu Thr Val Thr Leu Ser Arg Asp Thr Thr Gly Asp Phe Gly
            100                 105                 110

Leu Glu Ala Gly Ala Leu Val Leu Gly Asp Gln Gly Ile Cys Gly Ile
        115                 120                 125

Asp Glu Phe Asp Lys Met Gly Asn Gln His Gln Ala Leu Leu Glu Ala
    130                 135                 140

Met Glu Gln Gln Ser Ile Ser Leu Ala Lys Ala Gly Ile Val Cys Ser
145                 150                 155                 160

Leu Pro Ala Arg Thr Ser Ile Ile Ala Ala Asn Pro Val Gly Gly
                165                 170                 175

His Tyr Asn Lys Gly Lys Thr Val Ser Glu Asn Leu Lys Met Gly Ser
            180                 185                 190

Ala Leu Leu Ser Arg Phe Asp Leu Val Phe Ile Leu Val Asp Thr Pro
        195                 200                 205

Asn Glu Asp His Asp His Leu Leu Ser Glu His Val Met Ala Met Arg
    210                 215                 220

Ser Gly Ala Lys Glu Ile Gln Ser Val Asp Ile Thr Arg Ile Asn
225                 230                 235

<210> SEQ ID NO 60
<211> LENGTH: 224
<212> TYPE: PRT
<213> ORGANISM: Xenopus sp.

<400> SEQUENCE: 60

Asp Phe Trp Val Lys Tyr Arg Asn Asn Pro Leu Glu Gly Arg Asn Glu
1               5                   10                  15

Ile Leu Ala Ser Leu Cys Pro Gln Val Phe Gly Met Phe Val Val Lys
            20                  25                  30

Leu Ala Val Ala Met Val Leu Ala Gly Gly Val Gln Arg Ile Asp Ser
        35                  40                  45

Ala Gly Thr Arg Val Arg Gly Glu Ser His Leu Leu Val Gly Asp
    50                  55                  60

Pro Gly Thr Gly Lys Ser Gln Phe Leu Lys Tyr Ala Ala Lys Ile Thr
65                  70                  75                  80

Pro Arg Ser Val Leu Thr Ala Gly Ile Gly Ser Thr Ser Ala Gly Leu
                85                  90                  95

Thr Val Thr Ala Val Lys Asp Ser Gly Glu Trp Asn Leu Glu Ala Gly
            100                 105                 110

Ala Leu Val Leu Ala Asp Gly Gly Leu Cys Cys Ile Asp Glu Phe Asn
        115                 120                 125
```

```
Ser Ile Lys Glu His Asp Arg Thr Ser Ile His Glu Ala Met Glu Gln
    130                 135                 140

Gln Thr Ile Ser Val Ala Lys Ala Gly Leu Val Cys Lys Leu Asn Thr
145                 150                 155                 160

Arg Thr Thr Ile Leu Ala Ala Thr Asn Pro Lys Gly Gln Tyr Asp Pro
                165                 170                 175

Asp Glu Ser Ile Ser Val Asn Val Ala Leu Ala Ser Pro Leu Leu Ser
            180                 185                 190

Arg Phe Asp Leu Val Leu Val Leu Leu Asp Thr Lys Asn Glu Asp Trp
        195                 200                 205

Asp Arg Ile Ile Ser Ser Phe Ile Leu Glu Ser Lys Gly Cys Pro Arg
    210                 215                 220

<210> SEQ ID NO 61
<211> LENGTH: 494
<212> TYPE: PRT
<213> ORGANISM: Xenopus sp.

<400> SEQUENCE: 61

Leu Gln Arg Leu Glu Arg Gln Gln Ser Glu Asp Ser Leu Glu Ser Asp
1               5                   10                  15

Leu Gly Glu Ser Ala Thr Asn Leu Val Gly His Lys Val Val His Ser
            20                  25                  30

Glu Cys Val Met Glu Glu Thr Phe Ser Thr Phe Glu Ala Ser Ser Leu
        35                  40                  45

Pro Asp Glu Thr His Leu Gly Val Thr Gly Ser Ala Ala Phe Ile Gln
    50                  55                  60

Thr Pro Lys Lys Thr Ile Ser Asp Met Thr Lys Ser Asp Asp Thr Ile
65                  70                  75                  80

Arg Lys Gly Thr Ile Thr Pro Ala Glu Gln Asn Arg Gly Ile Ser Thr
                85                  90                  95

Asp Ala Glu Ser Ser Leu Lys Gln Gly Asn Ala Gln Pro Leu Ala Gly
            100                 105                 110

Gly His Leu Ser Glu Asn Asn Leu Thr Lys Cys Thr Asp Asn Ser Leu
        115                 120                 125

Gly Trp Phe Asp Thr Leu Gln Ser Ile Gln Met Ser Pro Ile Thr Lys
    130                 135                 140

Gln Arg Glu Gly Cys Thr Ala Glu Lys Leu Gln Gln Glu Val Leu Pro
145                 150                 155                 160

Val Ser Thr Glu Ser Ser Cys His Pro Ala Asp Lys Lys Val Val Asn
                165                 170                 175

Leu Gly Gly Arg Asn Lys Leu Glu Val Leu Gln Ala Ser Gly Ser Ser
            180                 185                 190

Pro Gly Gly Asn Gly Arg Asp Leu Ser Asn His Thr Val Thr Cys Gly
        195                 200                 205

Ser Ser Pro Glu Arg Asn Lys Arg Asp Leu Ser Asn His Ile Val Thr
    210                 215                 220

Glu His Val Ser Lys Lys Trp Arg Arg Ile Asn Lys Asp Ser Leu Cys
225                 230                 235                 240

Gly Lys Asn Val Pro Ser Phe Gln Pro Gln Ser Glu Asn Thr Asp Ser
                245                 250                 255

Ala Pro Val Cys Ser Ser Val Pro Leu His Ser Thr Pro Asp Val Ala
            260                 265                 270

Gln Arg Arg Lys Arg Ile Ile Ala Gln Val Glu Lys Gln Ser Lys Ala
        275                 280                 285
```

```
Glu Val Glu Asp Pro Asp Thr Lys Ala Arg Leu Ala Gln Leu Ala Lys
    290                 295                 300

Phe Ser Phe Lys Arg His Ser Lys Leu Val His Ser Pro Ala Gly Asp
305                 310                 315                 320

Thr Asp Thr Ala Ser Asn Ala Gln Lys His Asp His Pro Val Gln Lys
                325                 330                 335

Ile Thr Leu Ser Glu Lys Leu Asn Asn Leu Gly Arg Thr Val Asn Asn
                340                 345                 350

Val Asp Lys Ser Ser Asn Ser Val Asn Gly Ser Lys Gln Gln Lys His
            355                 360                 365

Val Glu Asn Thr Ser Lys Gln Thr Val Ile Thr Gln Lys Ser Asn Phe
    370                 375                 380

Glu Ser Asn Thr Leu Asn Ala Pro Val His Glu Thr Lys Leu Asn Glu
385                 390                 395                 400

Gly Cys Asp Ser Arg Lys Val Ser Ser Ser Thr Leu Ala Lys Leu Ala
                405                 410                 415

Arg Phe Ser Phe Ser Pro Pro Glu Asn Gln Ala Ala Glu Thr Ser
                420                 425                 430

Lys Glu Thr Leu Ile Leu Pro Arg Ala Val Ala Pro Gly Ser Lys Arg
            435                 440                 445

Lys Cys Phe Glu Leu Asn Pro Ser Thr Asp Lys Thr Thr Met Ser Ser
450                 455                 460

Lys Ser Leu Phe Ser Thr Thr Asp Leu Asp Glu Glu Leu Asp Val
465                 470                 475                 480

Asp Trp Glu Ala Glu Ile Lys Gly Asn Gln Arg Ile Ala Thr
                485                 490

<210> SEQ ID NO 62
<211> LENGTH: 520
<212> TYPE: PRT
<213> ORGANISM: Gallus gallus

<400> SEQUENCE: 62

Glu Leu Gln Arg Leu Asp Arg Leu Gln Lys Glu Thr Tyr Cys Gln Leu
1               5                   10                  15

Gln Pro Glu Glu Thr Ser Phe Ser Thr Ile Thr Gly Cys Leu Asn Lys
                20                  25                  30

Asn Thr Phe Glu Ser Lys Gln Lys Ser Gln Ser Glu Pro Ser Asp Gln
            35                  40                  45

Gln Lys Ile Asn Ser Tyr Pro Gln Pro Ser Leu Pro Lys Ser Asn Cys
        50                  55                  60

Glu Gly Asp Lys His Pro Glu Ala Leu Arg Asn Pro Thr Pro Gly Asn
65                  70                  75                  80

Asn Ile Ser Thr Lys Arg Leu Ser Arg Leu Asn Lys Arg Ser Asp Asp
                85                  90                  95

Gly Ser Leu Gly Trp Phe Asp Arg Leu Glu Asp Arg Asn Thr Asp Ala
            100                 105                 110

Glu Glu Thr Phe Trp Lys Thr Ser Pro Leu Pro Lys Thr Ser Pro Asp
        115                 120                 125

Asn Met Ala Leu Lys Thr Met Ser Lys Ser Ser Cys Ser Glu Glu Gly
    130                 135                 140

Asn Ser Ser Val Pro Arg Lys Glu Asp Gly Met Arg Gly Ser Leu Arg
145                 150                 155                 160

Thr Val Thr Leu Cys Ala Pro Leu Glu Gln Asp Lys Val Ser Glu Ile
                165                 170                 175
```

Ser Ser Lys Arg Thr Glu Glu Arg Lys Cys Phe Ser Ser Glu Ala Asn
        180                 185                 190

Ile Gln Asp Pro Thr Ser Ala Ser Val Gln Glu Ser Val Ile
    195                 200                 205

Thr Gln Arg Val Ser Lys Ser Leu Gln Arg Leu His Thr Glu Lys Ser
    210                 215                 220

His Arg Phe Phe Thr Ser Thr Gln Asn Ser Glu Ala Asn Ala Leu Pro
225                 230                 235                 240

Ser Val Leu Pro Val Ser Gly Leu Leu Asp Leu Ser Ser Asp Thr Asp
                245                 250                 255

Ser Val Val Gly Asp Glu Ser Asn Ser Ala Ser Ala Ala Val Lys His
            260                 265                 270

Ala Val Ile Ser Met Arg Lys Arg Ser Lys Gly Gln Ala Glu Lys Glu
        275                 280                 285

Ala Lys Ala Val Ser Ser His Glu Pro Glu Ile Thr Asp Gly Glu Ser
    290                 295                 300

Pro Pro Ala Ala Lys Leu Ala Lys Phe Ser Phe Arg Pro Arg Thr Lys
305                 310                 315                 320

Leu Asp Asp Ser Ser Glu Lys Lys Asn Ala Glu Phe Pro Leu Phe Pro
                325                 330                 335

Ser Glu Asn Thr Val Lys Pro Gly Glu Gln Pro Gln Gly Gln Leu
            340                 345                 350

Gln Lys Asp Cys Cys Pro Pro Glu Lys Arg Lys Met Thr Leu Thr Cys
        355                 360                 365

Leu Gly Arg Lys Gly Leu Glu Lys Gln Ser Ile Gly Ser Lys Gly Asn
    370                 375                 380

Glu Glu Gln Leu Ser Gln Ala Leu Gly Lys Glu Met Gly Gly Asn Ala
385                 390                 395                 400

Leu Ile His Ser Asp Val Thr Leu Asp Val Val Ser Pro Pro Thr
                405                 410                 415

Glu Lys Arg Arg Glu Gly Glu Gly Lys Leu Gly Gly Pro Ser Thr Val
            420                 425                 430

Arg Val Cys Ser Ser Thr Leu Glu Asn Leu Ser Lys Phe Cys Phe Ala
        435                 440                 445

Ser Arg Pro Asp Ser Lys Ser Glu Ala Pro Pro Thr Ile Lys Thr Asp
    450                 455                 460

Thr Asn Asn Lys Glu Ser His Ser Pro Leu Leu Lys Val His Val Ser
465                 470                 475                 480

Asn Pro Asn Lys Arg Lys Ser Phe Ala Leu Gly Asn Ala Ser Lys Asp
                485                 490                 495

Ser Val Val Thr Arg Lys Ser Leu Phe Ser Ile Ala Glu Leu Asp Asp
            500                 505                 510

Ala Thr Leu Asp Phe Asp Trp Asp
        515                 520

<210> SEQ ID NO 63
<211> LENGTH: 491
<212> TYPE: PRT
<213> ORGANISM: Mus musculus

<400> SEQUENCE: 63

Leu Leu Gln Glu Glu Leu Arg Arg Leu Glu Arg Leu Gln Asn Glu Ser
1               5                   10                  15

Val His Gln Cys Gln Ser His Ser Leu Glu Glu Glu Val Ala Pro Gly
                20                  25                  30

-continued

```
Ser Cys Arg Asn Asp Pro Arg Asp Lys Pro Arg Leu Arg Thr Ser Thr
             35                  40                  45

Gln Gln Glu Gln Ser Cys Ser Trp Ser Ser Thr Glu Arg Ser Gly Ala
 50                  55                  60

Asp Ser Pro Pro Gly Pro Gly Leu Asn Arg Pro Thr Ser Cys Asn Asn
 65                  70                  75                  80

Ser Ala Glu Asn Arg Asp Gly Arg Gly Asp Gly Leu Asp Trp Leu Asp
                 85                  90                  95

Pro Thr Ser Ser Pro Glu Ile Ala Pro Glu Ser Thr Ile Val Ser Pro
                100                 105                 110

Asn Val Lys Thr Thr Glu Lys Asn Val Asn Leu Lys Ile Ser Asn Asn
             115                 120                 125

Lys Ser Gln Gly Lys Glu Lys His Gly Pro Gln Gln Arg Ser Lys Leu
130                 135                 140

Leu Glu Ala Gly His Leu Pro Ser Ser Gly Ala Met Asn Ala Pro Leu
145                 150                 155                 160

Arg Ser His Gly Val Lys Arg Thr Lys Ala Ser Gln Ala Val Val Val
                165                 170                 175

Ser Glu Ala Gly Arg Gly Asp Glu Glu Asp Ser Val Pro Arg Arg Leu
            180                 185                 190

Pro Lys Leu Leu Lys Glu Gly Ser Gln Asn Val Cys Arg Ser Thr Thr
            195                 200                 205

Arg Val Arg Pro Leu Pro Pro Thr Val Pro Leu Ser Leu Ser Ile Pro
210                 215                 220

Ser Pro Gly Ser Gly Lys Arg Ser Gly Thr Pro Lys Arg Lys Arg Arg
225                 230                 235                 240

Lys Ser Ala Gln Val Glu Glu Pro Glu Pro Glu Gly Met Glu Thr Pro
                245                 250                 255

Thr Val Lys Leu Ala Lys Phe Thr Phe Lys Gln Lys Thr Lys Leu Thr
            260                 265                 270

His Ser Pro Glu Gly Gln Gly Pro Ile Pro Ser Ala Ser Glu Ile
            275                 280                 285

Ala Val Asp Ser Ser Lys Ile Pro Gln Gln Arg Thr Arg Arg Glu Ala
290                 295                 300

Ala Val Pro Val Val Ala Pro Gly Lys Ser Thr Ser Thr Ser Gly Asp
305                 310                 315                 320

Arg Cys Ser Asp Gln Leu His Gly Lys Thr Lys Glu Leu Ser Arg Gln
                325                 330                 335

Pro Pro Asp Ser Asn Pro Pro Arg Glu Glu Arg Glu Gln Gly Pro Lys
            340                 345                 350

Arg Arg Val Ile Gln Pro Lys Pro Glu Leu Gly Asn Gln Ala Gly His
            355                 360                 365

Ser His Leu Ala Cys Glu Lys Asp Arg Lys Glu Gly Val Ser Cys Gly
370                 375                 380

Asn Lys Ser Ser Lys Val His Ala Gly Thr Ile Ala Arg Leu Ala Ser
385                 390                 395                 400

Phe Ser Phe Thr Ser Pro Ser Glu Ser Lys Ser Glu Ser Leu Pro Pro
                405                 410                 415

Glu Arg Lys Asp Ser Arg Asp Ser Arg Asp Ser Arg Asp Ser Arg Asp
            420                 425                 430

Arg Cys His Ser Pro Pro Ala Thr Thr Ala Pro Val Leu Gly Gln Gln
            435                 440                 445

Arg Gln Thr Phe Gln Leu Gln Gln Pro Thr Glu Arg Ala Asn Leu Ser
450                 455                 460
```

```
Thr Leu Ser Leu Phe Thr Leu Ser Glu Leu Asp Asp Glu Ala Leu Asp
465                 470                 475                 480

Phe Asp Trp Glu Glu Glu Met Arg Lys Lys Pro
                485                 490

<210> SEQ ID NO 64
<211> LENGTH: 494
<212> TYPE: PRT
<213> ORGANISM: Homo sapiens

<400> SEQUENCE: 64

Arg Arg Leu Glu Arg Leu Gln Asn Gln Ser Val His Gln Ser Gln Pro
1               5                   10                  15

Arg Val Leu Glu Val Glu Thr Thr Pro Gly Ser Leu Arg Asn Gly Pro
            20                  25                  30

Gly Glu Glu Ser Asn Phe Arg Thr Ser Ser Gln Gln Glu Ile Asn Tyr
        35                  40                  45

Ser Thr His Ile Phe Ser Pro Gly Gly Ser Pro Glu Gly Ser Pro Val
    50                  55                  60

Leu Asp Pro Pro Pro His Leu Glu Pro Asn Arg Ser Thr Ser Arg Lys
65                  70                  75                  80

His Ser Ala Gln His Lys Asn Asn Arg Asp Asp Ser Leu Asp Trp Phe
                85                  90                  95

Asp Phe Met Ala Thr His Gln Ser Glu Pro Lys Asn Thr Val Val Val
            100                 105                 110

Ser Pro His Pro Lys Thr Ser Gly Glu Asn Met Ala Ser Lys Ile Ser
        115                 120                 125

Asn Ser Thr Ser Gln Gly Lys Glu Lys Ser Glu Pro Gly Gln Arg Ser
    130                 135                 140

Lys Val Asp Ile Gly Leu Leu Pro Ser Pro Gly Glu Thr Gly Val Pro
145                 150                 155                 160

Trp Arg Ala Asp Asn Val Glu Ser Asn Lys Lys Arg Leu Ala Leu
                165                 170                 175

Asp Ser Glu Ala Ala Val Ser Ala Asp Lys Pro Asp Ser Val Leu Thr
            180                 185                 190

His His Val Pro Arg Asn Leu Gln Lys Leu Cys Lys Glu Arg Ala Gln
        195                 200                 205

Lys Leu Cys Arg Asn Ser Thr Arg Val Pro Ala Gln Cys Thr Val Pro
    210                 215                 220

Ser His Pro Gln Ser Thr Pro Val His Ser Pro Asp Arg Arg Leu Asp
225                 230                 235                 240

Ser Pro Lys Arg Lys Arg Pro Lys Ser Leu Ala Gln Val Glu Glu Pro
                245                 250                 255

Ala Ile Glu Asn Val Lys Pro Gly Ser Pro Val Ala Lys Leu Ala
            260                 265                 270

Lys Phe Thr Phe Lys Gln Lys Ser Lys Leu Ile His Ser Phe Glu Asp
        275                 280                 285

His Ser His Val Ser Pro Gly Ala Thr Lys Ile Ala Val His Ser Pro
    290                 295                 300

Lys Ile Ser Gln Arg Arg Thr Arg Arg Asp Ala Ala Leu Pro Val Lys
305                 310                 315                 320

Arg Pro Gly Lys Leu Thr Ser Thr Pro Gly Asn Gln Ile Ser Ser Gln
                325                 330                 335

Pro Gln Gly Glu Thr Lys Glu Val Ser Gln Gln Pro Pro Glu Lys His
            340                 345                 350
```

```
Gly Pro Arg Glu Lys Val Met Cys Ala Pro Glu Lys Arg Ile Ile Gln
            355                 360                 365
Pro Glu Leu Glu Leu Gly Asn Glu Thr Gly Cys Ala His Leu Thr Cys
        370                 375                 380
Glu Gly Asp Lys Lys Glu Val Ser Gly Ser Asn Lys Ser Gly Lys
385                 390                 395                 400
Val His Ala Cys Thr Leu Ala Arg Leu Ala Asn Phe Cys Phe Thr Pro
                405                 410                 415
Pro Ser Glu Ser Lys Ser Lys Ser Pro Pro Glu Arg Lys Asn Arg
            420                 425                 430
Gly Glu Arg Gly Pro Ser Ser Pro Thr Thr Ala Pro Met Arg
        435                 440                 445
Val Ser Lys Arg Lys Ser Phe Gln Leu Arg Gly Ser Thr Glu Lys Leu
            450                 455                 460
Ile Val Ser Lys Glu Ser Leu Phe Thr Leu Pro Glu Leu Gly Asp Glu
465                 470                 475                 480
Ala Phe Asp Cys Asp Trp Asp Glu Met Arg Lys Lys Ser
                485                 490

<210> SEQ ID NO 65
<211> LENGTH: 20
<212> TYPE: PRT
<213> ORGANISM: Homo sapiens

<400> SEQUENCE: 65

Glu Thr Lys Glu Val Ser Gln Gln Pro Pro Lys His Gly Pro Arg
1               5                   10                  15
Glu Lys Val Met
            20

<210> SEQ ID NO 66
<211> LENGTH: 20
<212> TYPE: PRT
<213> ORGANISM: Homo sapiens

<400> SEQUENCE: 66

Pro Trp Arg Ala Asp Asn Val Glu Ser Asn Lys Lys Lys Arg Leu Ala
1               5                   10                  15
Leu Asp Ser Glu
            20

<210> SEQ ID NO 67
<211> LENGTH: 18
<212> TYPE: DNA
<213> ORGANISM: Artificial Sequence
<220> FEATURE:
<223> OTHER INFORMATION: Synthetic primer

<400> SEQUENCE: 67
tacaggaaca cgggtcag                                                18

<210> SEQ ID NO 68
<211> LENGTH: 18
<212> TYPE: DNA
<213> ORGANISM: Artificial Sequence
<220> FEATURE:
<223> OTHER INFORMATION: Sythetic primer

<400> SEQUENCE: 68
gaaacatcag gcgagcat                                                18
```

```
<210> SEQ ID NO 69
<211> LENGTH: 18
<212> TYPE: DNA
<213> ORGANISM: Artificial Sequence
<220> FEATURE:
<223> OTHER INFORMATION: Synthetic primer

<400> SEQUENCE: 69
tacaggaaca cgggtcag                                                  18

<210> SEQ ID NO 70
<211> LENGTH: 21
<212> TYPE: DNA
<213> ORGANISM: Artificial Sequence
<220> FEATURE:
<223> OTHER INFORMATION: Synthetic primer

<400> SEQUENCE: 70
tgccatgaaa tcaaaccaat c                                              21

<210> SEQ ID NO 71
<211> LENGTH: 21
<212> TYPE: DNA
<213> ORGANISM: Artificial Sequence
<220> FEATURE:
<223> OTHER INFORMATION: Synthetic primer

<400> SEQUENCE: 71
tttgatttca tggcaactca t                                              21

<210> SEQ ID NO 72
<211> LENGTH: 21
<212> TYPE: DNA
<213> ORGANISM: Artificial Sequence
<220> FEATURE:
<223> OTHER INFORMATION: Synthetic primer

<400> SEQUENCE: 72
cgcattggag ctgtggttgt a                                              21

<210> SEQ ID NO 73
<211> LENGTH: 21
<212> TYPE: DNA
<213> ORGANISM: Artificial Sequence
<220> FEATURE:
<223> OTHER INFORMATION: Synthetic primer

<400> SEQUENCE: 73
ttgatagtgc actgcgaagg t                                              21

<210> SEQ ID NO 74
<211> LENGTH: 19
<212> TYPE: DNA
<213> ORGANISM: Artificial Sequence
<220> FEATURE:
<223> OTHER INFORMATION: Synthetic primer

<400> SEQUENCE: 74
tgcattacaa tcccgtaaa                                                 19

<210> SEQ ID NO 75
<211> LENGTH: 33
<212> TYPE: DNA
<213> ORGANISM: Artificial Sequence
<220> FEATURE:
<223> OTHER INFORMATION: Synthetic primer
```

```
<400> SEQUENCE: 75
gggggggtcg accagccatt acctagattc aag                                33

<210> SEQ ID NO 76
<211> LENGTH: 32
<212> TYPE: DNA
<213> ORGANISM: Artificial Sequence
<220> FEATURE:
<223> OTHER INFORMATION: Synthetic primer

<400> SEQUENCE: 76
ggggggctcg agcagaaagc ttttcccaac ta                                 32
```

USE OF A NEW GENE CODING FOR A NEW MEMBER OF THE MCM2-8 FAMILY IN PHARMACEUTICAL COMPOSITIONS

The present invention relates to the use of a new gene coding for a new member of the MCM2-8 family in pharmaceutical compositions.

The Minichromosome maintenance family (MCM2-7) comprises a group of six structurally related proteins required to initiate DNA synthesis in eukaryotes (Kearsey et al., 1998). These proteins function in a complex very likely as a DNA helicase in promoting the opening of the DNA double helix at replication origins. ATP binding (Walker A) and hydrolysis (Walker B) motifs are present in all MCM2-7 members, embedded in a region which is highly conserved in this protein family, also known as the MCM2-7 signature domain (Koonin, 1993). Recently, this protein family has expanded by the identification of a novel member, the MCM8 protein (Gozuacik et al., 2003, Johnson et al., 2003, Maiorano et al., 2005). Unlike MCM2-7, which are widely conserved in eukaryotes, MCM8 is present only in higher multicellular organisms, being absent in worms and yeast.

Very recently, another new member of the MCM protein family, the MCM9 protein, has been identified in humans (Yoshida, 2005). Intriguingly, the predicted human protein (HsMCM9) has been reported to be a rather short homolog of MCM proteins (391 aa against an average of 800 aa in MCM2-7 and MCM8 proteins) and the function of this protein is not known.

Anomalies during DNA replication process are involved in different pathologies such as brains diseases, haematological disorders and cancers. Thus, means to control cellular division would be useful tools for the treatment of pathologies linked to a dysfunction of DNA replication or for pathologies linked to an excessive cellular proliferation.

One of the aims of the invention is to provide a pharmaceutical composition for treating pathologies linked to a dysfunction of DNA replication or to an excessive cell proliferation.

One of the aims of the invention is to provide a method for inhibiting cell proliferation or enhancing DNA replication.

One of the aims of the invention is to provide a method for screening drugs useful in the treatment of pathologies linked to a dysfunction of the replication or to an excessive cell proliferation.

Another aspect of the invention relates to the identification of a MCM2-8 family protein, for which only a truncated form was known, and its specific function.

All these aspects have been obtained by the identification of the full-length MCM9 gene and MCM9 protein.

The invention relates to the use of the human or animal MCM9 gene, or parts of said gene, or transcripts thereof, or antisense nucleic acids able to hybridize with part of said transcripts, or silencing RNA derived from parts of said transcripts and able to repress said MCM9 gene, or proteins or peptidic fragments translated from said transcripts, or antibodies directed against said proteins or peptidic fragments for the preparation of a pharmaceutical composition for the treatment of a human or animal pathology linked to a dysfunction of the expression of the MCM9 gene, or of human or animal cancers.

The Inventors have performed the complete identification of a novel member of the MCM2-8 family represented by the members MCM2-7 and MCM8, the MCM9 protein. Like MCM8, MCM9 is only present in the genome of higher eukaryotes. This protein contains an MCM8-like ATP binding and -hydrolysis motif implicated in helicase activity. Strikingly, in addition, MCM9 contains a unique carboxy-terminal domain which has only weak homology to MCM2-7 and MCM8, but stretches of amino acids, ranging from 4 to 10 amino acids, are highly conserved within MCM9 homologs. The Inventors have also shown that the very recently reported human MCM9 protein, which resembles a truncated MCM-like protein missing a part of the MCM2-7 signature domain, is an incomplete form of the full length human MCM9 protein hMCM9 described here. Searching the human genome with either the newly identified human MCM9 or other MCM protein sequences, The Inventors have not detected further additional members of this DNA helicase family and suggest that it is constituted of eight members, falling into two different groups, one constituted by the MCM2-7 complex and the other by MCM8 and MCM9, which are present only in higher eukaryotes.

The term "MCM2-7" refers to proteins MCM2, MCM3, MCM4, MCM5, MCM6 and MCM7.

The term "MCM2-8" refers to proteins MCM2, MCM3, MCM4, MCM5, MCM6 MCM7 and MCM8.

DNA helicases have essential roles in nucleic acid metabolism, particularly during DNA replication, also called DNA duplication. Helicases are involved in unwinding DNA at replication origins, allowing DNA synthesis by recruiting DNA polymerases and they are also involved in the whole process of the elongation and termination phases of DNA synthesis when DNA has to be continuously and efficiently unwound. DNA helicases bind to single strand DNA either naked or coated with the single strand DNA binding protein RPA (Replication Protein A) as oligomeric complexes and catalyze the melting of the DNA double helix. This reaction is catalyzed by ATP hydrolysis. ATP binds the helicase at the ATP binding site (Walker A) and ATP hydrolysis occurs at the ATP hydrolysis motif (Walker B).

The helicase activity of a protein can be for example determined by the following test: the protein to test is incubated with a single-stranded DNA substrate annealed to a 40-mer oligonucleotide for 1 hour. The reaction products are then separated on an acrylamide gel. The helicase activity is revealed by the presence of single strand DNA, due to the unwinding of the dimer single-stranded DNA/oligonucleotide.

The ATPase activity can be monitored as described in Maiorano et al. (2005, Cell. 120, 315-28) or alternatively using acidic molybdate and malachite green as follows: the protein to be tested is incubated for 10 minutes at 37° C. in ATPase buffer (50 mM TrisHCl, pH 7.5; 2 mM $MgCl_2$; 1.5 mM DTT; 0.05% Tween-20; and 0.25% µg/ml BSA) with a $dT_{25}$ oligonucleotide or 500 ng of heat-denatured ssDNA. The reaction is started by the addition of ATP and incubation at 37° C. for up to 25 minutes. The reaction mixture is then transferred into the molybdate/malachite green solution and the absorbance is immediately read at 630 nMm ($OD_{360}$) to determine the amount of inorganic phosphate produced during the reaction.

The expression "dysfunction of the expression of the MCM9 gene" relates to an overexpression, a repression or an inhibition of the expression of the MCM9 gene, or relates to the expression of a protein coded by the MCM9 gene, which is not active or only partially active. A dysfunction of the MCM9 gene expression can particularly induce disorders in DNA replication.

A MCM9 protein is active or is an active form when said MCM9 protein has an helicase activity and an ATPase activity and stimulates the formation of a pre-replication complex by loading MCM2-7 onto chromatin. The pre-replication complex is a large protein complex made of the ORC1-6 proteins, Cdc6, Cdt1 and MCM2-7 proteins.

A MCM9 protein is partially active when said MCM9 protein has an helicase activity and/or an ATPase activity lower than the active form.

The helicase activity is lower than the helicase activity of the active form when it represents at least 30%, particularly at least 60%, and more particularly at least 90% of the helicase activity of the active form.

The ATPase activity is lower than the ATPase activity of the active form when it represents at least 30%, particularly at least 60%, and more particularly at least 90% of the ATPase activity of the active form.

A MCM9 protein is not active or is an inactive form when said MCM9 protein has no helicase and/or ATPase activity, or has an helicase activity lower than 30% of the helicase activity of the active form and/or has an ATPase activity lower than 30% of the ATPase activity of the active form, and/or poorly stimulates the formation of a pre-replication complex by loading MCM2-7 onto chromatin.

The dysfunction of the expression of the MCM9 gene can be assayed by the determination of the amount of MCM9 mRNA produced in the cell either by hybridization of total cellular RNA with either a DNA or RNA probe derived from the sequence of the MCM9 gene (Northern blot) or by PCR amplification of the MCM9 mRNA, following its conversion into cDNA by the use of a Reverse Transcriptase (RT-PCR), or by in situ hybridization with either DNA or RNA probes derived from the sequence of the MCM9 gene after fluorescent labelling of these probes. MCM9-specific antibodies can be also used to determine the levels of the MCM9 protein present in cells and/or tissues by western or by in situ hybridization on fixed tissues slices of isolated cells and/or nuclei.

The expression "pathologies linked to a dysfunction of the expression of the MCM9 gene" means that these pathologies result from disorders in helicase activity of the MCM9 gene.

The expression "parts of said gene" means fragments of the MCM9 gene.

The invention also relates to the use of transcripts of the MCM9 gene or of parts of the MCM9 gene. The translation of these transcripts, also called mRNAs, will produce the MCM9 protein, or peptidic fragments of said protein. The proteins or peptidic fragments can be purified from cells expressing said compounds. The peptidic fragments according to the invention can also be synthesized by any method of chemistry well-known in the art.

The invention further relates to the use of antisense nucleic acids. Antisense nucleic acids, also called antisense-oligonucleotides (AS-ONs) pair (hybridize) with their complementary mRNA target, thus blocking the translation of said mRNA or inducing the cleavage by RNase H of said mRNA inside the DNA/RNA complex. In both cases, the use of antisense nucleic acids induces a specific blocking of RNA translation. The antisense nucleic acids according to the invention comprise preferentially 10 to 30 nucleotides. The use of antisense nucleic acids able to hybridize with transcripts of the MCM9 gene thus allows inhibiting the expression of the MCM9 gene.

The expression "antisense nucleic acids able to hybridize with part of said transcripts" means that antisense nucleic acids will pair with part of said transcripts that are complementary under specific hybridation conditions.

Specific hybridization conditions may be determined according to "Molecular cloning", third edition, Sambrook and Russel, CSHL press, 2001.

The invention also relates to the use of silencing RNA, also called interfering RNA, derived from parts of transcripts of the MCM9 gene. RNA interference is a process initiated by double-strand RNA molecules (dsRNAs), which are cut by the cell machinery into 21-23 nucleotides long RNAs, called small interfering RNAs (siRNAs). In the cell, said siRNAs are then incorporated into RNA-Induced Silencing Complex (RISC), in which they guide a nuclease to degrade the target simple strand RNA. The use of silencing RNAs, which are complementary to parts of MCM9 transcripts, allows the specific inhibition of the MCM9 expression.

The invention further relates to the use of MCM9 proteins or peptidic fragments of said protein, which are translated from the transcripts of the MCM9 gene or fragments of said gene, respectively.

The invention also relates to the use of antibodies directed against MCM9 proteins or peptidic fragments of said protein. These antibodies thus bind to the MCM9 protein in the cell, thus inhibiting its helicase function.

The invention relates in particular to the use as defined above for the preparation of a pharmaceutical composition for the treatment of cancers, wherein the helicase activity of MCM9 and in particular of the polypeptide represented by SEQ ID NO 2 or SEQ ID NO 4 or SEQ ID NO 6 or SEQ ID NO 8 or SEQ ID NO 10 or SEQ ID NO 12 or SEQ ID NO 14 or SEQ ID NO 16 or SEQ ID NO 18 is inactivated in tumoral cells of the human or animal body by using silencing RNAi according to RNA interference, such as double-stranded RNA (dsRNA) for post-transcriptional gene silencing, or short interfering RNA (siRNA) or short hairpin RNA (shRNA) to induce specific gene suppression, or antisense DNA or RNA, or antibodies, in order to curb the proliferation of said tumoral cells.

In a particular embodiment, the invention aims at inhibiting the proliferation of cancer cells. For that purpose, the helicase activity in tumoral cells is inactivated by specifically blocking MCM9 expression using RNA interference or antisense nucleotides, or by blocking the MCM9 protein with specific antibodies. The level of active MCM9 and consequently the level of helicase activity are decreased and the DNA replication is curbed. The proliferation of the tumoral cells is thus inhibited and a stop of the DNA replication process may also induce apoptosis of the tumoral cells.

Blocking the MCM9 protein or its expression in a cell or in a specific tissue allows blocking of the cell cycle, even before DNA becomes licensed to replicate, which is before the MCM2-7 complex is loaded onto chromatin and DNA synthesis has been initiated. Such cells, which are blocked in this early state of the cell cycle, in particular at the M to G1 phase transition, can not proceed aberrantly in the cell cycle, but will either rest quiescent or be eliminated by apoptosis. In contrast, cells which are blocked or delayed after the licensing of their DNA for replication or even after replication has started, have a high risk to proliferate unfaithfully, to accumulate mutations and to inherit an unstable genome. The term "unstable genome" means that said cells have rearranged the structure of their genome, e.g. by accumulation of chromosomal abnormalities, so that they have a high probability to proliferate abnormally and to generate cancers.

Moreover, blocking MCM9 protein or its expression in a cell constitutes a more efficient treatment against cancer than current drugs that target cells in later phases of the cell cycle, such as the S and G2 phases. In these phases of the cell cycle, DNA replication has already been initiated and therefore cells can rearrange their genome, for example by homologous and/or non-homologous recombination, and therefore have a higher probability to develop resistance to the said drugs. Thus, using a drug that targets MCM9 overcomes the resistance of cancer cells to the said drugs, as the cell cycle is blocked before cancer cells have the possibility to adapt their genome.

The invention particularly relates to antibodies that block the binding of MCM9 on Cdt1 and/or on the chromatin. The inactivation of MCM9 assembly with Cdt1 or with the chromatin allows blocking the entry in the cell cycle before the loading of MCM2-7 onto chromatin, that is to say before licensing.

The term "licensing" means giving to the chromosomes the competence to replicate through the formation of pre-replication complexes onto DNA replication origins.

The pre-replication complex is a large protein complex made of the ORC1-6 proteins, Cdc6, Cdt1 and MCM2-7 proteins.

The protein Cdt is involved in the formation of pre-replication complexes.

The helicase activity in tumoral cells is particularly inactivated by specifically blocking the polypeptides represented by SEQ ID NO 2 or SEQ ID NO 4 or SEQ ID NO 6 or SEQ ID NO 8 or SEQ ID NO 10 or SEQ ID NO 12 SEQ ID NO 14 or SEQ ID NO 16 or SEQ ID NO 18, or their expression.

The polypeptide represented by SEQ ID NO 2 corresponds to the human MCM9 protein (1143 amino acids). The human MCM9 protein contains an ATP binding site (Walker A) and an ATP hydrolysis motif (Walker B).

The polypeptide represented by SEQ ID NO 4 corresponds to the fragment of the human MCM9 protein represented by SEQ ID NO 2, which extends from amino acid 385 to 1143.

The polypeptide represented by SEQ ID NO 6 corresponds to the truncated form of the human MCM9 protein described by Yoshida (2005), which extends from amino acid 1 to 384 of the human MCM9 protein represented by SEQ ID NO 2.

Alignment of the truncated human MCM9 protein described by Yoshida (2005) with the other MCM proteins suggested that this protein might be a truncated MCM like protein missing the carboxy-terminal half of the MCM2-7 signature domain. Within the truncated domain, the ATP binding site is present but the ATP hydrolysis motif is absent. Thus, this truncated form does not contain an ATP hydrolysis motif which is essential for DNA helicase activity (see example 1).

The polypeptide represented by SEQ ID NO 8 corresponds to the murine MCM9 protein (1290 amino acids).

The polypeptide represented by SEQ ID NO 10 corresponds to the fragment of the murine MCM9 protein represented by SEQ ID NO 8, which extends from amino acid 540 to 1290.

The polypeptide represented by SEQ ID NO 12 corresponds to the fragment of the murine MCM9 protein represented by SEQ ID NO 8, which extends from amino acid 1 to 539.

The polypeptide represented by SEQ ID NO 14 corresponds to the Xenopus MCM9 protein (1143 amino acids).

The polypeptide represented by SEQ ID NO 16 corresponds to the fragment of the Xenopus MCM9 protein represented by SEQ ID NO 14, which extends from amino acid 385 to 1143.

The polypeptide represented by SEQ ID NO 18 corresponds to the fragment of the Xenopus MCM9 protein represented by SEQ ID NO 14, which extends from amino acid 1 to 384.

The efficiency of inhibition of the helicase activity, obtained by specifically blocking MCM9 protein or its expression, can be determined by cell proliferation test. For example, classical tests based on BrdU incorporation during DNA synthesis can be used or other tests such as analysis of the DNA content of a cell population by Fluorescence Activated Cell Sorter (FACS), or by incorporation of either a radioactively labelled DNA precursor, or $H^3$ (tritium) into thrichloroaceticacid (TCA) insoluble materiel, or by scoring the mitotic index of a cell population, or by scoring the increase in the total mass of a cell population (growth curve), or the increase in the rate of protein synthesis, or by scoring the number of Ki67-, PCNA-, MCM2-7- or Cdc6-positive cells.

For the purpose of the invention, the RNA interference is obtained by using interfering RNA chosen among double-strand RNA, short interfering RNA or short hairpin RNA. Interfering RNA can be obtained by chemical synthesis or by DNA-vector technology.

A short hairpin RNA is a simple strand RNA, characterized in that the two ends of said RNA are complementary and can hybridize together, thus forming an artificial double strand RNA with a loop between the two ends.

The invention further relates to the use as defined above for the preparation of a pharmaceutical composition for the treatment of neoplastic diseases such as choriocarcinoma, liver cancer induced by DNA damaging agents or by infection by Hepatitis B virus, skin melanotic melanoma, melanoma, pre-malignant actinic keratose, colon adenocarcinoma, basal cell carcinoma, squamous cell carcinoma, ocular cancer, non-Hodgkin's lymphoma, acute lymphocytic leukaemia, meningioma, soft tissue sarcoma, osteosarcoma, and muscle rhabdomyosarcoma or of brain diseases such as Alzheimer disease, neuron degenerative diseases and mental retardation, or of hematological disorders.

The above-mentioned pathologies are linked to an excessive proliferation of the cells. The invention particularly relates to the use of a pharmaceutical composition that allows the inhibition of the proliferation of said cells.

The invention also relates to the above-mentioned use, for the preparation of a pharmaceutical composition for the treatment of a human or animal pathology linked to a dysfunction of the expression of the MCM9 gene, wherein the number of functional MCM9 helicases is increased or the activity of MCM9 helicases in cells of the human or animal body is stimulated by administration of functional MCM9 proteins and in particular of polypeptides represented by SEQ ID NO 2 or SEQ ID NO 4 or SEQ ID NO 6 or SEQ ID NO 8 or SEQ ID NO 10 or SEQ ID NO 12 or SEQ ID NO 14 or SEQ ID NO 16 or SEQ ID NO 18 or of fragments thereof or by gene or cell therapy.

In the above-mentioned use, the dysfunction of the expression of the MCM9 gene is linked to an inhibition or a repression of the expression of an active form of MCM9, or to the expression of an inactive form or a partially active form of the MCM9 protein.

The above-mentioned pathologies result from the absence or the small rate of helicase activity of the MCM9 protein, which may result from the expression of an inactive form of the MCM9 protein or from an expression of said protein which is between 1% to 60% smaller than the expression in normal cells.

The administration of said pharmaceutical composition enables to increase the number of functional MCM9 helicases or to stimulate the activity of MCM9 helicases.

The increased number of functional helicases can be determined by immunoblot with MCM9 specific antibodies on total cell lysates, or by in situ immunostaining on a given cell population or a tissue and/or by isolation of the MCM9 protein by immunopurification with MCM9-specific antibodies and determination of both helicase and ATPase activity in vitro compared to normal cells.

The stimulation of the MCM9 helicase activity is determined by performing an helicase test as described above in the presence of the single strand DNA annealed to an oligonucleotide, the single strand DNA binding trimeric complex RPA, or with DNA polymerases, PCNA, RF-C and/or other replication fork accessory proteins.

The expression "trimeric complex" means a protein complex made of three polypeptides.

The term "gene therapy" refers to the use of DNA as a drug. According to the invention, said DNA comprises the MCM9 gene and is introduced in the cells so that they can express the MCM9 protein. Gene transfer methods are well-known by the man skilled in the art. They comprise physical methods, such as naked DNA, microinjection, shotgun or electrotransfer, and vectorization using non-viral or viral vectors for the gene transfer.

According to the invention, the term "cell therapy" refers to the use of cells having a normal helicase activity to replace or repair cells that present a dysfunction in helicase activity.

According to another embodiment, the present invention relates to the use as defined above for the preparation of a pharmaceutical composition for the treatment of pathologies characterized by a predisposition towards cancer or premature aging and being notably caused by a defect of the helicase function and being particularly selected among Bloom's syndrome, Werner's syndrome, ataxia-telangectasia, xerodermia pigmentosum, Cockayne's syndrome and Rothmund-Thomson's syndrome.

The pathologies characterized by a predisposition towards cancer or premature aging are linked to an inhibition or a repression of the helicase activity, or to an aberrant helicase activity.

The expression "aberrant helicase activity" refers to cases wherein the DNA strand is not entirely synthesized or wherein mistakes are introduced in the new synthesized DNA strand.

The expression "predisposition towards cancer" refers to pathologies wherein the inhibition or the repression of the helicase activity or the aberrant helicase activity can lead to aberrant new synthesized DNA strand that may be responsible of an abnormally proliferation of the cells and then of the induction of cancers.

The expression "defect of the helicase function" refers to an inhibition or a repression of the helicase activity and particularly leads to a cell replication rate that is lower than 20%, by comparison with the replication rate in normal (healthy) cells.

The invention relates to pharmaceutical compositions that enable to restore an helicase activity, particularly by increasing the number of functional MCM9 helicases or to stimulating the activity of MCM9 helicases.

The present invention also relates to a peptide or polypeptide of one of the following sequences: SEQ ID NO 2 (amino-acids 1-1143 of hMCM9), SEQ ID NO 4 (amino-acids 385-1143 of hMCM9), SEQ ID NO 6 (amino-acids 1-384 of hMCM9), SEQ ID NO 8 (amino-acids 1-1290 of MmMCM9), SEQ ID NO 10 (amino-acids 540-1290 of MmMCM9), SEQ ID NO 12 (amino-acids 1-539 of MmMCM9), SEQ ID NO 14 (amino-acids 1-1143 of XMCM9), SEQ ID NO 16 (amino-acids 385-1143 of XMCM9), SEQ ID NO 18 (amino-acids 1-384 of XMCM9), or derived from one of the above-defined sequences by insertion, deletion, substitution of one or more amino-acids, or flanked by additional amino-acids at the N-terminus or at the C-terminus or at both termini, provided that the resulting sequence shares at least 55%, in particular at least 65%, in particular at least 80% identity with one of the above-defined sequences and provided that said peptide or polypeptide has substantially the same helicase and/or ATPase activity as the MCM9 protein, and in particular provided that the resulting sequence has a maximum length of 660 amino-acids and a minimum length of 300 amino-acids, or corresponding to a fragment thereof, provided that said fragment has substantially the same helicase and/or ATPase activity as the MCM9 protein.

The expression "peptide or polypeptide derived from one of the above-defined sequences" means that said peptide or polypeptide contains at least one mutation chosen among insertion (or addition) or deletion or substitution of one or more amino-acids, and/or that the peptide or polypeptide is flanked by additional amino-acids at the N-terminus or at the C-terminus or at both termini.

The mutation by substitution in the amino acid sequence can be a substitution by a conservative amino-acid or not.

The additional amino-acids can particularly be chosen among Walker A, Walker B and Zn-finger motifs.

The derived peptides or polypeptides of the invention may be more active forms than the native MCM9 protein and/or possess a modified helicase and/or ATPase activity, such as being able to metabolize other forms of ATP, for example N6-benzyl ATP, N6-cyclopentyl ATP.

The expression "the resulting sequence has a maximum length of 660 amino-acids and a minimum length of 300 amino-acids" particularly refers to peptides or polypeptides that are within the highly conserved MCM2-8-like N-terminus part of MCM9 protein and that comprise the MCM-2-8 family domain.

The highly conserved MCM2-8-like N-terminus part corresponds in the MCM9 protein to amino acids 1-650 for *Xenopus*, 1-805 for Mouse and 1-650 for Human.

The MCM-2-8 family domain corresponds in the MCM9 protein to amino acids 303-606 for *Xenopus*, 458-761 for Mouse and 302-605 for Human.

The expression "substantially the same helicase and/or ATPase activity as the MCM9 protein" means that the helicase and/or ATPase activity of the derived peptide or polypeptide is at least 60%, in particular at least 80% and more particularly at least 90% of the activity of the MCM9 protein.

The present invention also relates to a peptide or polypeptide derived from one of the following sequences: SEQ ID NO 2 (amino-acids 1-1143 of hMCM9), SEQ ID NO 4 (amino-acids 385-1143 of hMCM9), SEQ ID NO 6 (amino-acids 1-384 of hMCM9), SEQ ID NO 8 (amino-acids 1-1290 of MmMCM9), SEQ ID NO 10 (amino-acids 540-1290 of MmMCM9), SEQ ID NO 12 (amino-acids 1-539 of MmMCM9), SEQ ID NO 14 (amino-acids 1-1143 of XMCM9), SEQ ID NO 16 (amino-acids 385-1143 of XMCM9), SEQ ID NO 18 (amino-acids 1-384 of XMCM9), by at least one mutation located on a site of phosphorylation by CDKs, in particular said mutations being chosen among the followings:

modification of the conserved threonine (T) in the TP motif to alanine (A) or an equivalent amino acid and modification of the conserved serine (S) in the SP motif to alanine (A) or an equivalent amino acid, modification of the conserved threonine (T) in the TP motif to glutamate (E) or an equivalent amino acid and modification of the conserved serine (S) in the SP motif to glutamate (E) or an equivalent amino acid.

The potential SP phosphorylation sites in MCM9 proteins are located on amino acids 193-194, 478-479, 789-790, 841-842, 859-860, 965-966, 1070-1071 in *Xenopus*, amino acids 49-50, 75-76, 94-95, 348-349, 633-634, 865-866, 899-900, 910-911, 1024-1025, 1073-1074, 1204-1205, 1235-1236 in Mouse, and amino acids 192-193, 477-478, 703-704, 711-712, 762-763, 802-803, 883-884, 890-891, 915-916, 942-943, 952-953, 1073-1074, 1088-1089 in Human.

The potential TP phosphorylation sites in MCM9 proteins are located on amino acids 370-371, 714-715, 735-736, 917-918 in *Xenopus*, amino acids 127-128, 525-526, 1033-1034, 1054-1055 in Mouse, and amino acids 369-370, 673-674, 879-880, 977-978, 1064-1065 in Human.

CDKs (Cyclin-Dependent Kinases) are enzymes involved in the regulation of cell division cycle. CDKs activate and/or inactivate their substrate by phosphorylation. CDKs recognize specific sites, called "site of phosphorylation by CDK", particularly the amino-acids motifs TP and SP.

The mutated forms of MCM9 proteins obtained by mutations located on a site of phosphorylation by CDKs are either inactive, partially active, active or more active than the active non mutated form.

The expression "more active than the active non mutated form" means that the helicase activity of the mutated form represents at least 110%, particularly at least 150% and more particularly at least 200% of the helicase activity of the active non mutated form, and/or that the ATPase activity of the mutated form represents at least 110%, particularly at least 150% and more particularly at least 200% of the ATPase activity of the active non mutated form.

According to the invention, the mutated forms of MCM9 are tested as described above for their helicase and ATPase activity.

The invention further relates to a peptide or polypeptide derived from one of the following sequences: SEQ ID NO 2 (amino-acids 1-1143 of hMCM9), SEQ ID NO 4 (amino-acids 385-1143 of hMCM9), SEQ ID NO 6 (amino-acids 1-384 of hMCM9), SEQ ID NO 8 (amino-acids 1-1290 of MmMCM9), SEQ ID NO 10 (amino-acids 540-1290 of MmMCM9), SEQ ID NO 12 (amino-acids 1-539 of MmMCM9), SEQ ID NO 14 (amino-acids 1-1143 of XMCM9), SEQ ID NO 16 (amino-acids 385-1143 of XMCM9), SEQ ID NO 18 (amino-acids 1-384 of XMCM9),
by at least one mutation located on a position which is essential for the helicase and/or ATPase activity of MCM9 protein, in particular said mutations being chosen among the followings:
modification of the conserved lysine (K) in the Walker A motif GxxGxGK to alanine (A) or threonine (T) or other non polar or polar neutral amino acids,
modification of the conserved aspartic acid (D) in the Walker B motif DExx to alanine (A) or threonine (T) or other non polar or polar neutral amino acids.

The expression "position which is essential for the helicase and/or ATPase activity of MCM9 protein" particularly refers to Walker A and Walker B motifs.

According to the present invention, some mutated forms of the MCM9 protein may lose their helicase function or have an attenuated helicase activity and thus may be used to decrease the proliferation of cells, in particular of cancer cells.

The above modifications of the conserved lysine in the Walker A and/or the conserved aspartic acid in the Walker B lead to mutated forms of the MCM9 which have a highly decreased helicase activity (less than 80% of the helicase activity of the wild-type MCM9 protein), or no helicase activity.

The mutated forms of MCM9 which have a highly decreased helicase activity (less than 80% of the helicase activity of the wild-type MCM9 protein) or no helicase activity may be used in excess by comparison to the native active protein, to decrease the rate of cell proliferation.

The present invention further relates to a peptide or polypeptide containing 65 to 160 amino-acids and comprising a fragment which is essential for the helicase function of the MCM9 protein, said fragment containing in particular
sequence SEQ ID NO 20 (amino-acids 300-450 of SEQ ID NO 2) or sequence SEQ ID NO 22 (amino-acids 310-430 of SEQ ID NO 2) or sequence SEQ ID NO 24 (amino-acids 352-417 of SEQ ID NO 2) (helicase region of hMCM9)
or sequence SEQ ID NO 26 (amino-acids 460-610 of SEQ ID NO 8) or sequence SEQ ID NO 28 (amino-acids 470-590 of SEQ ID NO 8) or sequence SEQ ID NO 30 (amino-acids 508-573 of SEQ ID NO 8) (helicase region of MmMCM9)
or sequence SEQ ID NO 32 (amino-acids 300-450 of SEQ ID NO 14) or sequence SEQ ID NO 34 (amino-acids 310-430 of SEQ ID NO 14) or sequence SEQ ID NO 36 (amino-acids 353-418 of SEQ ID NO 14) (helicase region of XMCM9)
or sequence SEQ ID NO 38 (amino-acids 352-359 of SEQ ID NO 2) (walker A motif of hMCM9)
or sequence SEQ ID NO 40 (amino-acids 414-417 of SEQ ID NO 2) (walker B motif of hMCM9)
or sequence SEQ ID NO 42 (amino-acids 508-515 of SEQ ID NO 8) (walker A motif of MmMCM9)
or sequence SEQ ID NO 44 (amino-acids 570-573 of SEQ ID NO 8) (walker B motif of MmMCM9)
or sequence SEQ ID NO 46 (amino-acids 353-360 of SEQ ID NO 14) (walker A motif of XMCM9)
or sequence SEQ ID NO 48 (amino-acids 415-418 of SEQ ID NO 14) (walker B motif of XMCM9),
or any fragment derived therefrom by insertion, deletion, substitution of one or more amino acid or sharing at least 50%, in particular at least 65%, in particular at least 80% identity therewith, provided that the resulting fragment substantially retains at least part of the helicase and/or ATPase activity of the MCM9 protein.

The expression "fragment which is essential for the helicase function of MCM9 protein" refers to a fragment that particularly comprises or consists of the Walker A motif and/or the Walker B motif.

Walker A motif is involved in ATP binding. This motif forms a Glycin-rich flexible loop preceded by a β-strand and followed by an α-helix. The Walker A motif of *Xenopus* and mammalian MCM9 homologs (Gozuacik et al., 2003; Johnson et al., 2003) is a canonical consensus sequence (GxxGxGKS/T).

Walker B motif is involved in ATP hydrolysis and has the following structure: hybrophobic stretch followed by the amino acids signature D[ED], where the presence of at least one negatively charged amino acid in this motif is crucial for its function.

The expression "helicase region" refers to a region of the MCM9 protein that possesses the helicase activity, particularly by comprising the Walker A motif and/or the Walker B motif.

The invention also relates to a nucleic acid encoding the peptides or polypeptides as defined above.

The term "nucleic acid" refers to DNA or RNA.

The invention relates to single stranded or double stranded nucleic acids.

The invention further relates to a nucleic acid of one of the following sequences: SEQ ID NO 1 (nucleotides 1-4798 of hMCM9), SEQ ID NO 3 (nucleotides 1153-4798 of hMCM9), SEQ ID NO 5 (nucleotides 1-1152 of hMCM9), SEQ ID NO 7 (nucleotides 1-3873 of MmMCM9), SEQ ID NO 9 (nucleotides 1618-3873 of MmMCM9), SEQ ID NO 11 (nucleotides 1-1617 of MmMCM9), SEQ ID NO 13 (nucleotides 1-3432 of XMCM9), SEQ ID NO 15 (nucleotides 1153-3432 of XMCM9), SEQ ID NO 17 (nucleotides 1-1152 of XMCM9), or derived from one of the above-defined sequences by insertion, deletion, substitution of one or more nucleotide, or flanked by additional nucleotides at the 5' end or 3' end or at both ends, provided that the resulting sequence shares at least 40%, in particular at least 60%, in particular at least 80% identity with one of the above-defined sequences and provided that the resulting sequence encodes a peptide or polypeptide which has substantially the same helicase and/or ATPase activity as the MCM9 protein, and in particular provided that the resulting sequence has a maximum length of 1980 nucleotides and a minimum length of 900 nucleotides, or corresponding to a fragment thereof, provided that said fragment encodes a peptide or polypeptide which has substantially the same helicase and/or ATPase activity as the MCM9 protein.

The nucleotide sequence represented by SEQ ID NO 1 (nucleotides 1-4798) encodes the human MCM9 helicase represented by SEQ ID NO 1.

The nucleotide sequence represented by SEQ ID NO 3 corresponds to the nucleotides 1153-4798 of the human MCM9 sequence represented by SEQ ID NO 1 and encodes the polypeptide of sequence SEQ ID NO 4.

The nucleotide sequence represented by SEQ ID NO 5 corresponds to the nucleotides 1-1152 of the human MCM9 sequence represented by SEQ ID NO 1 and encodes the polypeptide of sequence SEQ ID NO 6.

The nucleotide sequence represented by SEQ ID NO 7 (nucleotides 1-3873) encodes the murine MCM9 helicase represented by SEQ ID NO 8.

The nucleotide sequence represented by SEQ ID NO 9 corresponds to the nucleotides 1618-3873 of the murine MCM9 sequence represented by SEQ ID NO 7 and encodes the polypeptide of sequence SEQ ID NO 10.

The nucleotide sequence represented by SEQ ID NO 11 corresponds to the nucleotides 1-1617 of the murine MCM9 sequence represented by SEQ ID NO 7 and encodes the polypeptide of sequence SEQ ID NO 12.

The nucleotide sequence represented by SEQ ID NO 13 (nucleotides 1-3432) encodes the *Xenopus* MCM9 helicase represented by SEQ ID NO 14.

The nucleotide sequence represented by SEQ ID NO 15 corresponds to the nucleotides 1153-3432 of the *Xenopus* MCM9 sequence represented by SEQ ID NO 13 and encodes the polypeptide of sequence SEQ ID NO 16.

The nucleotide sequence represented by SEQ ID NO 17 corresponds to the nucleotides 1-1152 of the *Xenopus* MCM9 sequence represented by SEQ ID NO 13 and encodes the polypeptide of sequence SEQ ID NO 18.

The expression "nucleic acid derived from one of the above-defined sequences" means that said nucleic acid contains at least one mutation chosen among insertion (or addition) or deletion or substitution of one or more nucleotide, and/or that the nucleic acid is flanked by additional nucleotides at the 5' end or at the 3' end or at both ends.

The mutation by deletion or by addition in the nucleic acid can eventually induce a shift in the opening reading frame of the MCM9 nucleotide sequence, in a way that the peptide or polypeptide encoded by said nucleic acid has substantially the same function as the MCM9 protein.

The mutation by substitution in the nucleotide sequence can lead to a silencing substitution due to the degeneracy of the genetic code, or to a substitution by a conservative amino-acid or a non conservative amino-acid in the peptide or polypeptide encoded by said nucleotide acid.

The additional nucleotides can particularly be chosen among nucleotides that encode Walker A, Walker B and Zn-finger motifs.

The expression "the resulting sequence has a maximum length of 1980 nucleotides and a minimum length of 900 nucleotides" particularly refers to nucleotide sequences encoding peptides or polypeptides that are within the highly conserved MCM2-8-like N-terminus part of MCM9 protein and that comprise the MCM-2-8 family domain.

The invention also relates to a nucleic acid derived from one of the following sequences: SEQ ID NO 1 (nucleotides 1-4798 of hMCM9), SEQ ID NO 3 (nucleotides 1153-4798 of hMCM9), SEQ ID NO 5 (nucleotides 1-1152 of hMCM9), SEQ ID NO 7 (nucleotides 1-3873 of MmMCM9), SEQ ID NO 9 (nucleotides 1618-3873 of MmMCM9), SEQ ID NO 11 (nucleotides 1-1617 of MmMCM9), SEQ ID NO 13 (nucleotides 1-3432 of XMCM9), SEQ ID NO 15 (nucleotides 1153-3432 of XMCM9), SEQ ID NO 17 (nucleotides 1-1152 of XMCM9), by at least one mutation, the resulting sequence encoding a peptide or a polypeptide having at least a mutation located on a site of phosphorylation by CDKs, in particular chosen among the followings:

modification of the conserved threonine (T) in the TP motif to alanine (A) or an equivalent amino acid and modification of the conserved serine (S) in the SP motif to alanine (A) or an equivalent amino acid, modification of the conserved threonine (T) in the TP motif to glutamate (E) or an equivalent amino acid and modification of the conserved serine (S) in the SP motif to glutamate (E) or an equivalent amino acid.

The invention further relates to a nucleic acid derived from one of the following sequences: SEQ ID NO 1 (nucleotides 1-4798 of hMCM9), SEQ ID NO 3 (nucleotides 1153-4798 of hMCM9), SEQ ID NO 5 (nucleotides 1-1152 of hMCM9), SEQ ID NO 7 (nucleotides 1-3873 of MmMCM9), SEQ ID NO 9 (nucleotides 1618-3873 of MmMCM9), SEQ ID NO 11 (nucleotides 1-1617 of MmMCM9), SEQ ID NO 13 (nucleotides 1-3432 of XMCM9), SEQ ID NO 15 (nucleotides 1153-3432 of XMCM9), SEQ ID NO 17 (nucleotides 1-1152 of XMCM9), by at least one mutation, the resulting sequence encoding a peptide or a polypeptide having at least a mutation located on a position which is essential for the helicase and/or ATPase activity of MCM9 protein, in particular said mutations being chosen among the followings:

modification of the conserved lysine (K) in the Walker A motif GxxGxGK to alanine (A) or threonine (T) or other non polar or polar neutral amino acids, modification of the conserved aspartic acid (D) in the Walker B motif DExx to alanine (A) or threonine (T) or other non polar or polar neutral amino acids.

The invention further relates to a nucleic acid which contains 180 to 480 nucleotides and which comprises a fragment which encodes a part of the MCM9 protein which is essential for its helicase function, said fragment containing in particular sequence SEQ ID NO 19 (nucleotides 898-1350 of SEQ ID NO 1) or sequence SEQ ID NO 21 (nucleotides 928-1290 of SEQ ID NO 1) or sequence SEQ ID NO 23 (nucleotides 1054-1251 of SEQ ID NO 1) (helicase region of hMCM9)

or sequence SEQ ID NO 25 (nucleotides 1387-1830 of SEQ ID NO 7)or sequence SEQ ID NO 27 (nucleotides 1408-1770 of SEQ ID NO 7) or sequence SEQ ID NO 29 (nucleotides 1522-1719 of SEQ ID NO 7) (helicase region of MmMCM9)

or sequence SEQ ID NO 31 (nucleotides 898-1350 of SEQ ID NO 13) or sequence SEQ ID NO 33 (nucleotides 928-1290 of SEQ ID NO 13) or sequence SEQ ID NO 35 (nucleotides 1057-1254 of SEQ ID NO 13) (helicase region of XMCM9)

or sequence SEQ ID NO 37 (nucleotides 1054-1077 of SEQ ID NO 1) (walker A motif of hMCM9)

or sequence SEQ ID NO 39 (nucleotides 1240-1251 of SEQ ID NO 1) (walker B motif of hMCM9)

or sequence SEQ ID NO 41 (nucleotides 1522-1545 of SEQ ID NO 7) (walker A motif of MmMCM9)

or sequence SEQ ID NO 43 (nucleotides 1708-1719 of SEQ ID NO 7) (walker B motif of MmMCM9)

or sequence SEQ ID NO 45 (nucleotides 1057-1080 of SEQ ID NO 13) (walker A motif of XMCM9)

or sequence SEQ ID NO 47 (nucleotides 1243-1254 of SEQ ID NO 13) (walker B motif of XMCM9)

or any fragment derived therefrom by insertion, deletion, substitution of one or more nucleotide or sharing at least 45%, in particular at least 60%, in particular at least 80% identity therewith, provided that the resulting fragment encodes a peptide or polypeptide which substantially retains at least part of the helicase and/or ATPase activity of the MCM9 protein.

The invention relates to a nucleic acid which is complementary to a nucleic acid as defined above.

The term "complementary" means that said nucleic acid is able to pair or hybridize to a nucleic acid by Watson and Crick or other base-pair interactions, thus being able to form a double-stranded structure with this nucleic acid.

The invention also relates to a nucleic acid which is capable of hybridizing with a nucleic acid as defined above under appropriate hybridizing conditions.

The "appropriate hybridizing conditions" may be determined according to "Molecular cloning", third edition, Sambrook and Russel, CSHL press, 2001.

The invention described herein also relates to an expression vector comprising a nucleic acid as described above and the elements which are necessary for its expression in a cell.

The expression "elements which are necessary for its expression" particularly refers to regulatory sequences to which the nuclei acid is operably linked.

The term "operably linked" means that the nucleotide sequence is linked to a regulatory sequence in a manner which allows the expression of the nucleic acid sequence. The regulatory sequences are well known by the man skilled in the art. They include promoters, enhancers and other expression control elements.

The invention also provides a cell transformed by a nucleic acid as defined above or by an expression vector as defined above.

The host cell according to the present invention includes prokaryotic host cells (bacterial cells), such as E. coli, Streptomyces, Pseudomonas, Serratia marcescens and salmonella typhimurium or eukaryotic cells such as insect cells, in particular baculovirus-infected Sft9 cells, or fungal cells, such as yeast cells, or plant cells or mammalian cells.

The invention further relates to a recombinant protein obtained by the expression of the expression vector as defined above.

The DNA vector containing the MCM9 gene or fragments thereof as defined above is used to produce a recombinant form of the protein by recombinant technology. Recombinant technology comprises the steps of ligating the nucleotide sequence into a gene construct such as an expression vector and transforming or transfecting said gene construct into host cells. The host cells that express the protein are then lysed and the recombinant protein is isolated and purified, for example by chromatography.

The present invention relates to an antibody or antigen-binding fragment which binds to an MCM9 protein or part of an MCM9 protein or to a modified active MCM9 protein, in particular to a peptide or polypeptide as defined above and in particular to the polypeptide represented by SEQ ID NO 2 or SEQ ID NO 4 (corresponding to amino-acids 1-1143 or 385-1143 of hMCM9).

The antibody can be polyclonal or monoclonal and the term "antibody" is intended to encompass both polyclonal and monoclonal antibodies. The terms "polyclonal" and "monoclonal" refer to the degree of homogeneity of an antibody preparation, and are not intended to be limited to a particular method of production.

The present invention relates to antibodies which bind to MCM9 protein or part of an MCM9 protein, or to a mutated form of the MCM9 protein or part thereof. A mammal, such as a rabbit, a mouse or a hamster, can be immunized with an immunogenic form of the protein, such as the entire protein or a part of it. The protein or part of it can be administered in the presence of an adjuvant.

The term "immunogenic" refers to the ability of a molecule to elicit an antibody response. Techniques for conferring immunogenicity to a protein or part of it which is not itself immunogenic include conjugation to carriers or other techniques well known in the art.

The immunization process can be monitored by detection of antibody titers in plasma or serum. Standard immunoassays, such as ELISA can be used with the immunogenic protein or peptide as antigen to assess the levels of antibody.

The invention relates in particular to a monoclonal or polyclonal antibody directed against an MCM9 protein or against a peptide or polypeptide comprising part of an MCM9 protein, and in particular against a peptide or polypeptide as defined above.

The invention also relates to a method for the in vitro or ex vivo production of catalytically active MCM9 helicase in foreign expression systems, such as bacteria (E. coli) or insect cells (Sf9), or equivalent or in vitro systems for coupled transcription/translation of the MCM9 cDNA, such as rabbit reticulocytes systems or lysate of E. coli cells or translation of the MCM9 mRNA into xenopus oocyte or egg extracts, possibly under form of a tagged recombinant protein, comprising the steps of:

lysis of cells expressing MCM9 proteins in the following buffer or equivalent, 20 mM TrisHCl pH 8.5, 100 mM KCl, 5 mM β-mercaptoethanol, 5-10 mM imidazole, 10% glycerol (v/v) proteases inhibitors;

purification of the soluble MCM9 proteins by nickel affinity chromatography technology or equivalent or similar affinity chromatography technology;

elution of bound proteins in 10 mM TrisHCl pH 8.5; 100 mM KCl; 5 mM β-mercaptoethanol; 100-250 mM imidazole, 10% glycerol (v/v) proteases inhibitors;

supplementation of purified MCM9 proteins, with or without cleaved tag, with 0.1 mg/ml of BSA;

desaltation on a Bio-spin P30 column (Biorad) equilibrated with 20 mM TrisHCl pH 7.4, 150 mM NaCl, 0.5 mM EDTA, 1 mM DTT, 0.01% Triton X-100 for helicase and ATPase activities, or in XB (100 mM KCl, 0.1 mM $CaCl_2$, 2 mM $MgCl_2$, 10 mM Hepes-KOH, 50 mM sucrose, pH 7.7) for egg extracts reconstitution experiments; and supplementation of the protein with 25% glycerol and storage at −20° C. mercaptoethanol; The rabbit reticulocytes systems and lysate of *E. coli* cells are ex vivo cell free extracts that can transcribe a given cDNA into mRNA and translate the mRNA into a protein. Such a system may be valuable to produce catalytically active protein to perform in vitro activity assays.

The recombinant proteins are tagged either at the N- or C-terminal with well-known sequence Tag, such as Hist-Tag, Myc-Tag, Flag-Tag, Tap-Tag, GST-tag, MAL-Tag, in order to facilitate the purification of the protein. Preferentially, the sequence tag can be removed by an enzymatic or chemical reaction involving the use of thrombin and/or TEV protease or similar enzymatic activities.

The expression "catalytically active" means that the corresponding recombinant protein can bind and hydrolyze continuously ATP resulting in helicase activity, such as displacement of an oligonucleotide annealed to single stranded DNA, or able to melt double stranded DNA in vitro, and/or that the protein can catalyze formation of pre-replication complexes in vitro and /or in vivo, determined by the ability of MCM2-7 proteins to associate with chromatin in vivo and /or in vitro.

According to another embodiment, the invention relates to a pharmaceutical composition comprising as active substance a peptide or polypeptide or a nucleic acid or an expression vector or a cell or an antibody or antigen-binding or a monoclonal or polyclonal antibody, as defined above, in association with a pharmaceutically acceptable vehicle.

The pharmaceutical preparation of the present invention can be formulated with a physiologically acceptable medium, such as water, buffered saline, polyols (glycerol, propylene glycol, liquid polyethylene glycol) or dextrose solutions. Preferentially, the pharmaceutical preparation is formulated in a vector which will allow the delivery of said preparation inside the target cells. The pharmaceutical preparation can be administered by intradermal, intramuscular, intraperitoneal, intravenous, subcutaneous or oral way.

The pharmaceutical preparation may also be administered as part of a combinatorial therapy with other agents, such as inhibitors or activators of cell proliferation. Inhibitors of cell proliferation can be chosen among aphidicoline, cis-platinum, etoposides, lovastatin, mimosine, nocodazole. Activators of cell proliferation can be chosen among growth factors such as EGF (Epidermal Growth Factor), FGF (Fibroblast Growth Factor), NGF (Nerve Growth Factor) and analogues, and lipopolysaccharides.

The invention relates to a method for the screening of drugs useful in the treatment of human or animal pathology linked to a dysfunction of the expression of the MCM9 gene, said method comprising contacting of the potential drugs with cells such as cancer cells or transformed cells and especially liver, brain, muscle, skin or gut cells wherein a decrease of the expression of the MCM9 helicase is induced by transformation of said cells with recombinant and/or mutated forms of the MCM9 gene which is in particular represented by one of the following sequences: SEQ ID NO 1, SEQ ID NO 3, SEQ ID NO 5, SEQ ID NO 7, SEQ ID NO 9, SEQ ID NO 11, SEQ ID NO 13, SEQ ID NO 15, SEQ ID NO 17, or of parts of said gene, or of transcripts thereof, or of antisense nucleic acids able to hybridize with part of said gene or transcripts, or of silencing RNA derived from parts of said transcripts and able to repress said MCM9 gene, and screening the drugs able to inhibit the proliferation of said transformed cells.

According to another embodiment, the present invention relates to a method for the in vitro or ex vivo screening of drugs useful in the treatment of human or animal pathology linked to a dysfunction of the expression of the MCM9 gene, said method comprising contacting of the potential drugs with cells such as:
cancer cells or
cells wherein recombinant and/or mutated active forms of MCM9 helicase, which is in particular represented by one of the following sequences: SEQ ID NO 2, SEQ ID NO 4, SEQ ID NO 6, SEQ ID NO 8, SEQ ID NO 10, SEQ ID NO 12, SEQ ID NO 14, SEQ ID NO 16, SEQ ID NO 18, or fragments thereof, are introduced to increase the helicase activity in said cells or
transformed cells and especially liver, brain, muscle, skin or gut cells wherein an increase of the expression of an active form of MCM9 helicase is induced by transformation of said cells with recombinant and/or mutated forms of the MCM9 gene which is in particular represented by one of the following sequences: SEQ ID NO 1, SEQ ID NO 3, SEQ ID NO 5, SEQ ID NO 7, SEQ ID NO 9, SEQ ID NO 11, SEQ ID NO 13, SEQ ID NO 15, SEQ ID NO 17, or of parts of said gene, or of transcripts thereof,
and screening the drugs able to inhibit the proliferation of said cells.

The expression "to increase the helicase activity" means that the helicase activity is increased from 10% to 90%, in particular from 50% to 90%, by comparison with the basal helicase activity of wild-type MCM9 protein.

The expression "basal helicase activity" refers to the helicase activity in cells cultured in usual conditions, particularly according to the manufacturer protocol.

The expression "increase of the expression of an active form of MCM9 helicase" means that the number of active helicase is increased, thus increasing the helicase activity as defined above.

In the above embodiment, the term "drugs" refers to inhibitors of DNA replication whose target is the DNA helicase. The inhibitors of DNA replication can be chosen among dibenzothiepin and its analogues, non-hydrolysable NTPs such as γATP, DNA-interacting ligands such as nogalamycin, daunorubicin, ethidium bromide, mitoxantrone, actinomycin, netropsin and cisplatin, 4,5,6,7-tetrabromo-1H-benzotriazole (TBBT), peptides binding DNA that inhibit the unwinding of the double helix by the helicase, bananins and its derivatives, the aminothiazolylphenyl-containing compounds BILS 179 BS and BILS 45 BS, 5'-O-(4-fluorosulphonylbenzoyl)-esters of ribavirin (FSBR), adenosine (FSBA), guanosine (FSBG) and inosine (FSBI), CDKs inhibitors such as staurosporines and its derivatives.

In order to screen potential drugs inhibiting cell proliferation, proliferation tests are carried out on the proliferative cells.

According to another embodiment, the present invention relates to a method for the in vitro or ex vivo screening of drugs useful in the treatment of human or animal pathology linked to a dysfunction of the expression of the MCM9 gene, said method comprising contacting of the potential drugs with:
cells wherein recombinant and/or mutated inactive forms of MCM9 helicase are introduced to decrease the helicase activity in said cells or
transformed cells and especially liver, brain, muscle, skin or gut cells wherein an increase of the expression of an inactive MCM9 helicase is induced by transformation of said cells with recombinant and/or mutated forms of the MCM9 gene which is in particular represented by one of the following sequences: SEQ ID NO 1, SEQ ID NO 3, SEQ ID NO 5, SEQ ID NO 7, SEQ ID NO 9, SEQ ID NO 11, SEQ ID NO 13, SEQ ID NO 15, SEQ ID NO 17, or of parts of said gene, or of transcripts thereof, or, transformed cells and especially liver, brain, muscle, skin or gut cells wherein a decrease of the expression of an active form of MCM9 helicase is induced by transformation of said cells with antisense nucleic acids able to hybridize with part of said gene or transcripts, or of silencing RNA derived from parts of said transcripts and able to repress said MCM9 gene, or cells wherein antibodies directed against MCM9 protein, which is in particular represented by one of the following sequences: SEQ ID NO 2, SEQ ID NO 4, SEQ ID NO 6, SEQ ID NO 8, SEQ ID NO 10, SEQ ID NO 12, SEQ ID NO 14, SEQ ID NO 16, SEQ ID NO 18, or fragments thereof, are introduced to decrease the helicase activity in said cells, and screening the drugs able to stimulate the proliferation of said cells.

The expression "to decrease the helicase activity" means that the helicase activity is decreased from 10% to 90%, particularly from 30% to 90%, more particularly from 60% to 90%, by comparison with the basal helicase activity of wild-type MCM9 protein.

The expression "decrease of the expression of an active form of MCM9 helicase" means that the number of active helicase is decreased, thus decreasing the helicase activity as defined above.

In the above embodiment, the term "drugs" refers to activators of DNA replication whose target is the DNA helicase. The activators of DNA replication can be chosen among caffeine, tamoxifen in uterine tissues, leptomycin B, CDKs inhibitors such as staurosporines.

In order to screen potential drugs stimulating cell proliferation, proliferation tests are carried out on the non proliferative cells.

The invention also relates to the use of an agonist or antagonist of an MCM9 helicase and in particular of the polypeptide represented by SEQ ID NO 2 or SEQ ID NO 4 or SEQ ID NO 6 or SEQ ID NO 8 or SEQ ID NO 10 or SEQ ID NO 12 or SEQ ID NO 14 or SEQ ID NO 16 or SEQ ID NO 18, for inhibiting cell proliferation or allowing to increase replication of the DNA, particularly in vitro or ex vivo, wherein the agonist or antagonist enters the cell, said antagonist causing the inhibition of DNA replication and said agonist contributing to the restoration of cell proliferation or to the ability of the cell to replicate DNA in unfavorable conditions.

The expression "restoration of cell proliferation" means that the proliferation of the cells, for example blocked by the action of an antagonist, can be re-established, so that cells can replicate the DNA and divide.

The expression "unfavorable conditions" refers to conditions wherein cells are not competent to proliferate, because they are in a state of quiescence, such as differentiated cells, or because the proliferation of said cells has been temporarily blocked by an inhibitor of cell proliferation, such as mimosine, lovastatine, aphidicolin, hydroxyurea, or DNA damaging agents and/or alkylating agents.

The invention particularly relates to antagonists of MCM9 that block the binding of MCM9 on cdt1 and/or on the chromatin.

The invention further relates to a method for inhibiting cell proliferation or allowing a better replication of the DNA, comprising administering an agonist or antagonist of an MCM9 helicase and in particular of the polypeptide represented by SEQ ID NO 2 or SEQ ID NO 4 or SEQ ID NO 6 or SEQ ID NO 8 or SEQ ID NO 10 or SEQ ID NO 12 or SEQ ID NO 14 or SEQ ID NO 16 or SEQ ID NO 18 in a way that the agonist or antagonist enters the cell, said antagonist causing the inhibition of DNA replication and said agonist contributing to the restoration of cell replication or to the ability of the cell to replicate DNA in unfavorable conditions.

The invention also relates to a method for inhibiting cell proliferation or allowing a better replication of the DNA in vitro or ex vivo, comprising administering an agonist or antagonist of an MCM9 helicase and in particular of the polypeptide represented by SEQ ID NO 2 or SEQ ID NO 4 or SEQ ID NO 6 or SEQ ID NO 8 or SEQ ID NO 10 or SEQ ID NO 12 or SEQ ID NO 14 or SEQ ID NO 16 or SEQ ID NO 18 in a way that the agonist or antagonist enters the cell, said antagonist causing the inhibition of DNA replication and said agonist contributing to the restoration of cell replication or to the ability of the cell to replicate DNA in unfavorable conditions.

The invention also relates to a method for diagnosing, in particular in vitro or ex vivo, a pathology or a risk of developing a pathology linked to a disorder in the expression of the MCM9 protein, consisting in assessing a possible surexpression of MCM9 or a possible alteration of the normal activity of MCM9 and/or a possible mutation on a MCM9 gene and/or a possible mutation on a MCM9 protein in particular resulting in a possible genomic instability and/or a possible neoplastic transformation.

The expression "genomic instability" refers to the loss and/or alteration of the genetic material during cell proliferation and division.

The surexpression of MCM9 is assessed by measuring the level of expression of the MCM9 gene by Northern blot and/or RT-PCR in vivo and/or in vitro, or by in situ hybridization of cells with DNA and/or RNA probes, as well as by determining the amount of MCM9 protein produced in the cell by western blot and/or by in situ hybridization with MCM9-specific antibody (immunofluorescence). The levels of expression of the MCM9 gene and/or of the corresponding protein in cells surexpressing MCM9 are compared to the levels of non-pathologic cells isolated from the same patient.

The alteration of the normal activity of MCM9 is assessed by determining the DNA helicase activity of the MCM9 protein in vitro and/or in vivo, and/or by assessing the ability of MCM9 to catalyze the formation of pre-replication complexes onto chromatin in vivo and/or in vitro. This latter can be determined by detection of components of the pre-replication complex, such as the MCM2-7 proteins, and/or that of the PCNA protein, onto chromatin by western blot and/or immunofluorescence in vivo and/or in vitro.

The mutation on a MCM9 gene is assessed by extraction and isolation of the DNA from the cells and determination of the DNA sequence of the MCM9 gene, and/or by isolation of the total mRNAs from the cells and amplification of the MCM9 gene by RT-PCR, and/or by analysis of the polymorphysm of the MCM9 gene by restriction digest (RFLP).

The mutation on a MCM9 protein in particular resulting in a possible genomic instability is assessed by comparison of the sequence of the MCM9 gene isolated from pathologic cells with that isolated from non-pathologic cells obtained from the same patient. Mutations in the DNA sequence coding for the known motifs of the MCM9 protein, such as the Zn-finger domain and/or the MCM2-8 signature domain and/or the helicase domain are potential candidates for mutations causing genomic instability.

The neoplastic transformation is assessed by the ability of cells to proliferate indefinitely in vitro and/or the ability of said cells to induce tumors when injected into animals.

The invention also relates to a method for the screening of biologically active agents useful in the treatment of human or animal pathology linked to a dysfunction of the expression of the MCM9 gene, said method comprising:

administering a potential agent to a non-human transgenic animal model for MCM9 gene function, particularly chosen among a MCM9 knock-out model and a model of exogenous and stably transmitted MCM9 sequence, and determining the effect of said agent on the development of the transgenic animal and/or the development of diseases such as those defined above, and in particular the development of cancer.

The term "non-human animal" includes all mammals expect for humans, advantageously rodents and in particular mice.

The term "transgenic animal" denotes an animal into whose genome has been introduced an exogenous gene construct, which has been inserted either randomly into a chromosome, or very specifically at the locus of an endogenous gene.

In a MCM9 knock-out model, the exogenous gene construct has been inserted at the locus of the MCM9 gene, resulting in the impossibility of expressing this MCM9 gene, since it is either interrupted or entirely or partially replaced by a construct such that it no longer allows expression of the endogenous gene, or alternatively a construct which, in addition to the deletion of the endogenous gene, introduces an exogenous gene. Such animals will be referred to as "knock-out" animals or animals in which the abovementioned endogenous gene is invalidated.

A model of exogenous and stably transmitted MCM9 sequence can be obtained by transfection of the cells of the animal (such as stem cells or in vitro cultured cell lines) with a DNA plasmid bearing wild-type or mutated forms of the MCM9 gene under control of promoter sequence of the MCM9 gene or promoters for standard reporter genes which are constitutively expressed or whose expression can be controlled by induction with inducers of the expression of the above mentioned promoters, integration of such plasmid in the chromosome of such cells so that this transgene is stably transmitted to the cell progeny.

The effect of the agent is determined by morphological and/or phenotypical analysis of the transgenic animal, and/or by molecular analysis by measure of cell proliferation and/or cell death and/or cell differentiation and/or cell apoptosis, and/or determination of the karyotype of the animal, that is to say analysis of the number and structure of the chromosomes of cells chosen from the whole embryo or tissues of the animal.

The MCM9 protein is a novel member of the MCM2-8 protein family with an unique C-terminal domain.

Figure 1A:
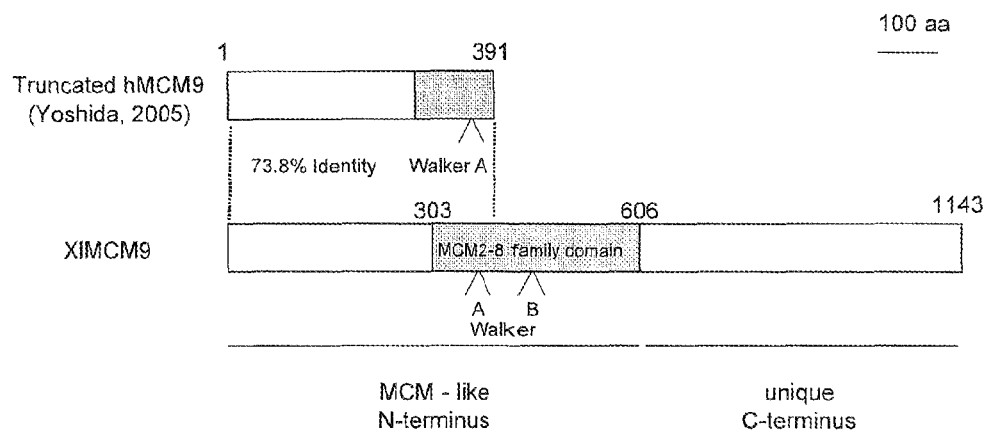
FIG. 1A and FIG. 1B

FIG. 1A: Alignment of the previously reported truncated human MCM9 protein truncated hMCM9 (Yoshida, 2005) with the Xenopus MCM9 protein (XlMCM9). The MCM2-8 signature domain is shown in grey. The ATP binding (Walker A) and hydrolysis (Walker B) motifs are indicated. Numbers indicate aminoacids.

Figure 1B:
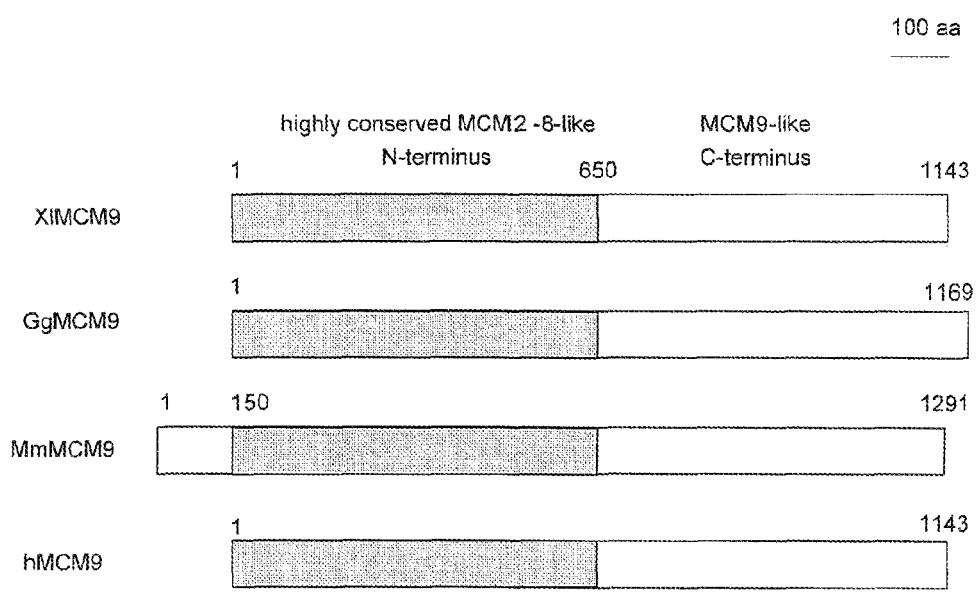

FIG. 1B: Alignment between full length MCM9 homologs in different organisms: Xenopus (XlMCM9), chicken (GgMCM9), mouse (MmMCM9) and human (hMCM9) proteins. Numbers indicate aminoacids.

FIG. 2A, FIG. 2B and FIG. 2C

Alignment of MCM9-like proteins in different organisms.

FIG. 2A: Alignment of the conserved N-terminal half of MCM9 proteins from Humans (SEQ ID NO: 49), Mouse (SEQ ID NO: 50), Chicken (SEQ ID NO: 51) and Xenopus (SEQ ID NO: 52), obtained by ClustalW. The Walker A and B motifs are underlined. Stars indicate identity, while similar amino acids are indicated by a single or double dot. The number of points indicates the degree of similarity defined by the program ClustalW.

FIG. 2B: Alignment of MCM9 (SEQ ID NO: 60) with MCM2-8 proteins (MCM3 (SEQ ID NO: 53), MCM7 (SEQ ID NO: 54), MCM5 (SEQ ID NO: 55), MCM2 (SEQ ID NO: 56), MCM4 (SEQ ID NO: 57), MCM6 (SEQ ID NO: 58) and MCM8 (SEQ ID NO: 59)) from Xenopus within the central region of MCM2-8 proteins and the N-terminal of MCM9. Alignment was performed as in FIG. 2A. Walker A and B motifs are underlined. The alignment region corresponds to amino acids 449-673 for MCM2, 285-520 for MCM3, 446-673 for MCM4, 320-545 for MCM5, 335-563 for MCM6, 321-550 for MCM7, 336-650 for MCM8 and 291-550 for MCM9.

FIG. 2C: Holograms of human MCM2-7, MCM8 and MCM9. The Phylogram was calculated with ClustalW.

FIG. 2D: Alignment of the C-terminal regions of MCM9 from Xenopus (SEQ ID NO: 61), Chicken (SEQ ID NO: 62), Mouse (SEQ ID NO: 63) and Humans (SEQ ID NO: 64). Alignment was performed as in FIG. 2A. The alignment region corresponds to amino acids 650-1143 for Xenopus MCM9, 800-1291 for Mouse MCM9, 650-1169 for Chicken MCM9 and 650-1143 for Human MCM9.

FIG. 3

Characterization of the antibody raised against a peptide corresponding to amino acids 605 to 1143 of the Xenopus MCM9 protein.

Western Blot analysis of egg extract (1 µl and 2 µl) with pre-immune serum (lane 1 and 2) and serum against MCM9 (3IP1, lane 3 and 4).

FIG. 4

MCM9 associates with chromatin.

Western blot of chromatin fractions prepared after 40, 60 or 120 minutes after addition of sperm chromatin to egg extract. MCM9 and ORC2 proteins were detected with specific antibodies. The last lane (40+geminin) shows that MCM9 associates with chromatin also when replication is blocked by geminin, however to a lesser extent.

Figure 5A:
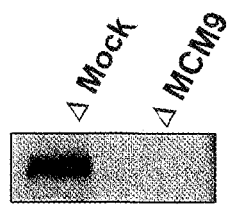
Figure 5B:
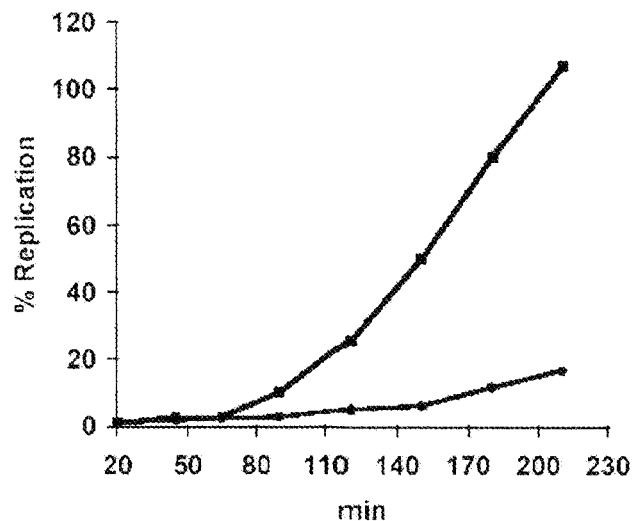

FIGS. 5A and 5B

Depletion (Δ) of MCM9 from egg extracts abolishes DNA replication.

FIG. 5A: Western blot of egg extract after incubation with non-specific antibody (Mock) or antibody against MCM9. The MCM9 protein can be completely removed from the egg extract as seen when depletion is carried out using an antibody against MCM9 (Δ MCM9).

FIG. 5B: Replication kinetics in Mock-depleted egg extract (squares) and MCM9-depleted egg extract (circles). Depletion of MCM9 abolishes DNA replication.

FIG. 6

Depletion of MCM9 from an egg extract does not (quantitatively) codeplete other proteins involved in DNA licensing/replication.

Egg extract after Mock-depletion (A Mock) or MCM9-depletion (Δ MCM9) was mixed with SDS-sample buffer, loaded on a SDS-PAGE and blotted. Following western blot analysis was performed for MCM9, as well as for proteins known to be involved in DNA licensing or replication (all MCM2-7, MCM8, Cdt1 and ORC2).

FIG. 7

Depletion of MCM9 from egg extract inhibits the loading of the MCM2-7 complex onto chromatin.

Figure 4:
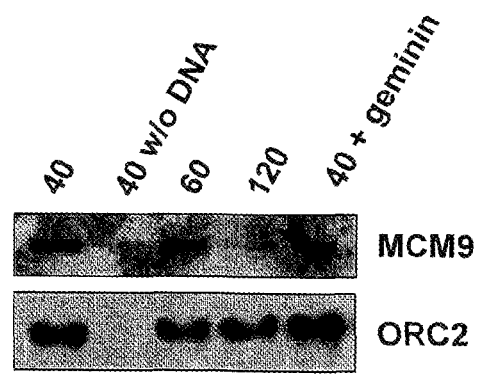

A western blot analysis of chromatin assembled either in a Mock-depleted (Δ Mock) or MCM9-depleted (Δ MCM9) egg extract, was carried out as described in FIG. 4. The presence of MCM2-7, Cdt1, CDC6 and ORC2 in the chromatin was detected using the corresponding antibodies.

Chromatin which was assembled in MCM9-depleted extract does not contain MCM2-7 proteins, less Cdt1, but more CDC6.

FIG. 8

Association of MCM9 with chromatin is dependent on ORC.

A western blot analysis of chromatin assembled either in a Mock-depleted (Δ Mock) or ORC2-depleted (Δ ORC2) egg extract was carried out as in FIG. 4. Chromatin which was assembled in an ORC2-depleted extract does not contain MCM9 and is also devoid of pre-RC proteins (MCM2-7, Cdt1, CDC6). Histon H3 (H3) is shown as a loading control and ORC2 as a depletion control.

FIG. 9

MCM9 interacts with Cdt1 in egg extract.

Western blot analysis of immunopurifications (IP) of MCM9, Cdt1, and a Mock-purification (done with an unspecific antibody), using an MCM9 antibody (upper lane) or a cdt1 antibody (lower lane). In the MCM9 purification, a substantial amount of Cdt1 is present, showing that these two proteins interact in egg extract.

FIG. 10

GST-TEV-MCM9 can be purified from Baculovirus-infected SF9 cells.

Coomasie stained SDS-PAGE showing GST-TEV-MCM9 recombinant protein bound to GSH-beads, after incubation of the GSH-beads with SF9 cell-lysate, and the GST-TEV-MCM9 protein after elution from the GSH-beads (eluate GSH).

Figure 11A:
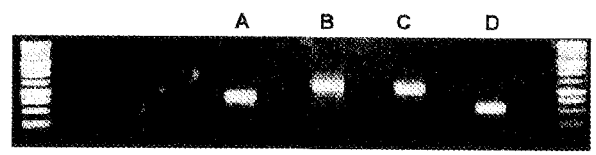
Figure 11B:
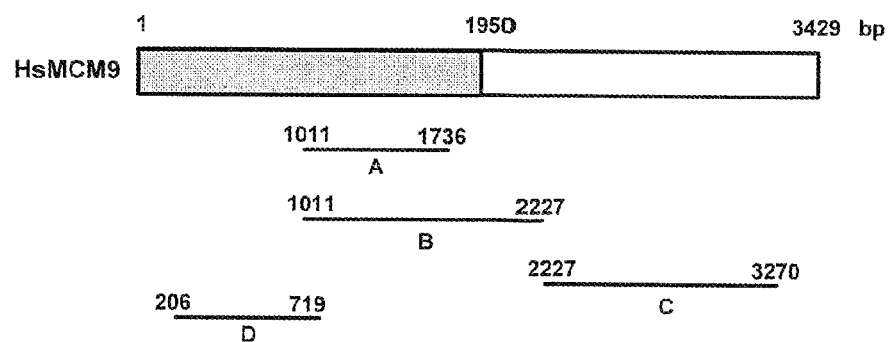

FIGS. 11A and 11B

RT-PCR analysis of human MCM9 RNA.

FIG. 11A: RT-PCR analysis of parts of human MCM9 (fragments A, B, C and D)

FIG. 11B: location of the fragments amplified by PCR in FIG. 11A on the human MCM9 cDNA.

EXAMPLES

Example 1

Identification of MCM9 Protein, a Specific Vertebrate Member of the MCM8 Protein Family Screening the public EST databases, the inventors have identified a homolog of the truncated human MCM9 protein in *Xenopus laevis*. Unlike the reported truncated human MCM9, the *Xenopus* MCM9 (XlMCM9) is much longer and contains all the features of MCM proteins, in particular the entire MCM2-7 signature domain, made of both ATP binding (Walker A) and hydrolysis (Walker B) motifs. In addition, *Xenopus* MCM9 is closer related to MCM8, since both possess the canonical Walker A and B motifs (whereas MCM2-7 possesses a deviant Walker A motif).

By careful screening the genome of other vertebrates and mammals in silico, the Inventors have now identified conserved homologs of the entire MCM9 protein also in chicken, mouse and human, whose primary structure closely resembles that of the *Xenopus* MCM9 protein. These findings indicate that the MCM9 protein is a canonical MCM protein also in humans, closer related to human MCM8 than to human MCM2-7 proteins, and that the previously reported truncated human MCM9 protein represents only a part of the entire human MCM9.

Experimental Procedures

Identification of MCM9 Homologs

To identify homologs of MCM9, database searches were performed using the program BLAST. Either EST databases or genomic databases for indicated organisms were searched. In addition, ab initio proteins were generated to identify hypothetical proteins by BLAST with the GNOMON routine. GNOMON uses multiple heuristics to find the best self-consistent set of transcripts and protein alignments in a certain genomic region. The program calculates splice sites and identifies the cases where two exons of the protein alignment are as closed as maximum 50 by having different frames. Since such short introns are extremely rare, in these cases GNOMON introduces frame shifts in the sequence to combine multiple exons, which allows to create consistent transcripts also from genomic regions containing errors in its sequence. Proteins predicted by GNOMON were then confirmed by identification of EST sequences in EST databases and by GEO Blast.

Special Search for Short Regions of High Homology

To identify smaller regions of homology and to identify EST sequences within a database, also MEGABLAST was used (Zhang et al., 2000) which is especially suited for the identification of shorter, but highly similar sequences in a given genome database. Megablast was designed to optimize the alignment of sequences which differ only slightly due to e.g. sequencing errors.

Protein Alignment

Protein alignments were performed using the program ALIGN (Pearson et al., 1997) or CLUSTALW (Higgins et al., 1994), available on the server of the Institute of Human Genetics (IGH), Montpellier or the EMBL-EBI server. Identification of protein domains and motif searches were performed either using InterProScan available on the EMBL-EBI server scanning the InterPro database of protein families, domains and functional sites (Mulder et al., 2005) or Motif-Scan, using the Hits-database from the Swiss Institute of Bioinformatics (SIB).

Results

Identification of a *Xenopus* Homolog of Reported Truncated Human MCM9

To identify a *Xenopus* homolog of the recently described truncated human MCM9 protein (Yoshida, 2005), the Inventors performed a search using the BLAST program with the truncated hMCM9 protein sequence as a query against the Expressed Sequences Tagged (EST) *Xenopus* database. Consequently, the Inventors identified the cDNA clone IMAGE6637819 (accession number BC070720 on GenBank), coding for a protein of 1143 amino acids derived from a mRNA expressed in *Xenopus* eggs. Sequence alignment with XlMCM proteins show that the first 835 aa of XlMCM9 share 25.6% identity with full length XlMCM8 (835 aa) while the identity with XlMCM2-7 proteins is in average 10.5%. These results strongly indicate that XlMCM9 is a distinct member of the MCM family in *Xenopus*. (FIG. 1A). XlMCM9 shows a strong identity (73.8%) in its first amino-terminal 391 aa with the reported truncated hMCM9.protein (391 aa, Yoshida, 2005). However, unlike the reported truncated hMCM9, the XlMCM9 protein contains a much longer carboxy-terminal extension which shows in its first part a high homology to the other MCM proteins. Within this region, XlMCM9 contains an intact MCM2-7 family signature domain (aa 303–aa 606) harboring Walker A and B motifs. The MCM2-7 family domain is the highest conserved region among the members of the MCM2-7 family.

Interestingly, the Walker A motif of XlMCM9 (GxxGxGKS, aa 354-360), is a canonical consensus site as the one found in MCM8 proteins, but different from that found in MCM2-7 proteins, which is a deviant consensus site (GxxGxAK/S). The Inventors conclude that this protein is the *Xenopus* homologue of truncated hMCM9. Importantly, the size of the XlMCM9 protein is bigger than that of other MCM proteins. This is essentially due to a C-terminal extension after the MCM homology region, which does not share a clear homology to other MCM proteins and seems to be a unique feature of this protein (FIG. 1A).

Identification of MCM9 Homologs in the Genome of Other Vertebrates and Mammals

Given that the length of XlMCM9 is much bigger than reported for the truncated hMCM9 (Yoshida, 2005), the Inventors investigated whether this was a special feature of the *Xenopus* protein or if a longer MCM9 homolog protein could be also identified in other organisms. Therefore, the Inventors performed databank searches using BLAST with the XlMCM9 protein sequence against databases of several organisms.

A record (XM_419764 on GenBank) in the chicken genomic database was found derived from an annotated sequence (NW_060336 on GenBank, located on chromosome 3 between 61.196 and 61.290 kbp). Within this region, GNOMON predicts a mRNA coding for a 1169 aa long protein, which could be supported by multiple EST evidences (e.g. BU378776, BU478046, BU271359, on GenBank). This chicken MCM9 (GgMCM9) shares 54.1% identity with XlMCM9. Like XlMCM9, the chicken protein consists of two main parts: an N-terminal part which is highly conserved (aa 1-626 share 81.2% identity with XlMCM9) and a C-terminal region which is much less conserved within MCM proteins as well as in respect to other MCM9 homologs (FIG. 2D).

Next, searching the mouse genome database, the Inventors found two entries (BAB31238.1 and NP_954598 on chromosome 10 between 53.544 and 53.679 kbp, on GenBank), both coding for unnamed protein products. The proteins corresponding to these sequences showed 87% identity with the N-terminus of GgMCM9, and 47.9% identity with the carboxy-terminus of GgMCM9, respectively. Searching the mouse EST database with these sequences, a number of partially overlapping expressed sequences were identified (e.g. BY720667, CB244669, CX2225903, on GenBank) and the entire corresponding protein was re-joined in silico, resulting in a 1291 aa long hypothetical protein possessing over 60% identity with the GgMCM9 protein and 47% to XlMCM9. MmMCM9 shares the general organization of a highly conserved N-terminus and a much less conserved C-terminus in respect to the other identified MCM9 proteins and other MCM family members (FIG. 1B). In addition, the first 150 aa of this protein are not present in the other MCM9 proteins. Importantly, its first 386 aa are 100% identical with the reported 386 aa containing mouse MCM9 (Yoshida, 2005).

These findings suggest that XlMCM9-like proteins can also be found in the genome of other vertebrates and mammals. Therefore, the Inventors re-investigated the human databases using the full XlMCM9 sequence as a query to search for a complete human MCM9 protein. First, homologs of XlMCM9 were searched in the human genome with BLAST. Two overlapping sequence entries on chromosome 6 were found (NT_025741 and NT_086697, on GenBank) revealing highest alignment significance. The identified human sequences were coding for amino acid stretches, which were highly similar to XlMCM9 over the entire length of the protein, strongly suggesting that a human MCM9 with a similar size as the *Xenopus* protein exists.

Next, using the GNOMON routine within BLAST (which corrects artificial frame shifts, see Materials and Methods 2.1), to generate ab initio proteins, a human MCM9 was found at exactly the same position on chromosome 6, highly similar to XlMCM9. This protein was in its N-terminus 100% identical to the first 385 aa of the reported truncated 391 aa long hMCM9 (Yoshida, 2005). Consequently, multiple partially overlapping EST sequences corresponding to the human MCM9 region were also identified (e.g. CV030253, CX756843 (which contains the full Walker A and B motif), DR008069, on GenBank), demonstrating that a mRNA of the protein inclusive an intact Walker B motif and an elongated C-terminus is indeed transcribed.

Finally the Inventors searched by BLAST the human genome with the hMCM9 protein generated by GNOMON. Over 30 BLAST hits on chromosome 6 were found, covering nearly all the hMCM9 sequence generated by GNOMON, giving direct EST evidence from aa 1 to aa 1060. Some hits were located at the locus previously annotated as MCMDC1 (as MCM-containing domain 1) at the position 6q 22.31, corresponding to the 7 exons of truncated hMCM9 previously described (Yoshida, 2005). In addition, more hits were identified further downstream of the MCMDC1 locus and beyond the ASF1 gene, which is located in an intron of HMCM9 and transcribed in the opposite direction, corresponding to 6 more exons of the hMCM9 gene. Finally, on the map of the human chromosome 6 at position 6q22.31, the entire open reading frame of the HsMCM9 gene with the corresponding protein is also annotated as the entry hmm17631 in the GNOMON model in Map viewer, as member of the MCM2/3/5 family. Thus, this new hMCM9 gene consists of 13 exons, giving rise to a mRNA of 4789 nucleotides containing 1366 nucleotides of untranslated 3' sequences. The corresponding hMCM9 protein consists of 1143 aa, thus having a similar length as the identified proteins in *Xenopus*, mouse and chicken. These results show that the recently reported truncated hMCM9 (Yoshida, 2005) is an N-terminal fragment of the whole protein and that the stop-codon reported in this sequence and considered as the end of the protein, corresponds to the end of exon seven.

The here identified full length hMCM9 shares 55.0% identity with XlMCM9 and 63.8% identity with the MmMCM9 over its entire length (FIG. 2A and 2B). These findings show that all new identified members of the MCM9 family (*Xenopus*, chicken, mouse and human) are similar in length and highly conserved.

Characterization and Classification of the New MCM9 Proteins

The most striking feature of the MCM9 protein in different organisms is their highly conserved N-terminus (aa 1-650), which contains all classical features of MCM2-7 and MCM8 proteins, including Zn finger-like domains, the Walker A and B motifs as well as a full MCM2-7 family domain (FIG. 1A and FIG. 2A). Only the mouse protein appears to contain additional 150 aa on its N-terminus. However, MCM9 shares a much higher homology to MCM8 than to the other MCM2-7 proteins (FIG. 2A and FIG. 2C) and it is only present in vertebrates. Thus, MCM8 and MCM9 represent a distinct sub-family of MCM DNA helicases, perhaps to fulfill special needs which came up with the more complex biology and development of multicellular organisms, especially in vertebrates. Indeed, MCM8 and MCM9 are present in vertebrates, but are absent in yeast, worms and flies. In contrast, the C-terminal half of all identified MCM9 proteins (aa 650 to the end), is less conserved (FIG. 2B), unique and not present in other MCM proteins, although a weak homology to human MCM8 exists. No obvious protein signatures or motifs could be identified with a significant score within this part. However, the C-terminus contains several short, nevertheless highly conserved stretches. The elongated C-terminus of this newly identified MCM9 protein might not be directly involved in helicase activity, but in binding to other factors or helicases.

Conclusions

The newly identified MCM9 protein seems to be generally present in vertebrates (e.g. also in dog within the contig NW_139836, on GenBank), cow (XP_584574, on protein sequence database) and zebra fish (within the contig CAAK01001524.1, on GenBank) whereas in *D. melanogaster*, *C. elegans* and *S. cerevisiae* there appears to be no MCM9 homolog. The previously identified HsMCM9 protein, which is shorter in size than MCM proteins, was annotated as MCMDC1 in the GenBank public database (NM_153255), suggesting that this protein may be a protein functionally unrelated to MCM proteins, but sharing some homology with them, in particular in one part of the MCM2-7 signature. These findings clarify this issue by establishing that MCM9 is a canonical MCM protein, more related to MCM8 than to the six MCM2-7 proteins and whose motifs and sequences are conserved in vertebrates and mammals, including humans.

Example 2

MCM9, a Protein Essentially Involved in Pre-RC Formation and Initiation of DNA Replication Experimental Procedures Plasmid Constructs The following vectors containing *Xenopus* MCM9 or parts of the gene were made:

for expression in *E. coli*: pET24d-MCM9 (EcoRI/SalI, aa1-1143), pProEXHTGST-TEV-MCM9 (EcoRI/SalI, aa1-1143), pProEXHT-Strict1 (EcoRI/XhoI, aa605-779), pProEXHT-C-term (EcoRI/XhoI, aa 605-1143), and for expression using *Baculovirus*: pFastBacGST-TEV-MCM9 (EcoRI/SalI, aa1-1143), pFastBacHT-MCM9 (EcoRI/SalI, aa1-1143), pFastBacGST-TEV-NMCM9 (EcoRI/EcoRI, aa1-654), pFastBacHT-NMCM9 (EcoRI/EcoRI, aa1-654).

The PET plasmids were obtained from Novagen and Invitrogen.

Cloning was performed using standard PCR techniques. As template to amplify the ORF of XlMCM9 cDNA clone with the Image ID 6643889 (on Pubmed) was used. Via PCR, restriction sites (see above for each construct) were introduced before and after the ORF. The vector and the PCR product were then digested with the indicated restriction enzymes and ligated using T4 ligase. Ligations were tranformed into *E. coli* DH5α, clones were grown, plasmids purified and analyzed for successful ligation using restriction digests.

Antibodies

Polyclonal antibodies against two different recombinant parts of the *Xenopus laevis* MCM9 (aa605-779) and (aa605-1143) were raised in rabbits.

Rabbits were injected with around 1 mg of protein mixed with Freud's adjuvant (1:1) in intervals of 3 weeks. The first bleed (3IP1) was taken 12 days after the third injection and was used for western blotting and depletion.

In intervals of several weeks, antigen was re-injected and more serum collected, which equally was used for western bloting and depletion.

Figure 3:
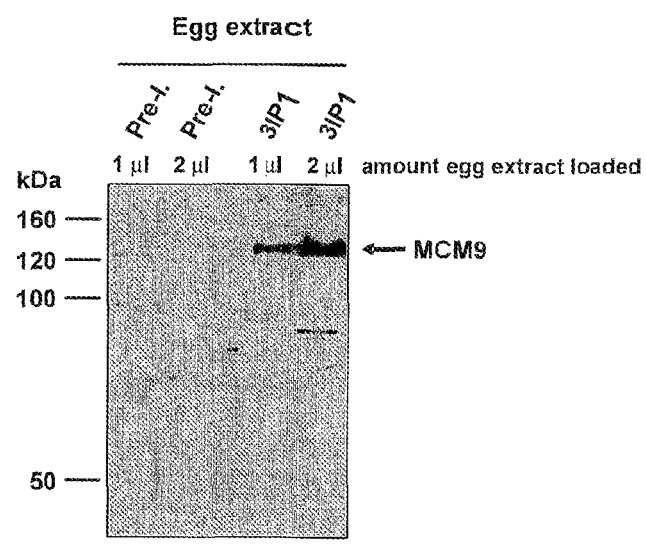

Both antibodies recognize the protein in *Xenopus* egg extracts. For example, the Western blot in FIG. 3 shows that the antibody raised against the amino acids 605 to 1143 of MCM9 recognizes the MCM9 protein in *Xenopus* egg extracts.

Polyclonal antibodies against the human hMCM9 protein were raised in rabbits as described above, using the following peptides for immunization:

human peptide 1 (aa 989-1008):
(SEQ ID NO: 65)
ETKEVSQQPPEKHGPREKVM,
and human peptide 2 (aa 809-828):
(SEQ ID NO: 66)
PWRADNVESNKKKRLALDSE.

Antibodies against ORC-2 were obtained from Dr. J. Walter, Harvard University, Boston, USA. Antibodies against CDC6 were described in Lemaître et al., 2002, Nature. Antibodies against all MCM2-7 were described in Maiorano et al., 2000, JBC, antibodies against MCM8 in Maiorano et al., 2005, Cell, and antibodies against cdt1 in Maiorano et al., 2000, Nature.

The Mock antibody is obtained from rabbit serum before immunization with the MCM9 recombinant protein.

RT-PCR

Extraction of total human RNA from HeLa cells was performed using standard techniques with the RNeasy Mini Kit (Qiagen, Cat. Nr. 74104). Purified RNA (1 ug) was reversed transcribed using SuperScript III First-Strand Synthesis System (Invitrogen, Cat. Nr. 18080-051) with poly (dT) primers. Next, PCR reaction was performed using Pfu Turbo DNA Polymerase (Stratagene, Cat. Nr. 600250) with specific primers for hMCM9.

To obtain the fragments of human MCM9 shown in FIG. 11, the following primers were used:

for fragment A:
(SEQ ID NO: 67)
5': TAC AGG AAC ACG GGT CAG
(SEQ ID NO: 68)
3': GAA ACA TCA GGC GAG CAT for fragment B:
(SEQ ID NO: 69)
5': TAC AGG AAC ACG GGT CAG
(SEQ ID NO: 70)
3': TGC CAT GAA ATC AAA CCA ATC for fragment C
(SEQ ID NO: 71)
5': TTT GAT TTC ATG GCA ACT CAT
(SEQ ID NO: 72)
3': CGC ATT GGA GCT GTG GTT GTA for fragment D:
(SEQ ID NO: 73)
5': TTG ATA GTG CAC TGC GAA GGT
(SEQ ID NO: 74)
3': TGC ATT ACA ATC CCG TAA A Cloning of the entire cDNA of human MCM9 was performed using the following primers:

```
                                          (SEQ ID NO: 75)
5' GGGGGGGTCGACCAGCCATTACCTAGATTCAAG 3' (forward)

(SEQ ID NO: 76)
5' GGGGGGCTCGAGCAGAAAGCTTTTCCCAACTA 3' (reverse).
```

Proteins Expression and Purification

For expression in *E. coli*, vectors were transformed into *E. coli* codon plus strain (Stratagene) and cultivated in minimal medium. Expression cultures were grown at 37 degrees to an OD of 0.3, then shifted to room temperature and at an OD of 0.8 induced for two hours with 0.5 mM IPTG. Cells were harvested by centrifugation and frozen in liquid N2.

For expression in SF9 cells, a construct was transformed in DH10bac *E. coli* (Kit Invitrogen), colonies containing recombinant virus DNA were identified and the DNA purified and transfected into SF9 cells. After virus amplification, 500 ml cultures of infected SF9 were grown and frozen in liquid N2.

To purify recombinant GST (Glutathione S-transferase)-MCM9 from Sf9 cells, cells were lysed in Dicis-Buffer (300 mM NaCl, 150 mM KoAC, 20 mM Tris pH 6.8, 2 mM MgCl2, 10% Glycerol, 0.01 NP40)+0.1% NP40.) by sonication. After centrifugation (15 min, 15 000 rpm in an SS34 rotor), the supernatant was incubated either with Glutathione-Sepharose 4B (Amersham Bioscience) or Ni-NTA Sepharose (Qiagen) for 40 min at 4° C. After binding, the GSH (glutathione)-beads were washed with 20 volumes of Dicis-Buffer. Elution of the GST-fusion protein was performed using one volume of Dicis-buffer+20 mM GSH at RT for 15 min for the Glutathione-Sepharose beads. Ni-NTA beads were washed with Dicis-buffer+20 mM imidazol and eluted stepwise with Dicis-buffer supplemented with 50, 100 and finally 150 mM.

To purify recombinant His-MCM9, the protocol is similar to the above protocol of GST-MCM9 purification, except that the protein is bound to Ni-beads (resins) and is eluted with increasing concentrations of imidazole in the buffer (50, 100, 150 mM imidazole).

*Xenopus* Egg Extracts and DNA Replication Reactions

Egg extracts, were prepared and used as previously described (Mechali and Harland, 1982; Menut et al., 1988). Depletion and reconstitution experiments were as previously described (Maiorano et al., 2000b).

Briefly, *Xenopus* low speed egg extracts were supplemented with cycloheximide (250 µg/ml) and double-depleted with anti-MCM9 serum coupled to Protein-A sepharose beads or recombinant protein A sepharose (Pharmacia, 50% beads to extract ratio), for 40 minutes at 4° C.

*Xenopus* Egg Extracts

Egg extracts were prepared as described previously (Menut et al, 1998). Upon thawing, egg extracts were supplemented with cycloheximide (250 µg/ml) and an energy regeneration system (10 µg/ml creatine kinase; 10 mM creatine phosphate; 1 mM ATP; 1 mM MgCl$_2$). To follow DNA replication by incorporation of α-[$^{32}$P] dNTP into newly replicated DNA, 1 µl of α-[$^{32}$P] dNTP (3000 Ci/mmol) was added to standard reaction of 50 µl.

Immunopurification Procedures

Immunopurification was performed by incubation of egg extract with the indicated antibody (MCM9, Cdt1 or unspecific antibody) for 60 min at 4 degrees. Then, Protein A-sepharose was added and incubated for another 60 min at 4 degrees. Next, the Protein A-sepharose was extensively washed with XB and bound proteins were finally eluted with SDS-sample buffer. Samples were separated on a SDS-PAGE and analyzed by western blotting.

Chromatin Purification

Sperm DNA was incubated in egg extract for the 40, 60 or 120 minutes. Chromatin fractions were obtained by diluting with 5 volumes of XB buffer (10 mM HEPES-KOH pH 7.7, 100 mM KCl, 0.1 mM CaCl 2, 1 mM MgCl2, 5% sucrose)+ 0.3% Triton X-100, keeping them for 5 min at 4° C. Next, the extraction was purified by centrifugation through a sucrose cushion (0.7 M Sucrose in XB). The pellet containing the chromatin fraction was solubilized in sample buffer for SDS-PAGE analysis.

Results:

Biological Characterization of MCM9

In FIG. 4, chromatin purifications after indicated times were blotted against MCM9 and ORC2 (as a loading control). Lanes 3 and 4 show that MCM9 associates with chromatin. Lane 2 is a negative control (no DNA added). The last lane (+Geminin) shows that MCM9 is also present on chromatin when replication is blocked by the addition of geminin. However, MCM9 is likely to be less stable than other proteins involved in DNA replication like ORC, CDC6 or Cdt1.

FIG. 5B shows that depletion of MCM9 from an egg extract abolishes DNA replication. First, the complete depletion of MCM9 was assessed by a western blot of egg extract, after incubation with non-specific antibody (Mock) or antibody against MCM9. The results shown in FIG. 5A indicate that the MCM9 protein can be completely removed from the egg extract as seen in Δ MCM9. Then, a replication kinetics of Mock-depleted egg extract (squares) and MCM9-depleted egg extract (circles) was carried out. The results shown in FIG. 5B indicate that depletion of MCM9 abolishes DNA replication.

Figure 6:
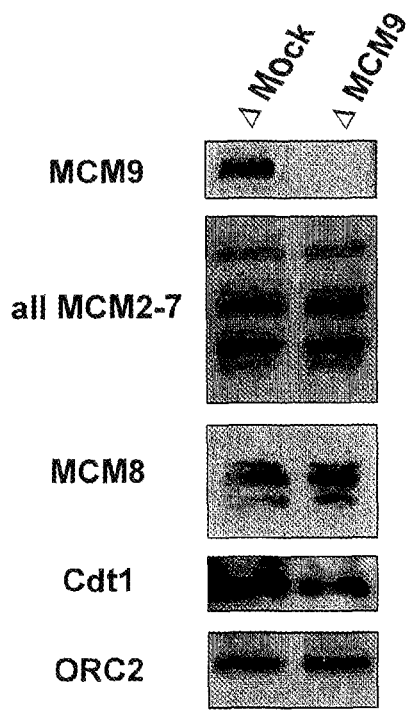

A western blot analysis of egg extract either Mock-depleted or MCM9-depleted for other proteins involved in DNA licensing or replication was then carried out. The results shown in FIG. 6 indicate that the depletion of MCM9 from an egg extract does not (quantitatively) codeplete other proteins involved in DNA licensing/replication. Thus, MCM9 is essential for DNA replication and, by depleting only MCM9, DNA replication is abolished.

Figure 7:
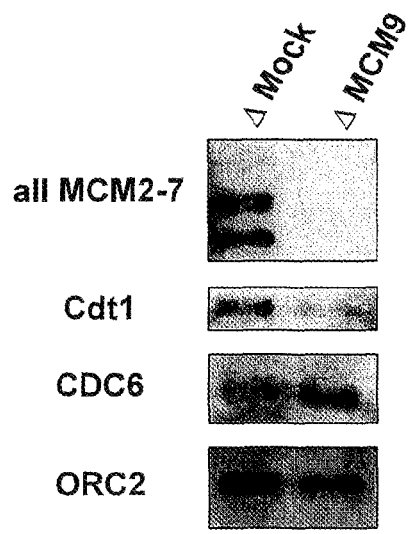

FIG. 7 shows a western blot analysis of chromatin assembled either in a Mock-depleted or MCM9-depleted egg extract. Chromatin which was assembled in MCM9-depleted extract does not contain MCM2-7 proteins and less Cdt1 than in Mock-depleted egg extract. Thus, depletion of MCM9 from egg extract inhibits the loading of the MCM2-7 complex on chromatin. This result indicates that blocking MCM9 protein allows stopping DNA replication at an early stage, before the production of single strand DNAs.

Figure 8:
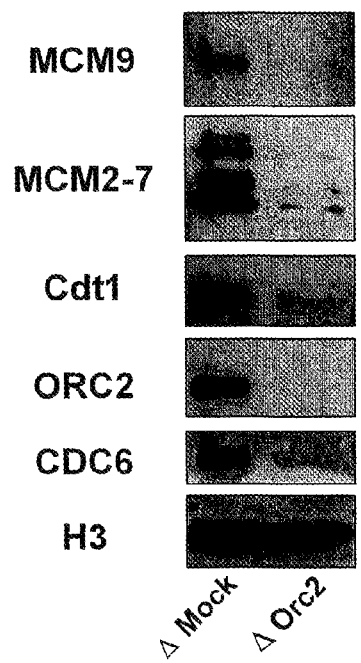

FIG. 8 shows a western blot analysis of chromatin assembled either in a Mock-depleted or ORC2-depleted egg extract. Chromatin which was assembled in an ORC2-depleted extract is devoid of pre-RC proteins (Cdt1, CDC6, MCM2-7) and also does not contain MCM9. Histon H3 (H3) is shown as a loading control. Association of MCM9 with chromatin is thus dependent on ORC (Origin Recognition Complex). MCM9 certainly binds chromatin at the replication origin via ORC.

Figure 9:
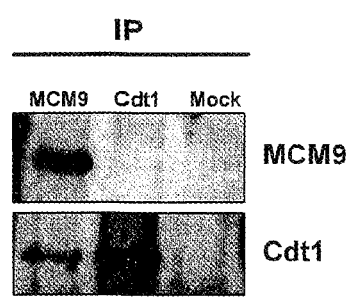

In FIG. 9, MCM9 is shown to interact with Cdt1 in egg extract: a western blot analysis of immune purifications of MCM9, Cdt1 and a Mock-purification (done with an unspecific antibody) was carried out. In the MCM9 purification, a substantial amount of Cdt1 is present, showing that these two proteins interact in egg extract (FIG. 9). Thus, MCM9 binds chromatin by associating with cdt1, a protein which is necessary for replication.

Recombinant Expression of MCM9

Figure 10:
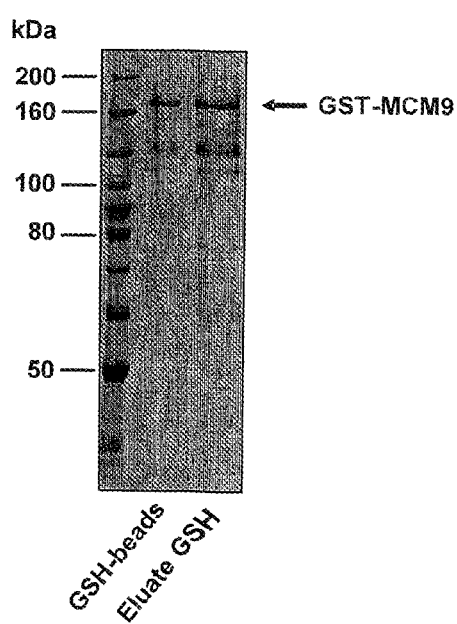

GST-TEV-MCM9 is purified from Baculovirus-infected SF9 cells. In FIG. 10, Coomasie stained SDS-PAGE shows GSH-beads loaded with GST-TEV-MCM9 after incubation with SF9 cell-lysate and the GSH-eluated protein GST-TEV-MCM9.

Evidence for the MCM9 in Human Cells

An RT-PCR analysis was performed on human cDNA with specific primers pairs corresponding to different fragments of the human MCM9. These fragments represented in FIG. 11B overlap on almost the full-length human MCM9 protein. The results shown in FIG. 11A reveal the presence of specific bands corresponding to the different parts of the human MCM9.

References

Gozuacik, D., Chami, M., Lagorce, D., Faivre, J., Murakami, Y., Poch, O., Biermann, E., Knippers, R., Brechot, C. and Paterlini-Brechot, P., 2003. Nucleic Acids Res, 31, 570-579.

Higgins D., Thompson J., Gibson T. Thompson J. D., Higgins D. G., Gibson T. J., 1994. Nucleic Acids Res., 22, 4673-4680.

Johnson, E. M., Kinoshita, Y. and Daniel, D. C., 2003. Nucleic Acids Res, 31, 2915-2925.

Kearsey, S. E. and Labib, K., 1998. Biochim. Biophys. Acta, 1398, 113-136.

Koonin, E. V., 1993. Nucleic Acids Res., 21, 2541-2547.

Maiorano, D., Moreau, J., and Mechali, M., 2000. Nature, 404, 622-625.

Maiorano, D., Cuvier, O., Danis, E. and Mechali, M., 2005. Cell, 120, 315-328.

Mechali, M., and Harland, R. M.,1982. Cell, 30, 93-101.

Menut, S., Lemaitre, J. M., Hair, A., and Méchali, M.,1988. Oxford University Press, Ed J D Richter.

Mulder, N. J., Apweiler, R., Attwood, T. K., Bairoch, A., Bateman, A., Binns, D., Bradley, P., Bork, P., Bucher, P., Cerutti, L., 2005. Nucleic Acids Res., 33, D201-205.

Pearson, W. R., Wood, T., Zhang, Z. and Miller, W., 1997. Genomics, 46, 24-36.

Yoshida, K., 2005. Biochem. Biophys. Res. Corn., 331, 669-674.

Zhang, Z., Schwartz, S., Wagner, L. and Miller, W., 2000. J. Comput. Biol., 7, 203-214.

---

The invention claimed is:

1. An isolated polypeptide consisting of one of the following sequences: SEQ ID NO: 2, and SEQ ID NO: 8.

2. A method for the in vitro or ex vivo production of catalytically active MCM9 helicase in foreign expression systems, or in vitro systems for coupled transcription/translation of the MCM9 cDNA, or translation of the MCM9 mRNA into xenopus oocyte or egg extracts, comprising the steps of:
   a) lysing of cells expressing MCM9 proteins in the following buffer or equivalent, 20 mM TrisHCl pH 8.5, 100 mM KCl, 5 mM β-mercaptoethanol, 5-10 mM imidazole, 10% glycerol (v/v), proteases inhibitors;
   b) purifying the soluble MCM9 proteins by nickel affinity chromatography technology or equivalent or similar affinity chromatography technology;
   c) eluting bound proteins in 10 mM TrisHCl pH 8.5, 100 mM KCl, 5 mM β-mercaptoethanol, 100-250 mM imidazole, 10% glycerol (v/v), proteases inhibitors;
   d) supplementing purified MCM9 proteins, with 0.1 mg/ml of BSA;
   e) desalting on a Bio-spin P30 column (Biorad) equilibrated with 20 mM TrisHCl pH 7.4, 150 mM NaCl, 0.5 mM EDTA, 1 mM DTT, 0.01% Triton X-100 for helicase and ATPase activities, or in XB (100 mM KCl, 0.1 mM $CaCl_2$, 2 mM $MgCl_2$, 10 mM Hepes-KOH, 50 mM sucrose, pH 7.7) for egg extracts reconstitution experiments; and
   f) supplementing the purified MCM9 proteins with 25% glycerol and storage at −20° C;
   wherein the MCM9 protein is the isolated polypeptide according to claim 1.

3. A pharmaceutical composition comprising the isolated polypeptide of claim 1 as an active substance, and a pharmaceutically acceptable vehicle.

* * * * *

UNITED STATES PATENT AND TRADEMARK OFFICE
CERTIFICATE OF CORRECTION

PATENT NO. : 8,497,101 B2
APPLICATION NO. : 11/914374
DATED : July 30, 2013
INVENTOR(S) : Mechali et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1422 days.

Signed and Sealed this

Fifteenth Day of September, 2015

Michelle K. Lee
*Director of the United States Patent and Trademark Office*